US011359021B2

(12) United States Patent
Gu et al.

(10) Patent No.: US 11,359,021 B2
(45) Date of Patent: Jun. 14, 2022

(54) PD-L1 ANTIBODY, ANTIGEN-BINDING FRAGMENT THEREOF, AND PHARMACEUTICAL USE THEREOF

(71) Applicants: JIANGSU HENGRUI MEDICINE CO., LTD., Jiangsu (CN); SHANGHAI HENGRUI PHARMACEUTICAL CO., LTD., Shanghai (CN)

(72) Inventors: Xiaoling Gu, Shanghai (CN); Jiahua Jiang, Shanghai (CN); Lei Zhang, Shanghai (CN); Qiyue Hu, Shanghai (CN); Jinming Gu, Shanghai (CN); Weikang Tao, Shanghai (CN)

(73) Assignees: JIANGSU HENGRUI MEDICINE CO., LTD., Jiangsu (CN); SHANGHAI HENGRUI PHARMACEUTICAL CO., LTD., Shanghai (CN)

(*) Notice: Subject to any disclaimer, the term of this patent is extended or adjusted under 35 U.S.C. 154(b) by 106 days.

(21) Appl. No.: 16/960,297

(22) PCT Filed: Jan. 9, 2019

(86) PCT No.: PCT/CN2019/070982
§ 371 (c)(1),
(2) Date: Jul. 6, 2020

(87) PCT Pub. No.: WO2019/137397
PCT Pub. Date: Jul. 18, 2019

(65) Prior Publication Data
US 2020/0339692 A1    Oct. 29, 2020

(30) Foreign Application Priority Data
Jan. 10, 2018  (CN) .......................... 201810023267.0

(51) Int. Cl.
*C07K 16/28*  (2006.01)
*A61P 35/00*  (2006.01)
*G01N 33/574*  (2006.01)
*A61K 39/00*  (2006.01)

(52) U.S. Cl.
CPC .......... *C07K 16/2827* (2013.01); *A61P 35/00* (2018.01); *G01N 33/574* (2013.01); *A61K 2039/51* (2013.01); *C07K 2317/21* (2013.01); *C07K 2317/52* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| 6,803,192 | B1  | 10/2004 | Chen |
| 8,617,546 | B2* | 12/2013 | Kang .............. A61K 39/39558 |
|           |     |         | 424/130.1 |
| 10,815,304 | B2* | 10/2020 | Qu |
| 2014/0335093 | A1 | 11/2014 | Olive |

FOREIGN PATENT DOCUMENTS

| CN | 101104640 | 1/2008 |
| CN | 105777906 A | 7/2016 |
| CN | 106243225 | 12/2016 |
| CN | 106699891 | 5/2017 |
| WO | 0139722 A2 | 6/2001 |
| WO | 2010089411 A2 | 8/2010 |
| WO | 2013173223 A1 | 11/2013 |
| WO | 2013181634 A2 | 12/2013 |
| WO | 2014022758 A1 | 2/2014 |
| WO | 2014055897 A2 | 4/2014 |
| WO | 2014100079 A1 | 6/2014 |
| WO | WO-2014/151006 | 9/2014 |
| WO | 2014195852 A1 | 12/2014 |
| WO | 2015036511 A1 | 3/2015 |
| WO | 2015048520 A1 | 4/2015 |
| WO | WO-2016/149201 A2 | 9/2016 |
| WO | 2017084495 A1 | 5/2017 |
| WO | WO-2017/084495 A1 | 5/2017 |
| WO | WO-2017/196867 | 11/2017 |
| WO | WO-2019/129136 A1 | 7/2019 |

OTHER PUBLICATIONS

Alfthan, K., et al., "Properties of a single-chain antibody containing different linker peptides," Protein Engineering, vol. 8, No. 7, 1995, pp. 725-731.
Choi, I., et al., Recombinant chimeric OKT3 scFv IgM antibodies mediate immune suppression while reducing T cell activation in vitro, Eur. J. Immunol., 2001, vol. 31, pp. 94-106.
Hamanishi, J., et al., "Safety and Antitumor Activity of Anti-PD-1 Antibody, Nivolumab, in Patients with Platinum-Resistant Ovarian Cancer," Journal of Clinical Oncology, vol. 33, 2015, 13 pages.
Holliger, P., et al., "Diabodies": Small bivalent and bispecific antibody fragments, Proc. Natl. Acad. Sci. USA, vol. 90, Jul. 1993, pp. 6444-6448.
Hu, S., et al., "Minibody: A Novel Engineered Anti-Carcinoembryonic Antigen Antibody Fragment (Single-Chain Fv-$C_H 3$) Which Exhibits Rapid, High-Level Targeting of Xenografts," Cancer Research, vol. 56, 1996, pp. 3055-3061.

(Continued)

*Primary Examiner* — Laura B Goddard
*Assistant Examiner* — Sarah A Alsomairy
(74) *Attorney, Agent, or Firm* — Foley & Lardner LLP

(57) ABSTRACT

A novel PD-L1 antibody, an antigen-binding fragment thereof, and a pharmaceutical use thereof. A humanized antibody comprising a CDR of the PD-L1 antibody, a pharmaceutical composition comprising the PD-L1 antibody and the antigen-binding fragment thereof and a use of the PD-L1 antibody as a drug. A use of a humanized PD-L1 antibody in preparing a drug for treating diseases or disorders associated with PD-L1.

20 Claims, 4 Drawing Sheets

Specification includes a Sequence Listing.

(56) References Cited

OTHER PUBLICATIONS

International Search Report dated Apr. 10, 2019 issued in International Application No. PCT/CN2019/070982, 12 pages.
Kipriyanov, S.M., et al., "Bispecific Tandem Diabody for Tumor Therapy with Improved Antigen Binding and Pharmacokinetics," J. Mol. Biol., 1999, vol. 293, pp. 41-56.
Todorovska, A., et al., Design and application of diabodies, triabodies and tetrabodies for cancer targeting, Journal of Immunological Methods, vol. 248, 2001, pp. 47-66.
Zhan, M., et al., "From monoclonal antibodies to small molecules: the development of inhibitors targeting the PD-1/PD-L1 pathway," Drug Discovery Today, vol. 21, No. 6, 2016, pp. 1027-1036.
Written Opinion dated Apr. 10, 2019 issued in International Application No. PCT/CN2019/070982, with English translation, 9 pages.

* cited by examiner

PD-L1 ANTIBODY, ANTIGEN-BINDING FRAGMENT THEREOF, AND PHARMACEUTICAL USE THEREOF

The present application is a 371 of PCT/CN2019/070982, filed on Jan. 9, 2019, which claims the priority of the Chinese Application No. 201810023267.0, filed on Jan. 10, 2018, the contents of which are incorporated herein by its entirety.

FIELD OF INVENTION

The present disclosure relates to a PD-L1 antibody and an antigen-binding fragment thereof. Further, the present disclosure also relates to a chimeric antibody and a humanized antibody comprising CDR of the PD-L1 antibody, and the present disclosure also relates to a pharmaceutical composition comprising the PD-L1 antibody and the antigen-binding fragment thereof, and a use thereof as a diagnostic agent and a therapeutic medicament for diseases associated with PD-L1.

BACKGROUNDS

The statements herein merely provide background information related to the present invention and do not necessarily constitute prior art.

Tumor immunotherapy is a long-term hot spot in the field of tumor therapy, in which T cell tumor immunotherapy is the core. Tumor immunotherapy is to make full use of and mobilize killer T cells in tumor patients to kill tumors. It may be the most effective and safest way to treat tumors. Meanwhile, tumor escape is a tremendous hurdle for tumor immunotherapy. Tumor cells promote the rapid growth of tumors by exerting their own suppressive effect on the immune system.

The relationship between tumor immune, escape mechanism and body immune response to the tumor is very complicated. In the early stage of tumor immunotherapy, tumor-specific killer T cells were biologically active, but they lost their killing function in the later stage, of tumor growth. Therefore, tumor immunotherapy is to maximize patient's own immune system response to tumor. The key of tumor immunotherapy is to not only activate the original body immune system response, but also maintain the duration and intensity of the immune system response.

There are two signaling pathway systems of the activation of T cells in human body. In addition to providing the first signal by presenting MHC-antigen peptides to the T cells through antigen-presenting cells, a series of co-stimulatoty molecules are also required to provide the second signal in order for T cells to produce a normal immune response. This dual signaling pathway system plays a vital role in the balance of body immune system, and it strictly regulates the body to trigger different immune responses to autoantigen and exogenous antigens. The absence of the second signal provided by the co-stimulatory molecule will result in non-response or sustaining specific immune response of the T cells, thus leading to tolerance. Therefore, the second signaling pathway plays a key regulatory role in the entire process of immune response.

It was found in 1992 that Programmed Death-1 (PD-1) molecule is a protein receptor expressed an the surface of T cells, participating in the apoptosis of cells. PD-1 belongs to CD28 family and has 23% of amino acid homology with cytotoxic. T lymphocyte antigen 4 (CTLA-4), but: its expression is mainly expressed in activated T cells, H cells and myeloid cells, which is different from that of CTLA. There are two ligands of PD-1, PD-L1 and PD-L2, respectively. PD-L1 is mainly expressed in T cells, B cells, macrophages and dendritic cells (DC) and the expression of which can be up-regulated on activated cells. The expression of PD-L2 is relatively limited, mainly on antigen-presenting cells, such as activated macrophages and dendritic cells.

PD-L1 inhibits the immune system by binding with PD-1 and B7-1. PD-L1 is expressed in many tune or cells and immune cells in the tumor tissue microenvironment. New research finds that high expression of PD-L1 protein was detected in human tumor tissues such as breast cancer, lung cancer, gastric carcinoma, intestinal cancer, kidney cancer, melanoma, non-small cell lung cancer, colon cancer, bladder cancer, ovarian cancer, pancreatic cancer and liver cancer, and the expression level of PD-L1 is closely associate with the clinical and prognosis of patients.

Since PD-L1 plays a role in inhibiting the proliferation of T cells in the second signaling pathway, blocking the binding of PD-L1/PD-1 has become a very promising novel target of tumor immunotherapy.

At present, many multinational pharmaceutical companies are developing monoclonal antibodies against PD-L1. By blocking the binding of PD-L1/PD-1, it can maximize patient's own immune system response to tumors, thus achieving the purpose of killing tumor cells. The following are related patents: WO0139722, WO2013173223, WO2014195852, WO2013181634, WO2015948520, WO2015030511, US2014335093, WO20144100079, WO2014055897, U.S. Pat. No. 6,803,192B1, WO2014022758, U.S. Pat. No. 8,617,546B2 and WO2010089411A2.

CONTENT OF THE PRESENT INVENTION

The present disclosure provides a monoclonal antibody or an antigen-binding fragment (also referred to as a human PD-L1 binding molecule) that binds to the amine acid sequence or three-dimensional structure of the extracellular region of PD-L1.

In some alternative embodiments, the present disclosure provides a monoclonal antibody or an antigen-binding fragment thereof that binds to human PD-L1, which comprises:

(i) a heavy chain variable region and a light chain variable region, wherein the heavy chain variable region comprises HCDR1, HCDR2 and HCDR3 having amino acid sequences of SEQ ID NOs: 10, 12 and 13, respectively; and the light chain variable region comprises LCDR1, LCDR2 and LCDR3 having amino acid sequences of SEQ ID NOs: 14, 15 and 16, respectively; wherein $X_1$ is F or M, $X_2$ is R or V and $X_3$ is N or 14 in the HCDR2 of SEQ ID NO: 12; or (ii) a heavy chain variable region and a light chain variable region, wherein the heavy chain variable region comprises HCDR1, HCDR2 and HCDR3 having amino acid sequences of SEQ ID NOs: 11, 12 and 13, respectively; and the light chain variable region comprises LCDR1, LCDR2 and LCDR3 having amino acid sequences of SEQ ID NOs: 14, 15 and 16, respectively; wherein $X_1$ is F or M, $X_2$ is R or V and $X_3$ is N or H in the HCDR2 of SEQ ID NO: 12; or (iii) a heavy chain variable region and a light chain variable region, wherein the heavy chain variable region comprises HCDR1, HCDR2 and HCDR3 having amino acid sequences of SEQ ID NOs: 20, 21 and 22, respectively; and the light chain variable region comprises LCDR1, LCDR2 and LCDR3 having amino acid sequences of SEQ ID NOs: 23, 24 and 25, respectively; wherein HCDR1, HCDR2 HCDR3 and LCDR1, LCDR2, LCDR3, respectively, are not SEQ ID NOs: 30, 38, 22, 23, 40 and 25 simultaneously.

wherein $X_4$ is S or D, $X_5$ is Y or K, $X_6$ is H or M, $X_7$ is T, S, H or $X_8$ is S, N G, $X_9$ is S, L or G, $X_{10}$ is F, L, W or M and $X_{11}$ is A, P or T, $X_{12}$ is M, V, L or S, $X_{13}$, is F or Y in the SEQ ID NOs: 20 and 21, and $X_{14}$ is V or A, $X_{15}$ is Y or N, $X_{16}$ is A, L or V and $X_{17}$ is E, Y, or A in the LCDR2 of SEQ ID NO: 24.

In scone embodiments, the monoclonal antibody or the antigen-binding fragment thereof that binds to human PD-L1, as defined above, comprises a heavy chain variable region and a light chain variable region, wherein the heavy chain variable region comprises a HCDR1 having an amino acid sequence of SEQ ID NO: 10, a HCDR2 having an amino acid sequence of SEQ ID NO: 28 or 29 and a HCDR3 having an amino acid sequence of SEQ ID NO: 13, the light chain variable region comprises LCDR1, LCDR2 and LCDR3 having amino acid sequences of SEQ ID NOs: 14, 15 and 16, respectively.

In some embodiments, the monoclonal antibody or the antigen-binding fragment thereof that binds to human PD-L1, as defined above, comprises a heavy chain variable region and a light chain variable region, wherein the heavy chain variable region comprises a HCDR1 having an amino acid sequence of SEQ ID NO: 11, a HCDR2 having an amino acid sequence of SEQ. ID NO: 28 or 29 and a HCDR3 having an amino acid sequence of SEQ ID NO: 13, the light chain variable region comprises LCDR1, LCDR2 and LCDR3 having amino acid sequences of SEQ ID NOs: 14, 15 and 16, respectively.

In some embodiments, the monoclonal antibody or the antigen-binding fragment thereof that binds to human PD-L1, as defined above, comprises a heavy chain variable region and a light chain variable region, wherein the heavy chain variable region comprises a HCDR1 having an amino acid sequence of SEQ ID NO: 30, a HCDR2 having an amino acid sequence of any one of SEQ ID NOs: 32 to 37 and a HCDR3 having an amino acid. sequence of SEQ ID NO: 22, the light chain variable region comprises a LCDR1 having an amino acid sequence of SEQ ID NO: 23, a LCDR2 having an amino acid sequence of any one of SEQ ID NOs: 39, 40, 41, 67 and 69 and a LCDR3 having an amino acid sequence of SEQ ID NO: 25.

In some embodiments, the monoclonal antibody or the antigen-binding fragment thereof that binds to human PD-L1, as defined above, comprises a heavy chain variable region and a light chain variable region, wherein the heavy chain variable region comprises a HCDR1 having an amino acid sequence of SEQ ID NO: 31, a HCDR2 having an amino acid sequence of any one of SEQ ID NOs; 32, 33, 34, 35, 36 and 37 and a HCDR3 having an amino acid sequence of SEQ ID NO: 22, the light chain variable region comprises a LCDR1 having an amino acid sequence of SEQ ID NO: 23, a LCDR2 having an amino acid sequence of any one of SEQ ID NOs: 39, 40, 41, 67 and 69 and a LCDR3 having an amino acid sequence of SEQ ID NO: 25.

In some embodiments, the heavy chain variable region of the monoclonal antibody or the antigen-binding fragment thereof, as defined above, comprises HCDR1, HCDR2 and HCDR3 having amino acid sequences of SEQ ID NO: 10, SEQ ID NO: 28 and SEQ ID NO: 13, respectively; the light chain variable region of which comprises LCDR1, LCDR2 and LCDR3 having amino acid sequences of SEQ ID NOs: 14-16, respectively; or In some embodiments, the heavy chain variable region of the monoclonal antibody or antigen-binding fragment thereof, as defined above, comprises HCDR1, HCDR2 and HCDR3 having amino acid sequences of SEQ ID NO: 11, SEQ ID NO: 28 and SEQ ID NO: 13, respectively; the light chain variable region of which comprises LCDR1, LCDR2 and LCDR3 having amino acid sequences of SEQ ID NOs: 14-16, respectively; or In some embodiments, the heavy chain variable region of the monoclonal antibody or antigen-binding fragment thereof, as defined above, comprises HCDR1, HCDR2 and HCDR3 having amino acid sequences of SEQ ID NO: 11, SEQ ID NO: 29 and SEQ ID NO: 13, respectively; the light chain variable region of which comprises LCDR1, LCDR2 and LCDR3 having amino acid sequences of SEQ ID NOs: 14-16, respectively; or In some embodiments, the heavy chain variable region of the monoclonal antibody or antigen-binding fragment thereof, as defined above, comprises HCDR1, HCDR2 and HCDR3 having amino acid sequences of SEQ ID NO: 30, SEQ ID NO: 32 and SEQ ID NO: 22, respectively; the light chain variable region of which comprises LCDR1, LCDR2 and LCDR3 having amino acid sequences of SEQ ID NO: 23, SEQ ID NO: 39 and SEQ ID NO: 25, respectively; or In some embodiments, the heavy chain variable region of the monoclonal antibody or antigen-binding fragment thereof, as defined above, comprises HCDR1, HCDR2 and HCDR3 having amino acid sequences of SEQ ID NO: 30, SEQ ID NO: 32 and SEQ ID NO: 22, respectively; the fight chain variable region of which comprises LCDR1, LCDR2 and LCDR3 having amino acid sequences of SEQ ID NO: 23, SEQ ID NO: 40 and SEQ ID NO: 25, respectively; or In some embodiments, the heavy chain variable region of the monoclonal antibody or antigen-binding fragment thereof, as defined above comprises HCDR1, HCDR2 and HCDR3 having amino acid sequences of SEQ ID NO: 30, SEQ ID NO: 33 and SEQ ID NO: 22, respectively; the light chain variable region of which comprises LCDR1, LCDR2 and LCDR3 having amino acid sequences of SEQ ID NO: 23, SEQ ID NO: 40 and SEQ ID NO: 25, respectively; or In some embodiments the heavy chain variable region of the monoclonal antibody or antigen-binding fragment thereof, as defined above, comprises HCDR1, HCDR2 and HCDR3 having amino acid sequences of SEQ ID NO: 30, SEQ ID NO: 34 and SEQ ID NO: 22, respectively; the light chain variable region of which comprises LCDR1, LCDR2 and LCDR3 having amino acid sequences of SEQ ID NO: 23, SEQ ID NO: 40 and SEQ ID NO: 25, respectively; or In some embodiments, the heavy chain variable region of the monoclonal antibody or antigen-binding fragment thereof, as defined above, comprises HCDR1, HCDR2 and HCDR3 having amino acid sequences of SEQ ID NO: 31, SEQ ID NO: 32 and SEQ ID NO: 22, respectively; the light chain variable region of which comprises LCDR1, LCDR2 and LCDR3 having amino acid sequences of SEQ ID NO: 23, SEQ ID NO: 40 and SEQ ID NO: 25, respectively; or In some embodiments, the heavy chain variable region of the monoclonal antibody or antigen-binding fragment thereof as defined above, comprises HCDR1, HCDR2 and HCDR3 having amino acid sequences of SEQ ID NO: 31, SEQ ID NO: 32 and SEQ ID NO: 22, respectively; the light chain variable region of which comprises LCDR1, LCDR2 and LCDR3 having amino acid sequences of SEQ ID NO: 23, SEQ ID NO: 67 and SEQ ID NO: 25, respectively.

In some embodiments, the heavy chain variable region of the monoclonal antibody or antigen-binding fragment thereof, as defined above, comprises HCDR1, HCDR2 and HCDR3 having amino acid sequences of SEQ ID NO: 31, SEQ ID NO: 32 and SEQ ID NO: 22, respectively; the light chain variable region of which comprises LCDR1, LCDR2 and LCDR3 having amino acid sequences of SEQ ID NO: 23, SEQ ID NO: 69 and SEQ ID NO: 25, respectively.

In some embodiments, the heavy chain variable region of the monoclonal antibody or antigen-binding fragment thereof, as defined above comprises HCDR1, HCDR2 and HCDR3 having amino acid sequences of SEQ ID NO: 31, SEQ ID NO: 32 and SEQ ID NO: 22, respectively; the light chain variable region of which comprises LCDR1, LCDR2 and LCDR3 having amino acid sequences of SEQ ID NO: 23, SEQ ID NO: 69 SEQ ID NO: 25, respectively.

In some embodiments, the heavy chain variable region of the monoclonal antibody or antigen-binding fragment thereof, as defined above, comprises HCDR1, HCDR2 and HCDR3 having amino acid sequences of SEQ ID NO: 30, SEQ ID NO: 35 and SEQ ID NO: 22, respectively; the light chain variable region of which comprises LCDR1, LCDR2 and LCDR3 having amino acid sequences of SEQ ID NO: 23, SEQ ID NO: 40 and SEQ ID NO: 25, respectively; or In some embodiments, the heavy chain variable region of the monoclonal antibody or antigen-binding fragment thereof, as defined above, comprises HCDR1, HCDR2 and HCDR3 having amino acid sequences of SEQ ID NO: 30, SEQ ID NO: 36 and SEQ ID NO: 22, respectively; the light chain variable region of which comprises LCDR1, LCDR2 and LCDR3 having amino acid sequences of SEQ ID NO: 23, SEQ ID NO: 40 and SEQ ID NO: 25, respectively; or In some embodiments, the heavy chain variable region of the monoclonal antibody or antigen-binding fragment thereof, as defined above, comprises HCDR1, HCDR2 and HCDR3 having amino acid sequences of SEQ ID NO: 30, SEQ ID NO: 37 and SEQ ID NO: 22, respectively; the light chain variable region of which comprises LCDR1, LCDR2 and LCDR3 having amino acid sequences of SEQ ID NO: 23, SEQ ID NO: 40 and SEQ ID NO: 25, respectively.

In some embodiments, the affinity KD value of the monoclonal antibody or the antigen-binding fragment thereof, as defined above, to human PD-L1 is less than $10^{-9}$ M or $10^{-10}$ M.

In some embodiments, the monoclonal antibody or antigen-binding fragment thereof, as defined above, cross-binds cynomolgus monkey or rhesus PD-L1 and/or mouse PD-L1.

In some embodiments, the monoclonal antibody or the antigen-binding fragment thereof, as defined above, comprises the heavy chain variable region having an amino acid sequence of SEQ ID NO: 17 and the light chain variable region having an amino acid sequence of SEQ ID NO: 19.

In some embodiments, the monoclonal antibody or the antigen-binding fragment thereof, as defined above, comprises the heavy chain variable region having an amino acid sequence of SEQ ID NO: 18 and the light chain variable region having an amino acid sequence of SEQ ID NO: 19.

In some embodiments, the monoclonal antibody or the antigen-binding fragment thereof, as defined above, comprises the heavy chain variable region having an amino acid sequence of SEQ ID NO: 26 and the light chain variable region having an amino acid sequence of SEQ ID NO: 27.

In some embodiments, the monoclonal antibody or the antigen-binding fragment thereof, as defined above, comprises the heavy chain variable region having an amino acid sequence of SEQ ID NO: 42 and the light chain variable region having an amino acid sequence of SEQ NO: 45.

In some embodiments, the monoclonal antibody or the antigen-binding fragment thereof, as defined above, comprises the heavy chain variable region having an amino acid sequence of SEQ ID NO: 43 and the light, chain variable region having an amino acid sequence of SEQ NO: 45.

In some embodiments, the monoclonal antibody or the antigen-binding fragment thereof, as defined above, comprises the heavy chain variable region having an amino acid sequence of SEQ ID NO: 44 and the light chain variable region having an amino acid sequence of SEQ ID NO: 45.

In some embodiments, the monoclonal antibody or the antigen-binding fragment thereof, as defined above, comprises the heavy chain variable region having an amino acid sequence of SEQ ID NO: 46 and the light chain variable region having amino acid sequences of any one of SEQ ID NOS: 55, 56 and 57.

In some embodiments, the monoclonal antibody or the antigen-binding fragment thereof comprises the heavy chain variable region having an amino acid sequence of SEQ ID NO: 47 and the light chain variable region having amino acid sequences of any one of SEQ ID NOs: 55, 56 and 57.

In some embodiments, the monoclonal antibody or the antigen-binding fragment thereof, as defined above comprises the heavy chain variable region having an amino acid sequence of SEQ ID NO: 48 and the light chain variable region having amino acid sequences of any one of SEQ ID NOs: 55, 56 and 57.

In some embodiments, the monoclonal antibody or the antigen-binding fragment thereof, as defined above, comprises the heavy chain variable region having an amino acid sequence of SEQ ID NO: 49 and the light chain variable region having amino acid sequences of any one of SEQ ID NOs: 55, 56 and 57.

In some embodiments, the monoclonal antibody or the antigen-binding fragment thereof comprises the heavy chain variable region having an amino acid sequence of SEQ ID NO: 50 and the light chain variable region having amino acid sequences of any one of SEQ ID NOs: 55, 56 and 57.

In some embodiments, the monoclonal, antibody or the antigen-binding fragment thereof, as defined above, comprises the heavy chain variable region having an amino acid sequence of SEQ ID NO: 51 and the light chain variable region having amino acid sequences of any one of SEQ ID NOs: 55, 56 and 57.

In some embodiments, the monoclonal antibody or the antigen-binding fragment thereof, as defined above, comprises the heavy chain variable region having an amino acid sequence of SEQ ID NO: 52 and the light chain variable region having amino acid sequences of any one of SEQ ID NOs: 55, 56 and 57.

In some embodiments, the monoclonal antibody or the antigen-binding fragment thereof, as defined above, comprises the heavy chain variable region having an amino acid sequence of SEQ ID NO: 53 and the light chain variable region having amino acid sequences of any one of SEQ NOs: 55, 56 and 57.

In some embodiments, the monoclonal antibody or the antigen-binding fragment thereof, as defined above, comprises the heavy chain variable region having an amino acid sequence of SEQ ID NO: 54 and the light chain variable region having amino acid sequences of any one of SEQ ID NOs: 55 and 57.

In some embodiments, the monoclonal antibody or the antigen-binding fragment thereof, as defined above, comprises the heavy chain variable region having an amino acid sequence of SEQ ID NO: 46 and the light chain variable region having amino acid sequences of any one of SEQ ID NOs: 55, 56, 57, 70 and 72.

In some embodiments, the monoclonal antibody or the antigen-binding fragment thereof, as defined above, comprises the heavy chain variable region having an amino acid sequence of SEQ ID NO: 47 and the light chain variable region having amino acid sequences of any one of SEQ ID NOs: 55, 56. 57, 70 and 72.

In some embodiments, the monoclonal antibody or the antigen-binding fragment thereof, as defined above, comprises the heavy chain variable region having an amino acid sequence of SEQ ID NO: 48 and the light chain variable region having amino acid sequences of any one of SEQ ID NOs: 55, 56, 57, 70 and 72.

In some embodiments, the monoclonal antibody or the antigen-binding fragment thereof, as defined above, comprises the heavy chain variable region having an amino acid sequence of SEQ ID NO: 49 and the light chain variable region having amino acid sequences of any one of SEQ ID NOs: 55, 56, 57, 70 and 72.

In some embodiments, the monoclonal antibody or the antigen-binding fragment thereof, as defined above, comprises the heavy chain variable region having an amino acid sequence of SEQ ID NO: 50 and the light chain variable region having amino acid sequences of any one of SEQ NOs: 55, 56. 57, 70 and 72.

In some embodiments, the monoclonal antibody or the antigen-binding fragment thereof, as defined above, comprises the heavy chain variable region having an amino acid sequence of SEQ ID NO: 51 and the light chain variable region having amino acid sequences of any one of SEQ ID NOs: 55, 56, 57, 70 and 72.

In some embodiments, the monoclonal antibody or the antigen-binding fragment thereof, as defined above, comprises the heavy chain variable region having an amino acid sequence of SEQ ID NO: 52 and the light chain variable region having amino acid sequences of any one of SEQ ID NOs: 55, 56, 57, 70 and 72.

In some embodiments, the monoclonal antibody or the antigen-binding fragment thereof, as defined above, comprises the heavy chain variable region having an amino acid sequence of SEQ ID NO: 53 and the light chain variable region having amino acid sequences of any one of SEQ ID NOs: 55, 56, 57, 70 and 72.

In some embodiments, the monoclonal antibody or the antigen-binding fragment thereof, as defined above, comprises the heavy chain variable region having an amino acid sequence of SEQ ID NO: 66 and the light chain variable region having amino acid sequences of any one of SEQ ID NOs: 55, 56, 57, 70 and 72.

In some embodiments, the monoclonal antibody or the antigen-binding fragment thereof, as defined above, comprises the heavy chain variable region having an amino acid sequence of SEQ ID NO: 54 and the light chain variable region having amino acid sequences of any one of SEQ ID NOs: 55, 57, 70 and 72.

In some embodiments, the monoclonal antibody, as defined above, is a full-length antibody, further comprising human antibody constant regions; preferably, the heavy chain constant region of the human antibody constant regions is selected from constant regions of human IgG1, IgG2, IgG3 and IgG4 and conventional variants thereof, and the light chain constant region of the human antibody constant regions is selected from κ and λ chain constant regions of human antibody and conventional variants thereof; preferably comprising a human antibody heavy chain constant region having an amino acid sequence of SEQ ID NO: 58, 60 or 65 and a human light chain constant region having an amino acid sequence of SEQ ID NO: 59.

In some embodiments, the monoclonal antibody, as defined above, is a full-length antibody, further comprising human antibody constant regions, which comprises a human antibody heavy chain constant region of SEQ ID NO: 58 and a human light chain constant region of SEQ ID NO: 59.

In some embodiments, the monoclonal antibody, as defined above, is a full-length antibody, further comprising human antibody constant regions, which comprises a human antibody heavy chain constant region of SEQ ID NO: 60 and a human light chain constant region of SEQ ID NO: 59.

In some embodiments, the monoclonal antibody, as defined above, is a full-length antibody, further comprising human antibody constant regions, which comprises a human antibody heavy chain constant region of SEQ ID NO: 65 and a human light chain constant region of SEQ ID NO: 59.

In some embodiments, the antigen-binding fragment is selected from the group consisting of Fab, Fab', F(ab')$_2$, single chain variable fragment (scFv), dimerized domain V (diabody), disulfide stabilized Fv (dsFv) and CDR-containing peptides.

In another aspect, the present disclosure provides a pharmaceutical composition comprising a therapeutically effective amount of the monoclonal antibody or the antigen-binding fragment thereof, as defined above, and one or more pharmaceutically acceptable carriers, diluents or excipients; preferably, the therapeutically effective amount of the monoclonal antibody or antigen-binding fragment thereof is a unit dose of 0.1-3000 mg/kg of the monoclonal antibody or the antigen-binding fragment thereof, as defined above.

In some aspects, the present disclosure provides a nucleic acid molecule encoding the monoclonal antibody or the antigen-binding fragment thereof, as defined above.

In some aspects, the present disclosure provides a recombinant vector comprising the nucleic acid molecule, as defined above.

In some aspects, the present disclosure provides a host cell transformed with the recombinant vector, as defined above, wherein the host cell is selected from a prokaryotic cell and a eukaryotic cell, preferably a eukaryotic cell, more preferably a mammalian cell.

In some aspects, the present disclosure provides a method for producing the monoclonal antibody or the antigen-binding fragment thereof, as defined above, wherein the method comprises culturing the host cell, as defined above, in a medium to produce and accumulate the monoclonal antibody or the antigen-binding fragment thereof, as defined above, and harvesting the monoclonal antibody or the antigen-binding fragment thereof from the culture.

In some aspects, the present disclosure provides a method for immunodetection or determination of human PD-L1, wherein the method comprises using the monoclonal antibody or antigen-binding fragment thereof as defined above.

In some aspects, the present disclosure provides a use of the monoclonal antibody or antigen-binding fragment thereof, as defined above, in the preparation of a diagnostic agent for a human PD-L1-related disease.

In some aspects, the present disclosure provides a method for treating diseases associated with human PD-L1, wherein the method comprises administering to a subject a pharmaceutically effective amount of the monoclonal antibody or the antigen-binding fragment thereof, as defined above, or comprising the pharmaceutical composition, as defined above, or the nucleic acid molecule, as defined above, for treat diseases associated with human PD-L1, wherein the disease is preferably a tumor or a cancer; more preferably squamous cell carcinoma, myeloma, small cell lung cancer, non-small cell lung cancer (NSCLC), head and neck squamous cell carcinoma (HNSCC), glioma, Hodgkin's lymphoma, Non-Hodgkin's lymphoma, diffuse large B-cell lymphoma (DLBCL), follicular lymphoma, acute lymphoblastic leukemia (ALL), acute myeloid leukemia (AML), chronic lymphocytic leukemia (CLL), chronic myeloid leukemia (CML), primary mediastinal large B-cell lymphoma, mantle cell lymphoma (MCL), small lymphocytic lymphoma (SLL), T-cell/histocyte-rich large B-cell lymphoma, multiple myeloma, myeloid cell leukelia-1 protein (Mcl-1), myelosdysplastic syndrome (MDS), gastrointestinal (tract) cancer, renal cancer, ovarian cancer, liver cancer, lymphoblastic leukemia, leukemia, colorectal cancer, endometrial cancer, kidney cancer, prostate cancer, thyroid cancer, melanoma, chondrosarcoma, neuroblastoma, pancreatic cancer, glioblastoma multiforme, gastric carcinoma, bone cancer, Ewing's sarcoma, cervical cancer, brain cancer, gastric carcinoma bladder cancer, hepatocellular carcinoma, breast cancer, colon cancer, hepatocellular carcinoma, (HCC), clear cell renal cell carcinoma (RCC), head and neck cancer, throat cancer, hepatobiliary cancer, central nervous system cancer, esophageal cancer, malignant pleural mesothelioma, systemic light chain amyloidosis lymphoplasmacytic lymphoma, myelodysplastic syndrome, myeloproliferative tumor, neuroendocrine neoplasm, Merkel cell carcinoma, testicular cancer and skin cancer; most preferably a PD-L1-positive cell carcinoma myeloma, small cell lung cancer, non-small cell lung cancer (NSCLC), head and neck squamous cell carcinoma (HNSCC), glioma, Hodgkin's lymphoma, Non-Hodgkin's lymphoma, diffuse large B-cell lymphoma (DLBCL), follicular lymphoma, acute lymphoblastic leukemia (ALL), acute myeloid leukemia (AML), chronic lymphocytic leukemia (CLL), chronic myeloid leukemia (CML), primary mediastinal large B-cell lymphoma, mantle cell lymphoma (MCL), small lymphocytic lymphoma (SLL), T-cell/histocyte-rich large B-cell lymphoma, multiple myeloma, myeloid cell leukelia-1 protein (Mcl-1), myelodysplastic syndrome (MDS), gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, gastric carcinoma, bone cancer. Ewing's sarcoma, cervical cancer, brain cancer, gastric carcinoma, bladder cancer, hepatocellular carcinoma, breast cancer, colon cancer, hepatocellular carcinoma (HCC), clear cell renal cell carcinoma (RCC), head and neck cancer, throat cancer, hepatobiliary cancer, central nervous system cancer, esophageal cancer, malignant pleural mesothelioma, systemic light chain amyloidosis, lymphoplasmacytic lymphoma, myelodysplastic syndrome, myeloproliferative tumor, neuroendocrine neoplasm, Merkel cell carcinoma, testicular cancer and skin cancer.

In some aspect, the present disclosure provides a use of the monoclonal antibody or the antigen-binding fragment thereof, as defined above, or comprising the pharmaceutical composition, as defined above, or comprising the nucleic acid molecule, as defined above, in the preparation of a therapeutic agent for disease associated with human PD-L1, wherein the disease is preferably a tumor or a cancer; more preferably squamous cell carcinoma, myeloma, small cell lung cancer, non-small cell lung cancer (NSCLC), head and neck squamous cell carcinoma (HNSCC), glioma, Hodgkin's lymphoma, Non-Hodgkin's lymphoma, diffuse large B-cell lymphoma (DLBCL), follicular lymphoma, acute lymphoblastic leukemia (ALL), acute myeloid leukemia (AML), chronic lymphocytic. leukemia (CLL), chronic myeloid leukemia (CML), primary mediastinal large B-cell lymphoma, mantle cell lymphoma (MCL), small lymphocytic lymphoma (SLL), T-cell/histocyte-rich large B-cell lymphoma, multiple myeloma, myeloid cell leukelia-1 protein (Mcl-1), myelodysplastic syndrome (MDS), gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, gastric carcinoma, bone cancer, Ewing's sarcoma, cervical cancer, brain cancer, gastric carcinoma, bladder cancer, hepatocellular carcinoma, breast cancer, colon cancer, hepatocellular carcinoma (HCC) clear cell renal cell carcinoma (RCC), head and neck cancer, throat cancer, hepatobiliary cancer, central nervous system cancer, esophageal cancer, malignant pleural mesothelioma, systemic light chain amyloidosis, lymphoplasmacytic lymphoma, myelodysplastic syndrome, myeloproliferative tumor, neuroendocrine neoplasm, Merkel cell carcinoma, testicular cancer and skin cancer; most preferably a PD-L1-positive cell carcinoma, myeloma, small cell lung cancer, non-small cell lung cancer (NSCLC), head and neck squamous cell carcinoma (HNSCC). glioma, Hodgkin's lymphoma, Non-Hodgkin's lymphoma, diffuse large B-cell lymphoma (DLBCL), follicular lymphoma, acute lymphoblastic leukemia (ALL), acute myeloid leukemia (AML), chronic lymphocytic leukemia (CLL), chronic myeloid leukemia (CML), primary mediastinal large B-cell lymphoma, mantle cell lymphoma (MCL), small lymphocytic lymphoma (SLL), T-cell/histocyte-rich large B-cell lymphoma, multiple myeloma, myeloid cell leukelia myelodysplastic syndrome (MDS), gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, gastric carcinoma, bone cancer, Ewing's sarcoma, cervical cancer, brain cancer, gastric carcinoma, bladder cancer, hepatocellular carcinoma, breast cancer, colon cancer, hepatocellular carcinoma (HCC), clear cell renal cell carcinoma (RCC), head and neck cancer, throat cancer, hepatobiliary cancer, central nervous system cancer, esophageal cancer, malignant pleural mesothelioma, systemic light chain amyloidosis, lymphoplasmacytic lymphoma, myelodysplastic syndrome, myeloproliferative tumor, neuroendocrine neoplasm, Merkel cell carcinoma, testicular cancer and skin cancer.

A medicament of the monoclonal antibody or the antigen-binding fragment thereof, as defined above, or comprising the pharmaceutical composition, as defined above, or the nucleic acid molecule as defined above.

A medicament of the monoclonal antibody or the antigen-binding fragment thereof, as defined above, or comprising the pharmaceutical composition, as defined above, or the nucleic acid molecule, as defined above, wherein the medicament is used to treat a PD-L1-positive tumor or cancer; preferably, the cancer is selected from squamous cell carcinoma, myeloma, small cell lung cancer, non-small cell lung cancer (NSCLC), head and neck squamous cell carcinoma (HNSCC), glioma, Hodgkin's lymphoma, Non-Hodgkin's lymphoma, diffuse large B-cell lymphoma (DLBCL), follicular lymphoma, acute lymphoblastic leukemia (ALL), acute myeloid leukemia (AML), chrome lymphocytic leukemia (CLL), chronic myeloid leukemia (CML), primary mediastinal large B-cell lymphoma, mantle cell lymphoma (MCL), small lymphocytic lymphoma (SLL), T-cell/histocyte-rich large B-cell lymphoma, multiple myeloma, myeloid cell leukelia -1 protein (Mcl-1), myelodysplastic syndrome (MDS), gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, gastric carcinoma, bone cancer, Ewing's sarcoma, cervical cancer, brain cancer, gastric carcinoma, bladder cancer, hepatocellular carcinoma, breast cancer, colon cancer, hepatocellular carcinoma (HCC), clear cell renal cell carcinoma (RCC), head and neck cancer, throat cancer, hepatobiliary cancer, central nervous system cancer, esophageal cancer, malignant pleural mesothelioma, systemic light chain amyloidosis, lymphoplasmacytic lymphoma, myelodysplastic syndrome, myeloproliferative tumor, neuroendocrine neoplasm, Merkel cell carcinoma, testicular cancer and skin cancer.

BRIEF DESCRIPTION OF THE DRAWINGS

FIG. 2: ADCC effect comparison of IgG1 and IgG4 forms of different PD-L1 antibodies.

DETAILED DESCRIPTION OF THE PREFERRED EMBODIMENT

I. Terminology

Figure 1:
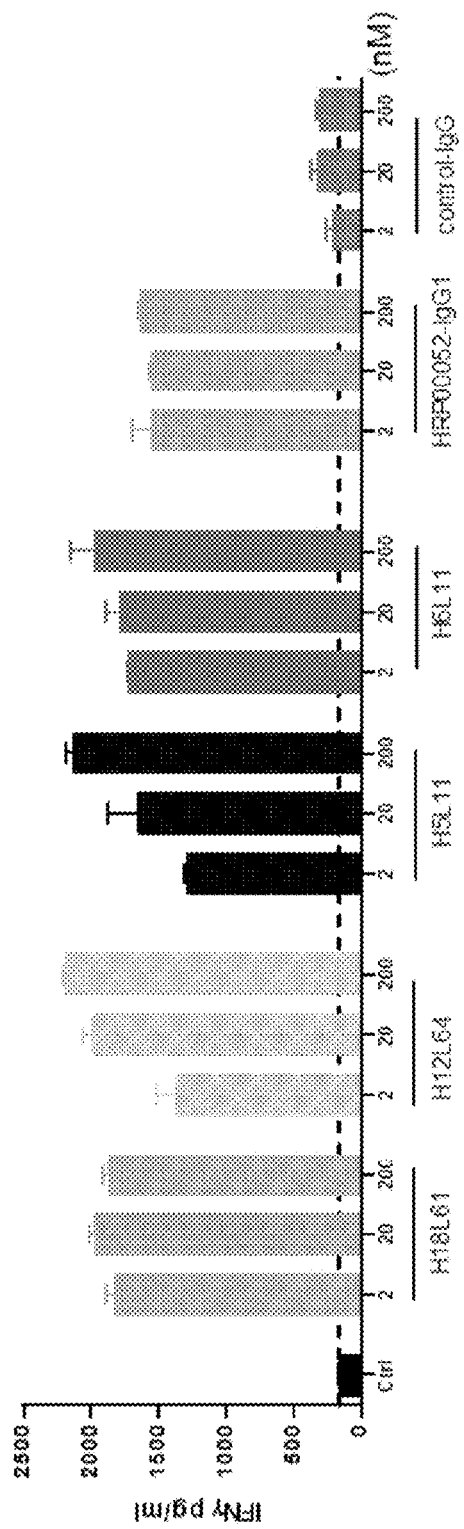
FIG. 1: PD-L1 antibody promotes IFNγ secretion of cells in PBMC-T lymphocyte activation assays.
Figure 2A:
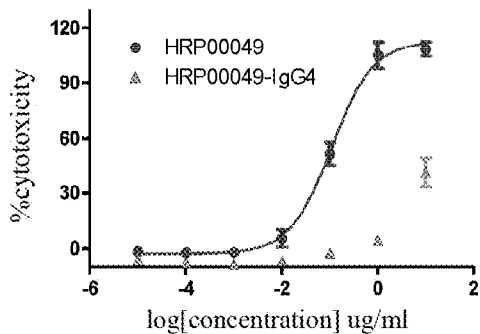
FIG. 2A is a comparison of IgG1 and IgG4 forms of HRP00049.
Figure 2B:
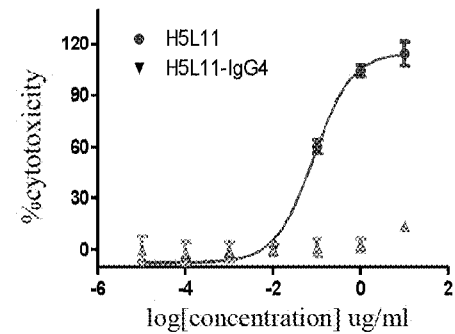
FIG. 2B is a comparison of IgG1 and IgG4 forms of H5L11.
Figure 2C:
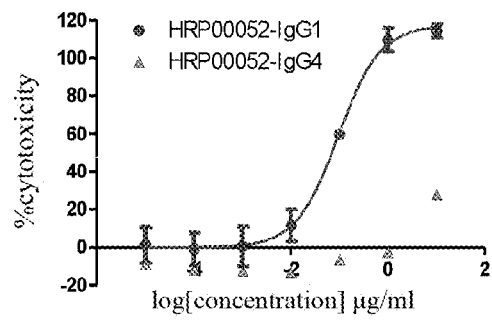
FIG. 2C is a comparison of IgG1 and IgG4 forms of HRP00052.
Figure 2D:
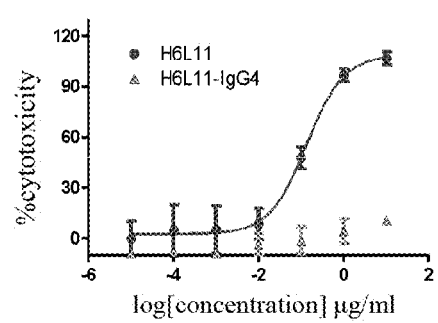
FIG. 2D is a comparison of IgG1 and IgG4 forms of H6L11.
Figure 2E:
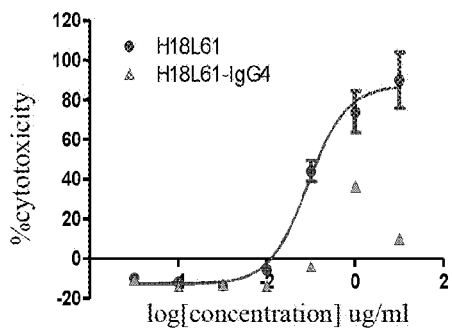
FIG. 2E is a comparison of IgG1 and IgG4 forms of H18L61.
Figure 2F:
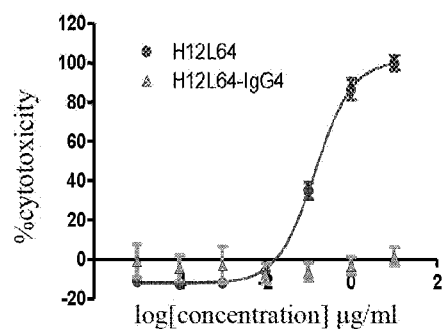
FIG. 2F is a comparison of the IgG1 and IgG4 forms of H12L64.

In order to better understand the present disclosure, certain technical and scientific terms are specifically defined below. Unless otherwise defined herein, all other technical and scientific terms used herein have the meaning commonly understood by those skilled in the art to which this invention belongs.

Three-letter codes and one-letter codes of amino acids used in the present disclosure are described in J. biol. chem, 243, p 3558(1968).

The "antibody" described in the present disclosure refers to an immunoglobulin, which is a tetrapeptide chain structure formed by connecting two identical heavy chains and two identical light chains through interchain disulfide bonds. The amino acid composition and arrangement order of the constant region of the immunoglobulin heavy chain are different, so their antigenicity is also different. According to this, immunoglobulins can be divided into five categories, or called isotypes of immunoglobulins, namely IgM, IgD, IgG, IgA and IgE, and the corresponding heavy chains are μ, δ, γ, α and ε chains, respectively. Same class of Igs can be divided into different subclasses according to the differences in amino acid composition of the hinge region and the number and position of heavy chain disulfide bonds. For example, IgG can be divided into IgG1, IgG2, IgG3, and IgG4. Light chain is divided into a kappa chain or a lambda chain by the difference of constant regions. Each of the five types of Ig can have a kappa chain or a lambda chain.

In the present disclosure, the antibody light chain described in the present disclosure may further include a light chain constant: region comprising human or murine κ, λ chain, or variants thereof.

In the present disclosure, the antibody heavy chain described in the present disclosure may further include a heavy chain constant region comprising human or murine IgG1, IgG2, IgG3, IgG4 or variants thereof.

The sequence of about 110 amino acids near the N-terminus of the heavy and light chains of the antibody varies greatly, so is called variable region (Fv region); the remaining amino acid sequences near the C-terminus are relatively stable, so it is called constant region. The variable region includes three hypervariable regions (HVR) and four relatively conserved framework regions (FR). The three hypervariable regions determine the specificity of the antibody, also known as complementarity determining regions (CDRs). Each light chain variable region (LCVR) and heavy chain variable region (HCVR) is composed of three CDR regions and four FR regions, which are sequentially arranged from the amino terminal to the carboxy terminal: FR1, CDR1, FR2, CDR2, FR3, CDR3, FR4. The three CDR regions of the light chain are referred to as LCDR1, LCDR2 and LCDR3; the three CDR regions of the heavy chain are referred to as HCDR1, HCDR2 and HCDR3. The number and position of CDR amino acid residues of the LCVR and HCVR of the antibody or the antigen-binding fragment described in the present disclosure conform to the known Kabat numbering rules (LCDR1-3, HCDR1-3).

Antibodies of the present disclosure include murine antibodies, chimeric antibodies, humanized antibodies, preferably humanized antibodies.

'Monoclonal antibody' refers to an antibody obtained from a population of substantially homogeneous antibodies, i.e., individual antibodies constituting the population are the same and/or bind to the same epi tope except for possible variant antibodies (e.g., containing naturally occurring mutations or mutations formed during the manufacture of monoclonal antibody preparations, and these variants are usually present in small amounts). Unlike polyclonal antibody preparations, which typically contain different antibodies targeting different determinants (epitopes), each monoclonal antibody of a monoclonal antibody preparation (formulation) is targeted to a single determinant on an antigen. Thus, the modifier 'monoclonal' indicates the properties of an antibody as obtained from a population of substantially homogeneous antibody and should not be construed as requiring the manufacture of antibody by an particular method. For example, the monoclonal antibody of the present disclosure can be prepared by various techniques including, but not limited to, hybridoma method, recombinant DNA method, phage display method, and method using transgenic animals containing all or part of human immunoglobulin loci, such kind of methods as well as other exemplary methods for preparing monoclonal antibodies are described herein.

The term 'murine antibody' in this disclosure is an anti-human PD-L1 monoclonal antibody prepared according to the knowledge and skill in the art. Test subjects are injected with PD-L1 antigen during preparation, and hybridomas expressing antibodies with the desired sequence or functional characteristics are isolated. In a preferred embodiment of the present disclosure, the anti-murine PD-L1 antibody or the antigen-binding fragment thereof may further comprise a light chain constant region comprising murine κ, λ chain or variants thereof, or further comprise a heavy chain constant region of murine IgG1, IgG2, IgG3 or variants thereof.

The term 'chimeric antibody' is an antibody obtained by fusing the variable region of a marine antibody with the constant region of a human antibody, which can reduce the immune response triggered by the murine antibody. To construct a chimeric antibody, the first thing is to establish a hybridoma that secrets murine specific monoclonal antibody, then clone the variable region gene from the murine hybridoma cell, and then clone the constant region gene of the human antibody as required. The murine variable region gene is linked with the human constant region gene to form a chimeric gene for subsequently inserting into an expression vector. Finally, the chimeric antibody molecule is expressed in a eukaryotic system or a prokaryotic system. In a preferred embodiment of the present disclosure, the antibody light chain of the PD-L1 chimeric antibody further comprises a light chain constant region comprising a human κ, λ chain or a variant thereof. The antibody heavy chain of the PD-L1 chimeric antibody further comprises a heavy chain constant region of human IgG1, IgG2, IgG3, IgG4 or a variant thereof, preferably a human IgG1, IgG2 or IgG4 heavy chain constant region, or a variant of IgG1, IgG2 or IgG4 with amino acid mutation (e.g., YTE mutation or back mutation).

The term 'humanized antibody', which is also called CDR-grafted antibody, refers to an antibody produced by grafting a murine CDR sequence into a framework of human antibody variable region, that is, an antibody produced from different type of human germline antibody framework sequences. it can avert the heterogeneous response triggered by the chimeric antibody which carries a large amount of murine protein components. Such framework sequences can be obtained from a public DNA database containing germline antibody gene sequences or published references. For example, germline DNA sequences of human heavy and light chain variable region genes can be obtained from the 'VBase' human germline sequence database (available on website: www.mrcepe.com.ac.uk/vbase), and in Kabat, E A. etc., 1991 Sequences of Proteins of Immunological Interest, 5th edition. In order to avoid the decrease in activity caused by the decrease in immunogenicity, the framework sequence of human antibody variable region may be subjected to minimal reverse mutation or back mutation to retain activity. The humanized antibodies of the present disclosure also include humanized antibodies with affinity maturation of CDRs by plume display. In a preferred embodiment of the present disclosure, the human antibody variable region framework is designed and selected, wherein the heavy chain FR sequence on the antibody heavy chain variable region is derived from the combined sequence of human germline heavy chain IGHV3-23*04 and hJH4.1, and the combined sequence of human germline light chain IGKV1-12*01 and hJK4.1. In order to avoid the decrease in activity caused by the decrease in immunogenicity, the human antibody variable region can be subjected to minimum reverse mutation (back mutation, that is, amino acid residues in FR from the human antibody is mutated to the amino acid residues in corresponding position of original antibody) to retain activity.

The grafting of CDRs may result in a decrease in the affinity of produced PD-L1 antibody or the antigen-binding fragment thereof to antigen due to the framework residues in contact with the antigen. Such interactions can be the result of highly mutated somatic cells. Therefore, it may still be necessary to graft such donor framework amino acids to the framework of a humanized antibody. Amino acid residues involved in antigen binding from non-human PD-L1 antibody or the antigen-binding fragment thereof can be identified by examining the sequence and structure of the variable region of murine monoclonal antibody. Residues in the CDR donor framework that differ from the germline can be considered related. If the closest germline cannot he determined, the sequence can be compared to the consensus sequence of subclass or the consensus sequence of murine sequence with a high percentage of similarity. Rare framework residues are believed to be the result of high frequency mutations of somatic cells, thus playing an important role in binding.

The term 'antigen-binding fragment' or 'functional fragment' of an antibody refers to one or more fragments of an antibody that retain the ability to specifically bind an antigen (e.g., PD-L1). It has been shown that fragments of a full-length antibody can be used to perform the antigen-binding function of the antibody. Examples of binding fragments indicated in the term 'antigen-binding fragment' of an antibody include (i) a Fab fragment, i.e., a monovalent fragment consisting VL, VH, CL and CH1 domains; (ii) a F(ab')$_2$ fragment, a bivalent fragment including two Fab fragments connected by disulfide bridge(s) in the hinge region, (iii) a Pd fragment consisting of VH and CH1 domains; (iv) a Fv fragment consisting of VH domain and VL domain of single-armed of the antibody; (v) a single domain or dAb fragment (Ward et al. (1989) Nature 341: 544-546) which is composed of a VH domain; and (vi) an isolated complementary determining region (CDR) or (vii) optionally a combination of two or more separate CDRs connected by a synthetic linker. In addition, although the two domains and VII of Fv fragment are encoded by separate genes, these genes can be combined through a synthetic linker using recombinant methods, thus producing a single protein chain that is a monovalent molecule formed by pairing VL and VH regions (referred to as single-chain Fv (scFv); see e.g., Bird et al. (1988) Science 242: 423-426; and Huston et al. (1988) Proc. Natl. Acad. Sci USA 85: 5879-5883). Such sews are also intended to be included in the term "antigen-binding fragment" of an antibody. Such antibody fragments are obtained using conventional techniques known to those skilled in the art and screened by their functionality in the same manner as intact antibodies. Antigen-binding moieties can be produced by recombinant DNA technology or by enzymatic or chemical cleavage of intact immunoglobulins. The antibodies may be antibodies of different isotypes, for example. IgG (e.g., IgG1, IgG2, IgG3 or IgG4 subtypes), IgA1, IgA2, IgD, IgE or IgM antibodies.

The antigen-binding fragments of the present disclosure include Fab, F(ab')$_2$, Fab', single chain variable fragment (scFv), dimerized domain V (diabody), disulfide stabilized Fv (dsFv). CDR-containing peptides. etc.

Fab is an antibody fragment having a molecular weight of about 50,000 obtained by treating IgG antibody molecule with a protease such as papain (cleaves the amino acid residue at position 224 of the H chain), which has antigen-binding activity of the fragments, wherein about half of the N-terminal side of the H chain and the entire L chain are connected together by disulfide bonds.

Fab or the present disclosure can be produced by treating the monoclonal antibody of the present disclosure that specifically recognizes and binds to the amino acid sequence of the extracellular region of human PD-L1 or its three-dimensional structure with papain. In addition, the Fab can be produced by inserting DNA encoding the Fab of the antibody into a prokaryotic expression vector or a eukaryotic expression vector and transforming the vector into a prokaryote or eukaryote to express the Fab.

F(ab')$_2$ is an antibody fragment having a molecular weight of about 100,000 by cleaving the lower portions of two disulfide bonds in IgG hinge region with enzyme pepsin, which has antigen-binding activity and two Fab regions connected at hinge positions.

F(ab')$_2$ of the present disclosure can be produced by treating the monoclonal antibody of the present disclosure that specifically recognizes and binds to the amino acid sequence of the extracellular region of human PD-L1 or its three-dimensional structure with pepsin. In addition, the F(ab')$_2$ can be produced by connecting Fab's described below with thioether bond(s) or disulfide bond(s).

Fab' is an antibody fragment having a molecular weight of about 50,000 obtained by cleaving the disulfide bond of the hinge region of F(ab')2 described above, which has antigen-binding activity. The Fab' of the present disclosure can be produced by treating F(ab')2 of the present disclosure that specifically recognizes and binds, to the amino acid sequence of the extracellular region of PD-L1 or its three-dimensional structure with a reducing agent such as dithiothreitol.

In addition, Fab can be produced by inserting DNA encoding Fab' fragment of the antibody into a prokaryotic expression vector or a eukaryotic expression vector and transforming the vector into a prokaryote or eukaryote to express the Fab'.

The term 'single-chain variable fragment', 'single-chain Fv' or 'scFv' refers to the molecule including an antibody heavy chain variable domain (or region: VH) and an antibody light chain variable domain (or region; VL) conjugated by a linker. Such scFv molecules may have a general structure: NH$_2$-VL-linker-VH-COOH or NH$_2$-VH-linker-VL-COOH Suitable linkers of prior arts consist of repeated GGGGS amino acid sequences or variants thereof, for example using 1-4 repeated variants (Holliger et at (1993), Proc. Natl. Acad. Sci. USA90:6444-6448), Other linkers can be used for the present disclosure are described by Alfthan et al. (1995), Protein Eng.8:725-731, Choi et al. (2001), Eur.J.Immuno 1.31:94-106, Hu et al. (1996), Cancer Res.56: 3055.-3061, Kipriyanov et al. (1999), J. Mol. Biol. 293:41-56 and Roovers et al. (2001), Cancer Immunol.

The scFv of the present disclosure can be produced using the following steps: obtaining the cDNA encoding VH and VL of monoclonal antibody of the present disclosure that specifically recognizes and binds to the amino acid sequence of the extracellular region of human PD-L1 or its three-dimensional structure, and constructing the DNA encoding scFv, inserting the DNA into a prokaryotic or eukaryotic expression vector, and then transforming the expression vector into a prokaryote or eukaryote to express the scFv.

Diabody is an antibody fragment in which scFv is dimerized and possess bivalent antigen-binding activity. Two antigens in a bivalent antigen-binding activity may be the same or different.

Diabody of the present disclosure can be produced using the following steps: obtaining the cDNA encoding VH and VL of the monoclonal antibody of the present disclosure that specifically recognizes and binds to the amino acid sequence of the extracellular region human of PD-L1 or its three-dimensional structure, and constructing the DNA encoding scFv so that the length of the amino acid sequence of the peptide linker is 8 residues or less, inserting the DNA into a prokaryotic or eukaryotic expression vector, and then transforming the expression vector into a prokaryote or eukaryote to express the diabody.

dsFv is obtained by linking a polypeptide in which one amino acid residue in each of VH and VL is substituted by a cysteine residue via disulfide bond between the cysteine residues. The amino acid residues substituted by cysteine residues can be selected according to a known method (Protein Engineering, 7,697(1994) based on the three-dimensional structure prediction of the antibody.

dsFv of the present disclosure can be produced using the following steps: obtaining the cDNA encoding VH and VL of the monoclonal antibody of the present disclosure that specifically recognizes and hinds to the amino acid sequence of the extracellular region of human PD-L1 or its three-dimensional structure, and constructing DNA encoding dsFv, inserting the DNA into a prokaryotic or eukaryotic expression vector, and then transforming the expression vector into a prokaryote or eukaryote to express the dsFv.

A CDR-containing peptide comprises one or more CDRs derived from VH or VL. A multiple CDRs containing peptide can be conjugated directly or via a suitable peptide linker.

CDR-containing peptides of the present disclosure can be produced using the following steps: constructing DNA encoding CDRs derived from VH and VL of the monoclonal antibody of the present disclosure that specifically recognizes and binds to the amino acid sequence of the extracellular region of human PD-L1 or its three-dimensional structure, inserting the DNA into a prokaryotic or eukaryotic expression vector, and then transforming the expression vector into a prokaryote or eukaryote to express the peptide. The CDR-containing peptide can also be produced by a chemical synthesis method such as the Fmoc method or the tBoc method.

The term 'CDR' refers to one of the six hypervariable regions in the variable domain of an antibody that primarily contributes to antigen binding. One of the most commonly used definitions of the 6 CDRs is provided by Kabat E. A. et al. ((1991) Sequences of proteins of immunological interest. NIH Publication 91-3242). As used herein, the Kabat definition of CDRs applies to CDR1, CDR2 and CDR3 (CDR L1, CDR L2, CDR L3 or L1, L2, L3) of the light chain variable domain, and CDR1, CDR2 and CDR3 (CDR H1, CDR H2, CDR H3 or H2, H3) of the heavy chain variable domain.

The term 'antibody framework', as used herein, refers to a part of variable domain VL or VH, which serves as a scaffold for the antigen-binding loop (CDR) of the variable domain. In essence, it is a variable domain without CDR.

The 'conventional variant' of the human antibody heavy chain constant region and the human antibody light chain constant region refers to variants of heavy chain constant region or light chain constant region derived from human that does not change the structure and function of the variable region of an antibody, which has been disclosed in the prior art. Exemplary variants comprise heavy chain constant re ion variants of IgG1, IgG2, IgG3 or IgG4 that undergo site-directed modification and amino acid substitution of the heavy chain constant region, specific substitution such as those known in the prior art: YTE mutations, L234A and/or L235A mutation, or S228P mutation, or a mutation to obtain a knob-into-hole structure (such that the antibody heavy chain will have a combination of knob-Fc and hole-Fc), or a combination of the above-mentioned mutants. These mutations have been confirmed to make the antibody have new properties, but do not change the function of the variable region of the antibody.

The term 'epitope' or 'antigenic determinant' refers to a part on an antigen to which an immunoglobulin or antibody specifically binds (e.g., certain parts on PD-L1 molecule). An epitope typically includes at least 3, 4, 5, 6, 7, 8, 9, 10, 11, 12, 13, 14 or 15 consecutive or non-consecutive amino acids in a unique spatial conformation. See, for example, Epitope Mapping Protocols in Methods in Molecular Biology, vol. 66, G. E. Morris, Ed. (1996).

The terms 'specifically bind', 'selectively bind', 'bind selectively' and 'bind specifically' refer to the binding of an antibody to epitopes on a predetermined antigen. Generally, antibodies bind antigens with an affinity (KD) of less than about $10^{-8}$ M, such as about less than $10^{-9}$ M, $10^{-10}$ M, $10^{-11}$ M, or less.

The term 'KD' or 'Kd' refers to the dissociation equilibrium constant of a specific antibody-antigen interaction. Generally, antibodies of the present disclosure bind PD-L1 with a dissociation equilibrium constant (KD) of less than about $10^{-7}$ M, such as less than about $10^{-8}$ M, $10^{-9}$ M, or $10^{-10}$ M or less, for example, as measured by a BIACORE instrument using surface plasmon resonance (SPR) technology.

When the term 'competition' is used in the case of antigen-binding proteins competing for the same epitope (such as neutralizing antigen-binding proteins or neutralizing antibodies), it means competition between the antigen-binding proteins, which is determined by the following assay: In the assay, the antigen-binding protein (e.g., an antibody or an immunologically functional fragment thereof) to be tested prevents or inhibits (e.g., reduces) the binding of a reference antigen-binding protein (e.g., a ligand or reference antibody) to a common antigen (e.g., a PD-L1 antigen or a fragment thereof). Numerous types of competitive binding assays can be used to determine whether one antigen-binding protein competes with another, such as: solid-phase direct or indirect radioimmunoassay (RIA), solid-phase direct or indirect enzyme immunoassay (EIA), sandwich competition assay (see, e.g., Stahli et al., 1983, Methodsin Enzymology 9:242-253); solid phase direct biotin-avidin EIA (see, e.g., Kirkland et al., 1986, J. Immunol. 137:3614-3619), solid phase direct labeling assay, solid phase direct labeling sandwich assay (see, e.g., Harlow and Lane, 1988. (Antibodies, A Laboratory Manual), Cold Spring Harbor Press); solid phase direct labeling RIA using 1-125 (see. for example, Morel et al., 1988, Molec. Immunol.25:7-15); solid phase direct biotin-avidin EIA (see, for example, Cheung, et al., 1990, Virology176:546-552); and direct labeling RIA (Moldenhauer et al., 1990, Scand.J.Immunol.32:77-82). Generally, the assay involves the use of purified antigen bound to a solid surface or cell that bearing either the unlabeled detection antigen-binding protein or the labeled reference antigen-binding protein. Competitive inhibition is measured by measuring the number of labels that bind to a solid surface or cell in the presence of the antigen-binding protein tested. Usually, there is am excess of tested antigen-binding proteins. Antigen-binding proteins identified by competitive assay (competitive antigen-binding protein) include: an antigen-binding protein that binds to the same epitope as the reference antigen-binding protein; and an antigen-binding protein that binds adjacent epitope sufficiently dose to the binding epitope of the reference antigen-binding protein, while the two epitopes spatially hinder the binding of each other. Additional details regarding the methods used to determine competitive bindings are provided in the embodiments herein. Usually, when there is an excess of competing antigen-binding proteins, it will inhibit (e.g., reduce) at least 40-45%, 45-50%, 50-55%, 55-60%, 60-65%, 65-70%, 70-75% or 75% or more of the specific binding of the reference antigen binding protein to the common antigen. In some cases, binding is inhibited by at least 80-85%, 85-90%, 90-95%, 95-97% or 97%, or more.

The term 'nucleic acid molecule', as used herein, refers to both DNA molecules and RNA molecules. The nucleic acid molecule may be single-stranded or double-stranded, preferably double-stranded DNA. A nucleic acid is 'effectively linked' when it is placed in a functional relationship with another nucleic acid sequence. For example, if a promoter or enhancer affects transcription of a coding sequence, the promoter or enhancer is effectively linked to the coding sequence.

The term 'vector' refers to a nucleic acid molecule capable of transporting another nucleic acid to which it has been linked. In one embodiment, the vector is a 'plasmid', which refers to a circular double-stranded DNA loop to which other DNA segments can be linked. In another embodiment, the vector is a viral vector, wherein other DNA segments can be linked into the viral genome. The vectors disclosed herein are capable of autonomous replication in host cells into which they have been introduced (e.g., bacterial vectors with bacterial origins of replication and episomal mammalian vectors) or can be integrated into the host cell's genome after transfecting into the host cell, thereby replicating together with the host genome (e.g., non-episomal mammalian vectors).

Methods for producing and purifying antibodies and antigen-binding fragments are well known in the prior art, such as Chapters 5-8 and 15, Using Antibodies: A Laboratory Manual published by Cold Spring Harbor. For example, mice can be immunized with human PD-L1 or fragments thereof, and the resulting antibodies can be renatured, purified, and the amino acid can be sequenced using conventional methods. Antigen-binding fragments can also be prepared by conventional methods. The antibody or the antigen-binding fragment, as defined in the invention, is genetically engineered to add one or more human FR regions into a non-human CDR region. The human FR germline sequence can be obtained by aligning the IMGT human antibody variable region germline gene database and MOE software from ImMunoGeneTics (IMGT) website http://imgt.cines.fr, or from the Journal of Immunoglobulins, 2001ISBN012441351.

The term 'host cell' refers to a cell into which an expression vector has been introduced. Host cells may include bacteria, microorganism, plant or animal cells. Bacteria that are easy to be transformed include members of the Enterobacteriaceae, such as strains of *Escherichia coli* or *Salmonella; Bacilillaceae*, such as *Bacillus subtilis; Pneumococcus; Streptococcus* and *Haemophilus influenzae*. Suitable microorganisms include *Saccharomyces cerevisiae* and *Pichia pastoris*. Suitable animal host cell lines include CHO (Chinese Hamster Ovary Cell Line) and NS0 cells.

The engineered antibodies or the antigen-binding fragments of the present disclosure can be prepared and purified using conventional methods. For example, cDNA sequences encoding, heavy and light chains can be cloned and recombined into a GS expression vector. The recombinant immunoglobulin expression vector can be stably transfected into CHO cells. As a more recommended prior art, mammalian expression systems may cause glyeosylation of antibodies, especially in highly conserved N-terminal sites of Fc region. Stable clones are obtained by expressing antibodies that specifically bind to human PD-L1. Positive clones were expanded in serum-tree medium in the bioreactor to produce antibodies. The culture medium in which the antibody is secreted can be purified by conventional techniques, for example, an A or G Sepharose FE column with adjusted buffer. Non-specifically bound components are removed by washing. Then bound antibody was awed by pH gradient method, and antibody fragments were detected by SDS-PAGE and pooled. The antibody can be concentrated by filtration using a conventional method. Soluble mixtures and polymers can also be removed by conventional methods, such as molecular sieve or ion exchange. The resulting product needs to be immediately frozen, such as −70° C., or lyophilized.

When applied to an animal, human, experimental subject, cell, tissue, organ or biological fluid, 'administrate' and 'treat' refer to the contact of an exogenous drug, therapeutic agent, diagnostic agent or composition to animal, human, subject, cell, tissue, organ or biological fluid. 'Administrate' and 'treat' may refer to, for example, treatment, pharmacokinetics, diagnosis, research and experimental methods. Treatment of a cell includes contact of a reagent with a cell, and contact of a reagent with a fluid, wherein the fluid is in contact with the cell. 'Administrate' and 'treat' also mean treating such as cells in vitro and ex vivo by an agent, diagnosis, binding composition, or by another cell. When applied to a human, veterinary or research subject, 'treat' refers to therapeutic treatment, prevention or preventive measures, research and diagnostic applications.

'Therapy' means the administration of a therapeutic agent: for internal or external use, such as a composition comprising any of the binding compounds of the present disclosure, to a patient having one or a variety of disease symptoms for which the therapeutic agents are known to have therapeutic effect. Generally, a therapeutic agent is administered in an amount effectively alleviate one or more disease symptoms in a patient or population under treatment to induce the deterioration of such symptoms or inhibit the development of such symptoms to any clinically measurable degree. The amount of therapeutic agent (also referred to as 'therapeutically effective amount') that is effective in alleviating symptoms of any specific disease can vary depending on various factors, such as disease state, age and weight of the patient, and the ability of the drug to be effective as desired in the patient. Whether symptoms of the disease have been alleviated can be evaluated by any clinical test method that a doctor or other health care professional usually uses to assess the Severity or progression of the symptoms. Although embodiments of the present disclosure (e.g., treatment methods or articles) may not be effective in alleviating each symptom of target disease, they should alleviate symptoms of the target disease in a statistically significant number of patients confirmed by any statistical test method known in the art such as Student t-test, Chi-square test, Mann and Whitney's The U test, Kruskal-Wallis test (H test), Jonckheere-Terpstra test and Wilcoxon test.

'Conservative modification' or 'conservative substitution or replacement' refers to substituting amino acids of protein with other amino acids having similar characteristics (such as charge, side chain size, hydrophobicity/hydrophilicity, main chain conformation and rigidity, etc.), so that changes can be frequently made without changing the biological activity of the protein. Those skilled in the art recognize that, in general, single amino acid substitutions in non-essential regions of polypeptide do not substantially alter biological activity (see, e.g., Watson et al. (1987) Molecular Biology of the Gene. The Benjamin/Cummings Pub. Co., P224 (4th edition it. In addition, the substitution of structurally or functionally similar amino acid is unlikely to disrupt the biological activity.

An 'effective amount' includes an amount sufficient to ameliorate or prevent the symptoms or conditions of a medical disease. An effective amount also means an amount sufficient to allow or facilitate diagnosis. The effective amount for a particular patient or veterinary subject can vary depending on factors such as the condition to be treated, the overall health of patient, the route and dosage of administration, and the severity of side effects. The effective amount can be the maximum dose or dosage regimen to avert significant side effects or toxic effects.

'Exogenous' refers to a substance that is produced outside the organism, cell or human body as appropriate. 'Endogenous' refers to a substance that is produced in a cell, organism or human body as appropriate.

'Homology' refers to sequence similarity between two polynucleotide sequences or between two polypeptides. When positions in two compared sequences are occupied by same bases or amino acid monomer subunits, for example, if each position of two DNA molecules is occupied by adenine, then the molecules are homologous at that position. The percent of homology between two sequences is a function of the number of matching or homologous positions shared by the two sequences divided by the number of compared positions×100. For example, when the sequences are optimally compared, if 6 of 10 positions in the two sequences match or are homologous, then the two sequences are 60% homologous; if 95 of 100 positions in the two sequences match or are homologous, then the two sequences are 95% homologous. In general, comparisons are made when the two sequences are compared for the greatest percentage of homology.

As used herein, the terms 'cell', 'cell line' and 'cell culture' are used interchangeably, and all such names include their offspring. Thus, the words 'transformants' and 'transformed cells' include primary test cells and cultures derived therefrom regardless of the number of passages. It should also be understood that due to intentional or unintentional mutations, all offspring cannot have the exactly same DNA content. The mutant offspring that have the same functional or biological activity as those screened originally in the transformed cells are included. Where different names are meant, the meaning of which are clearly understood from the context.

As used herein, 'polymerase chain reaction' or 'PCR' refers to a procedure or technique in which a specific amount of nucleic acid, RNA and/or DNA is amplified as described, for example, in U.S. Pat. No. 4,683,195. Generally, it is necessary to obtain sequence information from the terminal of or outside the target region so that oligonucleotide primers that are identical or similar in sequence to the corresponding strands of the template to be amplified can be designed. The 5' terminal nucleotides of the two primers may coincide with the terminal of the material to be amplified, PCR, can be used to amplify specific RNA sequences, specific DNA sequences derived from total genomic DNA and cDNA, phage or plasmid sequences transcribed from total cellular RNA. See generally Mullis et, al. (1987) Cold Spring Harbor Symp. Ouant. Biol. 51:263; Edited by Erlich, (1989) POE. TECHNOLOGY (Stockton Press, N.Y.), PCR used herein is considered as one but not the only example of a nucleic acid polymerase reaction method for amplifying the test sample of nucleic acid, including the use of known nucleic acids as primers and nucleic acid polymerases to amplify or produce specific portions of nucleic acids.

'Optional' or 'optionally' means that the event or environment described later may, but need not, occur, and the description includes occasions where the event or environment occurs or does not occur. For example, 'optionally comprising 1-3 antibody heavy chain variable regions' means that an antibody heavy chain variable region of a specific sequence may, but need not, be present.

'Pharmaceutical composition' means a mixture containing one or more compounds or a physiological/pharmaceutically acceptable salt or prodrug thereof described herein with other chemical components, such as physiological/pharmaceutically acceptable carriers and excipients. The purpose of the pharmaceutical composition is to promote the administration to the organism, thus facilitating the absorption of the active ingredient and exerting the biological activity.

In addition, the present disclosure includes a medicament for treating a disease associated with PD-L1-positive cells, comprising a monoclonal antibody or an antibody fragment thereof of the present disclosure as an active ingredient.

There is no limitation on the diseases associated with PD-L1, as long as it is diseases associated with PD-L1, for example, the therapeutic response induced by the molecules disclosed in the present disclosure includes binding to human PD-L1 and then blocking the binding of PD-L1 to its ligand PD-1 and B7-1, or killing tumor cells that overexpress PD-L1. Therefore, the molecules of the present disclosure are very useful for those who suffer a tumor or a cancer, preferably melanoma, colon cancer, breast cancer, lung cancer, gastric carcinoma, intestinal cancer, renal cancer, non-small cell lung cancer, bladder cancer, etc., when in preparations and formulations suitable for therapeutic applications.

Further, the present disclosure relates to a method for immunodetection or determination of PD-L1, a reagent for immunodetection or determination of PD-L1, a method for immunodetection or determination of cells expressing PD-L1, and a diagnostic agent for diagnosing diseases associated with PD-L1-positive cells, which comprises the monoclonal antibody or the antibody fragment that specifically recognizes human PD-L1 and binds to the amino acid sequence of the extracellular region or the three-dimensional structure thereof as an active ingredient.

In the present disclosure, the method for detecting or determining the amount of PD-L1 may be any known method. For example, it includes immunological detection or measurement method.

The immunodetection or determination method is a method for detecting or determining the amount of antibody or antigen using a labeled antigen or antibody. Examples of the immunodetection or determination method include radioimmunoassay using radioimmunoassay (RIA), enzyme immunoassay (EIA or ELISA), fluorescent immunoassay (FIA), luminescent immunoassay, western blotting, physicochemical method, etc.

The above-mentioned diseases associated with PD-L1-positive cells can be diagnosed by detecting or measuring cells expressing PD-L1 with the monoclonal antibodies or the antibody fragments thereof of the present disclosure.

In order to detect cells expressing a polypeptide, a known immunodetection method, preferably an immunoprecipitation method, a fluorescent cell staining method, an immunohistochemistry method, and the like can be used. In addition, a fluorescent antibody staining method using the FMAT8100HTS system (Applied Biosystem) can be used.

In the present disclosure, there is no particular restriction on the living sample for detecting or measuring PD-L1, as long as it has the possibility of including cells expressing PD-L1, such as tissue cells, blood, plasma, serum, pancreatic juice, urine, feces, tissue fluid or culture fluid.

The diagnostic agent containing the monoclonal antibody or the antibody fragment thereof of the present disclosure may further contain a reagent for performing an antigen-antibody reaction or a reagent for testing the reaction according to diagnostic method as required. Reagents for performing the antigen-antibody reaction include buffers, salts and the like. Reagents for detection include reagents commonly used in immunodetection or determination methods, such as a labeled second antibody that recognizes the monoclonal antibody, the antibody fragment thereof or conjugate thereof and a substrate corresponding to the label, and the like.

Through modification, PD-L1 antibodies with higher affinity, stronger tumor killing activity and lower immunogenicity are obtained in the present disclosure.

II. Embodiments and Test Examples

The disclosure is further described below with reference to the embodiments, but these embodiments are not intended to limit the scope of the disclosure. Experimental methods without specifying certain conditions in lite embodiments of the present disclosure are generally in accordance with the conventional conditions, such as Using Antibodies: A Laboratory Manual, and Molecular Cloning: A Laboratory Manual, Cold Spring Harbor: or the conditions proposed by the manufacturers of raw materials or commodities. Reagents are commercially available conventional reagents unless otherwise specified.

Embodiment 1

Construction of Affinity Matured Yeast Library of PD-L1 Antibody and Validation of the Library In order to obtain belter anti-human PD-L1 antibodies, an affinity matured yeast library of scFv antibodies, from which new human PD-L1 antibodies were screened, was designed and prepared based on HRP00052 and HRP00049 antibodies Sequences of the CDRs, the light chain variable regions and the heavy chain variable regions of HRP00052 and HRP00049 are all derived from WO2017084495A1. The specific sequences are as follows:

HRP00049: 9-2 (H2/L10) IgG4(AA)(S228P)

Heavy chain: HRP00049 antibody heavy chain sequence:
(SEQ ID NO: 1)
QVQLQESGPGLVKPSQTLSLTCTVSGGSISNDYWTWIRQHPGKGLEYIGY

ISYTGSTYYNPSLKSRVTISRDTSKNQFSLKLSSVTAADTAVYYCARSGG

WLAPFDYWGRGTLVTVSSASTKGPSVFPLAPCSRSTSESTAALGCLVKDY

FPEPVTVSWNSGALTSGVHTFPAVLQSSGLYSISSVVTVPSSSLGTKTYT

CNVDHKPSNTKVDKRVESKYGPPCPPCPAPEAAGGPSVFLFPPKPKDTLM

ISRTPEVTCVVVDVSQEDPIEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWENGQPENNYKTTPPVLDSDG

SFFLYSRLTVDKSRWQEGNVFSCSVMHEALHNHYTQKSLSLSLGK

The gene sequence encoding HRP00049 antibody heavy chain:
(SEQ ID NO: 2)
CAGGTGCAACTGCAGGAGAGCGGCCCCGGACTCGTGAAACCCTCCCAGAC

CCTGAGCCTGACCTGTACCGTGAGCGGCGGCAGCATCAGCAACGACTACT

GGACTTGATCAGGCAGCACCCCGGCAAAGGCCTGGAGTACATCGGCTACA

TCAGCTACACCGGCTCCACCTACTACAACCCCAGCCTGAAGTCCAGGGTG

ACCATCAGCCGGGACACCAGCAAGAACCAGTTCAGCCTGAAGCTGAGCAG

CGTGACCGCTGCCGACACAGCCGTGTACTATTGTGCCAGAAGCGGCGGAT

GGCTGGCCCCTTTCGACTACTGGGGCAGAGGCACCCTGGTGACCGTGAGC

AGCGCTTCCACCAAGGGCCCATCGGTCTTCCCCCTGGCGCCCTGCTCCAG

GAGCACCTCCGAGAGCACAGCCGCCCTGGGCTGCCTGGTCAAGGACTACT

TCCCCGAACCGGTGACGGTGTCGTGGAACTCAGGCGCCCTGACCAGCGGC

GTGCACACCTTCCCGGCTGTCCTACAGTCCTCAGGACTCTACTCCCTCAG

CAGCGTGGTGACCGTGCCCTCCAGCAGCTTGGGCACGAAGACCTACACCT

GCAACGTAGATCACAAGCCCAGCAACACCAAGGTGGACAAGAGAGTTGAG

TCCAAATATGGTCCCCCATGCCCACCATGCCCAGCACCTGAGGCTGCTGG

GGGACCATCAGTCTTCCTGTTCCCCCCAAAACCCAAGGACACTCTCATGA

TCTCCCGGACCCCTGAGGTCACGTGCGTGGTGGTGGACGTGAGCCAGGAA

GACCCCGAGGTCCAGTTCAACTGGTACGTGGATGGCGTGGAGGTGCATAA

TGCCAAGACAAAGCCGCGGGAGGAGCAGTTCAACAGCACGTACCGTGTGG

TCAGCGTCCTCACCGTCCTGCACCAGGACTGGCTGAACGGCAAGGAGTAC

AAGTGCAAGGTCTCCAACAAAGGCFCCCGTCCTCCATCGAGAAAACCAT

CTCCAAAGCCAAAGGGCAGCCCCGAGAGCCACAGGTGTACACCCTGCCCC

CATCCCAGGAGGAGATGACCAAGAACCAGGTCAGCCTGACCTGCCTGGTC

AAAGGCTTCTACCCCAGCGACATCGCCGTGGAGTGGGAGAGCAATGGGCA

GCCGGAGAACAACTACAAGACCACGCCTCCCGTGCTGGACTCCGACGGCT

CCTTCTTCCTCTACAGCAGGCTCACCGTGGACAAGAGCAGGTGGCAGGAG

GGGAATGTCTTCTCATGCTCCGTGATGCATGAGGCTCTGCACAACCACTA

CACACAGAAGAGCCTCTCCCTGTCTCTGGGTAAATGA

Light chain: HRP00049 antibody light
chain sequence:
(SEQ ID NO: 3)
DIVMTQSPDSLAVSLGERATINCKSSQSLFYHSNQKHSLAWYQQKPGQPP

KLLIYGASTRESGVPDRFSGSGSGTDFTLTISSLOAEDVAVYYCOOYYGY

PYTFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVYAC

EVTHQGLSSPVTKSFNRGEC

The gene sequence encoding hRP00049 antibody
light chain:
(SEQ ID NO: 4)
GACATCGTGATGACCCAGAGCCCTGATAGCCTGGCTGTGAGCCTGGGCGA

GAGAGCCACCATCAACTGCAAGAGCAGCCAGAGCCTGTTCTACCATAGCA

ACCAGAAGCACAGCCTCGCCTGGTATCAGCAGAAGCCCGGCCAACCCCCC

AAGCTGCTGATCTACGGCGCCAGCACAAGAGAGAGCGGAGTGCCCGATAG

GTTCAGCGGCAGCGGATCCGGCACCGATTTCACCCTGACCATCAGCAGCC

TGCAGGCCGAGGATGTGGCCGTGTACTACTGCCAGCAGTACTACGGCTAC

CCTTACACCTTCGGCGGCGGCACCAAGGTGGAGATCAAGCGTACGGTGGC

TGCACCATCTGTCTTCATCTTCCCGCCATCTGATGAGCAGTTGAAATCTG

GAACTGCCTCTGTTGTGTGCCTGCTGAATAACTTCTATCCCAGAGAGGCC

AAAGTACAGTGGAAGGTGGATAACGCCCTCCAATCGGGTAACTCCCAGGA

GAGTGTCACAGAGCAGGACAGCAAGGACAGCACCTACAGCCTCAGCAGCA

CCCTGACGCTGAGCAAAGCAGACTACGAGAAACACAAAGTCTACGCCTGC

GAAGTCACCCATCAGGGCCTGAGCTCGCCCGTCACAAAGAGCTTCAACAG

GGGAGAGTGTTGA

HRP00052: 24D5(GF)IgG4(AA)(S228P)

Heavy chain: HRP00052 antibody heavy
chain sequence:
(SEQ ID NO: 5)
QVQLVQSGAEVKKPGASVKVSCKASGYTFTSYWMHWVRQAPGQGLEWMGR

IGPNSGFTSYNEKFKNRVTMTRDTSTSTVYMELSSLRSEDTAVYYCARGG

SSYDYFDYWGQGTTVTVSSASTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEAAGGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALENHYTQKSLSLSLGK

The gene sequence encoding HRP00052 antibody
heavy chain:
(SEQ ID NO: 6)
CAGGTGCAACTGGTGCAGAGCGGTGCCGAGGTGAAGAAGCCTGGCGCAAG

CGTGAAAGTGAGCTGCAAGGCCAGCGGCTACACCTTCACCAGCTACTGGA

TGCACTGGGTGAGGCAGGCCCCTGGACAGGGCCTGGAGTGGATGGGCAGG

ATCGGGCCCAACAGTGGTTTCACTAGCTACAATGAAAAGTTCAAGAACAG

GGTAACCATGACCAGGGACACCTCCACCAGCACAGTGTATATGGAGCTGA

GCAGCCTGAGGAGCGAGGACACCGCCGTGTACTACTGTGCCAGAGGCGGC

AGCAGCTACGACTACTTCGACTATTGGGGCCAGGGCACCACCGTGACCGT

GAGCAGTGCTTCCACCAAGGGCCCATCGGTCTTCCCCCTGGCGCCCTGCT

CCAGGAGCACCTCCGAGAGCACAGCCGCCCTGGGCTGCCTGGTCAAGGAC

TACTTCCCCGAACCGGTGACGGTGTCGTGGAACTCAGGCGCCCTGACCAG

CGGCGTGCACACCTTCCCGGCTGTCCTACAGTCCTCAGGACTCTACTCCC

TCAGCAGCGTGGTGACCGTGCCCTCCAGCAGCTTGGGCACGAAGACCTAC

ACCTGCAACGTAGATCACAAGCCCAGCAACACCAAGGTGGACAAGAGAGT

TGAGTCCAAATATGGTCCCCCATGCCCACCATGCCCAGCACCTGAGGCTG

CTGGGGGACCATCAGTCTTCCTGTTCCCCCCAAAACCCAAGGACACTCTC

ATGATCTCCCGGACCCCTGAGGTCACGTGCGTGGTGGTGGACGTGAGCCA

GGAAGACCCCGAGGTCCAGTTCAACTGGTACGTGGATGGCGTGGAGGTGC

ATAATGCCAAGACAAGCCGCGGGAGGAGCAGTTCAACAGCACGTACCGTG

TGGTCAGCGTCCTCACCGTCCTGCACCAGGACTGGCTGAACGGCAAGGAG

```
TACAAGTGCAAGGTCTCCAACAAAGGCCTCCCGTCCTCCATCGAGAAAAC

CATCTCCAAAGCAAAGGGCAGCCCCGAGAGCCACAGGTGTACACCCTGCC

CCCATCCCAGGAGGAGATGACCAAGAACCAGGTCAGCCTGACCTGCCTGG

TCAAAGGCTTCTACCCCAGCGACATCGCCGTGGAGTGGGAGAGCAATGGG

CAGCCGGAGAACAACTACAAGACCACGCCTCCCGTGCTGGACTCCGACGG

CTCCTTCTTCCTCTACAGCAGGCTCACCGTGGACAAGAGCAGGTGGCAGG

AGGGGAATGTCTTCTCATGHTCCGTGATGCATGAGGCTCTGCACAACCAC

TACACACAGAAGAGCCTCTCCCTGTCTCTGGGTAAATGA

Lightchain: HRP00052 antibody light
chain sequence:
                                          (SEQ ID NO:7)
DIVLTQSPASLAVSPGQRATITCRASESVSIHGTHLMHWYQQKPGQPPKL

LIYAASNLESGVPARFSGSGSGTDFTLTINPVEAEDTANYYCQQSFEDPL

TFGQGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

The gene sequence encoding HRP00052 antibody
light chain:
                                          (SEQ ID NO: 8)
GACATCGTGCTGACCCAGAGTCCCGCCTCACTTGCCGTGAGCCCCGGTCA

GAGGGCCACCATCACCTGTAGGGCCAGCGAGAGCGTGAGCATCCACGGCA

CCCACCTGATGCACTGGTATCAACAGAAACCCGGCCAGCCCCCAAACTG

CTGATCTACGCCGCCAGCAACCTGGAGAGCGGCGTGCCCGCCAGGTTCAG

CGGCTCCGGCAGCGGCACCGACTTCACCCTCACTATCAACCCCGTGGAGG

CCGAGGACACCGCCAACTACTACTGCCAGCAGAGCTTCGAGGACCCCCTG

ACCTTCGGCCAGGGCACCAAGCTGGAGATCAAGCGTACGGTGGCTGCACC

ATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTA

CAGTGGAAGGTGGAIAACGCCCTCCAATCGGIAACTCCCAGGAGAGTGT

CACAGAGCAGGACAGCAAGGACAGCACCTACAGCCTCAGCAGCACCCTGA

CGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGA

GTGTTGA
```

Underlined part in the above antibody sequence indicates variable region part of the antibody, and the other standardized form represents constant region part of the antibody.

Construction of yeast library: degenerate primers were designed, and the designed mutant amino acids were introduced into the libraries of HRP00049 and HRP00052 antibodies by PCR. Then, QC of the library was verified by the method of second-generation sequencing, in which seven antibody yeast libraries with a capacity of $10^9$ were constructed based on the HRP00049 and HRP00052 sequences.

Embodiment 2

Preparation of Antigen

Human PD-L1-IgG1Fc fusion protein was designed and synthesized, and purified with Protein A affinity column to obtain high-purity of recombinant PD-L1-Fc protein for detecting the binding of anti-PD-L1 antibody to antigen.

```
Human PD-L1-IgG1Fe:
                                          (SEQ ID NO: 9)
MEFGLSWLFLVAILKGVQCFTVTVPKDLYVVEYGSNMTIECKFPVEKQLDL

AALIVYWEMEDKNIIQFVHGEEHDLKVQHSSYRQRARLLKDQLSLGNAALQ

ITDVKLQDAGVYRCMISYGGADYKRITVKVNAPYNKINQRILVVDPVTSEH

ELTCQAEGYPKAEVIWTSSDHQVLSGKTTTTNSKREEKLFNVTSTLRINTT

TNEIFYCTFRRLDPEENHTAELVIPELPLAHPPNER*EPKSSDKTHTCPPCP*

*APELLGGPSVFLFPPKPKDTLMISTPEVTCVVVDVSHEDPEVKFNWYVD*

*GVEVHNAKTKPREEQYNSTYRVVSVLTVLHQDWLNGKEYKCKVSNKALP*

*APIEKTISKAKGQPREPQVYTLPPSRDELTKNQVSLTCLVKGFYSDLAVE*

*WESNGQPENNYKTTPPVLDSDGSFFLYSKLTVDKSRWQQGNVFSCSVMH*

*EALNHYTQKSLSLSPGK*
Note
signal peptide + extracellular domain + hIgG1Fc.
```

Embodiment 3

Screening of Antibodies

HRP00052 library used biotinylated human PD-L1-hIgG1Fc antigen and underwent two rounds of MACS screening (streptomycin magnetic heads. Invitrogen) and two rounds of FACS screening (BD FACSAria™ FUSION), Then about 400 yeast monoclonal cultures were selected and induced to express. FACS (BD FACSCanto II) was used to detect the binding of yeast monoclonal to human PD-L1-hIgG1Fc antigen, and yeast monoclonal with higher affinity than wild-type HRP00052 antibody were selected for sequence verification. After comparing and analyzing the sequenced clones and removing redundant sequences, non-redundant sequences were converted into full-length IgG (γ1, κ) for mammalian cell expression. The full-length antibodies after affinity purification were subjected to affinity determination using BIAcore™ X-100 (GE Life Sciences).

HRP00049 library used biotinylated human PD-L1-hIgG1Fc antigen and biotinylated mouse PD-L1-hIgG1Fc and underwent three rounds of MACS screening and three rounds of FACS screening. Then about 400 yeast monoclonal cultures were selected and induced to express. FACS was used to detect the binding of yeast monoclonal to human. PD-L1-hIgG1Fc antigen and mouse PD-L1-hIgG1Fc antigen, and yeast monoclonal that combines human PD-L1-hIgG1Fc antigen and mouse PD-L1-hIgG1Fc antigen was selected for sequence verification. After removing redundant sequences, non-redundant sequences were converted into full-length IgG (γ1, κ) for mammalian cell expression. The full-length antibodies after affinity purification were subjected to affinity determination using BIAcore™ X-100 (GE Life Sciences).

After screening, sequence of the antibody CDR region was selected.

Antibody from HRP00049 Mutant Library

The clones selected based on the sequences of HRP00049 mutant library are different from HRP00049 in HCDR1 and HCDR2. Related CDR sequences or general formulas and their corresponding heavy chain variable regions are described below.

HCDR1 is (SEQ ID NO: 10)
DGSAYWS or (SEQ ID NO: 11)
NDYWT

HCDR2

SEQ ID NO: 12
$X_1ISX_2AGSTYX_3TPSLKG$

HCDR3

SEQ ID NO: 13
SGGWLAPFDY

LCDR1

SEQ ID NO: 14
KSSQSLFYHSNQKHSLA

LCDR2

SEQ ID NO: 15
GASTRES

LCDR3

SEQ ID NO: 16
QQYYGYPYT

The general formula of related heavy chain variable region sequence is obtained as follows:

(SEQ ID NO: 17)
QVQLQESGPGLVKPSQTLSLTCTVSGGSISDGSAYWSWIRQHPGKGLEYG $X_1ISX_2AGSTYX_3TPSLKGRVTISRDTSKNQFSLKLSSVTAADTAVYYCA$

RSGGWLAPFDYWGRGTLVTVSS

Or (SEQ ID NO: 18)
QVQLQESGPGLVKPSQTLSLTCTVSGGSISNDYWTWIRQHPGKGLEYIG $X_1ISX_2AGSTYX_3TPSLKGRVTISRDTSKNQFSLKLSSVTAADTAVYYCA$

RSGGWLAPFDYWGRGTLVTVSS.

$X_1$ is selected from F or M, $X_2$ is selected from R or V, $X_3$ is selected from N or H in the above HCDR2 of SEQ ID NO. 12 and the heavy chain variable region of SEQ ID NO. 17 or 18.

Related light, chain variable region sequence was obtained as follows: (SEQ ID NO: 19) DIVMTQSPDSLAVSLGERATINCKSSQSLFYHSNQKHSLAWYQQKPGQPPKLLIYGASTRFSGVPDRFSGSGSGTDFTLTISSLQAEDVAVYYVQQYYGYPYTFGGGTKVEIK Antibody from HRP00052 Mutant Library The clones selected based on the sequences of HRP00052 mutant library are different from HRP00052 in HCDR1, HCDR2 and LCDR2. Related CDR sequences or general formulas and their corresponding heavy chain variable regions are described below.

HCDR1

SEQ ID NO: 20
$X_4X_5WMX_6$

HCDR2

SEQ ID NO: 21
$RIX_7PX_8X_9GX_{10}X_{11}X_{12}YNEKX_{13}KN$

HCDR3

SEQ ID NO: 22
GGSSYDYFDY

LCDR1

SEQ ID NO: 23
RASESVSIHGTHLMH

LCDR2

SEQ ID NO: 24
$X_{14}ASX_{15}X_{16}X_{17}S$

LCDR3

SEQ ID NO: 25
QQSFEDPLT

The general formula of related heavy chain variable region sequence is obtained as follows:

(SEQ ID NO: 26)
QVQLVQSGAEVKKPGASVKVSCKASGYTFTX$_4$X$_5$WMX$_6$WVRQAPGQGLEWM

GRIX$_7$PX$_8$X$_9$GX$_{10}$X$_{11}$X$_{12}$YNEKX$_{13}$KNRVTMTRDTSTSTVYMELSSLRSED

TAVYYCARGGSSYDYFDYWGQGTTVTVSS, in the above HCDR1 and HCDR2 of SEQ ID NO. 20 and 21 and the heavy chain variable region of SEQ ID NO. 26, $X_4$ is selected from S and D, $X_5$ is selected from Y and K, $X_6$ is selected from H and M, $X_7$ is selected from T, S, H and G, $X_8$ is selected from S, N and G, $X_9$ is selected from S, L and G, $X_{10}$ is selected from F, L, W and M, $X_{11}$ is selected from A, P and T, $X_{12}$ is selected from M, V, L and S, $X_{13}$ is selected from F and Y.

The general formula of related light chain variable region sequence is obtained as follows:

(SEQ ID NO: 27)
DIVLTQSPASLAVSPGQRATITCRASESVSIHGTHLMHWYQQKPGQPPKLL

IYX$_{14}$ASX$_{15}$X$_{16}$X$_{17}$SGVPARFSGSGSGTDFTLTINPVEAEDTANYYCQQSF

EDPLTFGQGTKLEIK, wherein $X_{14}$ is selected from V and A, $X_{15}$ is selected from Y and N, $X_{16}$ is selected from A, L and V, and $X_{17}$ is selected from E, F, Y and A (including that $X_{17}$ is selected from E, F and A and $X_{17}$ is selected from Y) in the LCDR2 SEQ ID NO: 24 and the light chain variable region of SEQ ID NO. 27. The specific related sequences obtained comprise but are not limited to those described in Table 1 and Table 2:

TABLE 1

Heavy chain variable region sequences determined by affinity screening

| Heavy chain variable region | VH sequence NO | Comprised HCDR1 sequence | Comprised HCDR2 sequence | Comprised HCDR3 sequence |
|---|---|---|---|---|
| 9-2 H5 | SEQ ID NO: 42 | DGSAYWS (SEQ ID NO: 10) | FISRAGSTYNTPSLKG (SEQ ID NO: 28) | SGGWLAPFDY (SEQ ID NO: 13) |
| 9-2 H6 | SEQ ID NO: 43 | NDYWT (SEQ ID NO: 11) | FISRAGSTYNTPSLKG (SEQ ID NO: 28) | SGGWLAPFDY (SEQ ID NO: 13) |
| 9-2 H7 | SEQ ID NO: 44 | NDYWT (SEQ ID NO: 11) | MISVAGSTYHTPSLKG (SEQ ID NO: 29) | SGGWLAPFDY (SEQ ID NO: 13) |
| 24D5 H12 | SEQ ID NO: 46 | SYWMH (SEQ ID NO: 30) | RITPSSGFAMYNEKFKN (SEQ ID NO: 32) | GGSSYDYFDY (SEQ ID NO: 22) |
| 24D5 H13 | SEQ ID NO: 47 | SYWMH (SEQ ID NO: 30) | RISPSLGLAVYNEKFKN (SEQ ID NO: 33) | GGSSYDYFDY (SEQ ID NO: 22) |
| 24D5 H14 | SEQ ID NO: 48 | SYWMH (SEQ ID NO: 30) | RIHPSLGLPLYNEKFKN (SEQ ID NO: 34) | GGSSYDYFDY (SEQ ID NO: 22) |
| 24D5 H15 | SEQ ID NO: 49 | DKWMM (SEQ ID NO: 31) | RITPSSGFAMYNEKFKN (SEQ ID NO: 32) | GGSSYDYFDY (SEQ ID NO: 22) |
| 24D5 H16 | SEQ ID NO: 50 | SYWMH (SEQ ID NO: 30) | RISPSLGLAVYNEKFKN (SEQ ID NO: 33) | GGSSYDYFDY (SEQ ID NO: 22) |
| 24D5 HI7 | SEQ ID NO: 51 | SYWMH (SEQ ID NO: 30) | RIGPNLGWAMYNEKYKN (SEQ ID NO: 35) | GGSSYDYFDY (SEQ ID NO: 22) |
| 24D5 H18 | SEQ ID NO: 52 | SYWMH (SEQ ID NO: 30) | RISPSSGMAVYNEKFKN (SEQ ID NO: 36) | GGSSYDYFDY (SEQ ID NO: 22) |
| 24D5 H19 | SEQ ID NO: 53 | SYWMH (SEQ ID NO: 30) | RISPGGGFTLYNEKFKN (SEQ ID NO: 37) | GGSSYDYFDY (SEQ ID NO: 22) |
| 24D5 H20 | SEQ ID NO: 54 | SYWMH (SEQ ID NO: 30) | RIGPNSGFTSYNEKFKN (SEQ ID NO: 38) | GGSSYDYFDY (SEQ ID NO: 22) |
| 24D5 H21 | SEQ ID NO: 66 | DKWMM (SEQ ID NO: 31) | RITPSSGFAMYNEKFKN (SEQ ID NO: 32) | GGSSYDYFDY (SEQ ID NO: 22) |

TABLE 2

Light chain variable region sequences determined by affinity screening

| Light chain variable region | VH sequence NO | Comprised LCDR1 sequence | Comprised LCDR2 sequence | Comprised LCDR3 sequence |
|---|---|---|---|---|
| 9-2 L11 | SEQ ID NO: 45 | KSSQSLFYHSNQKHSLA (SEQ ID NO: 14) | GASTRES (SEQ ID NO: 15) | QQYYGYPYT (SEQ ID NO: 16) |
| 24D5 L64 | SEQ ID NO: 55 | RASESVSIHGTHLMH (SEQ ID NO: 23) | VASYAAS (SEQ ID NO: 39) | QQSFEDPLT (SEQ ID NO: 25) |
| 24D5 L61 | SEQ ID NO: 56 | RASESVSIHGTHLMH (SEQ ID NO: 23) | AASNLES (SEQ ID NO: 40) | QQSFEDPLT (SEQ ID NO: 25) |
| 24D5 L66 | SEQ ID NO: 57 | RASESVSIHGTHLMH (SEQ ID NO: 23) | VASNVFS (SEQ ID NO: 41) | QQSFEDPLT (SEQ ID NO: 25) |
| 24D5 L67 | SEQ ID NO: 70 | RASESVSIHGTHLMH (SEQ ID NO: 23) | VASNVES (SEQ ID NO: 67) | QQSFEDPLT (SEQ ID NO: 25) |
| 24D5 L68 | SEQ ID NO: 71 | RASESVSIHGTHLMH (SEQ ID NO: 23) | VASNVWS (SEQ ID NO: 68) | QQSFEDPLT (SEQ ID NO: 25) |

TABLE 2-continued

Light chain variable region sequences determined by affinity screening

| Light chain variable region | VH sequence NO | Comprised LCDR1 sequence | Comprised LCDR2 sequence | Comprised LCDR3 sequence |
|---|---|---|---|---|
| 24D5 L69 | SEQ ID NO: 72 | RASESVSIHGTHLMH (SEQ ID NO: 23) | VASNVYS (SEQ ID NO: 69) | QQSFEDPLT (SEQ ID No: 25) |

Specific sequences of antibody light chain variable regions and heavy chain variable regions derived from HRP00049 antibody mutation library:

9-2 H5 heavy chain variable region
(SEQ ID NO: 42)
QVQLQESGPGLVKPSQTLSLTCTVSGGSISDGSAYWSWIRQHPGKGLEYIG

FISRAGSTNYTPSLKGRVTISRDTSKNQFSLKLSSVTAADTAVYYCARSGG

WLAPFDYWGRGTLVTVSS 9-2 H6 heavy chain variable region
(SEQ ID NO: 43)
QVQLQESGPGLVKPSQTLSLTCTVSGGSISNDYWTWIRQHPGKGLEYIGFI

SRAGSTYNTPSLKGRVTISRDTSKNQFSLKLSSVTAADTAVYYCARSGGWL

APFDYWGRGTLVTVSS 9-2 H7 heavy chain variable region
(SEQ ID NO: 44)
QVQLQESGPGLVKPSQTLSLTCTVSGGSISNDYWTWIRQHPGKGLEYIGMI

SVAGSTYHTPSLKGRVTISRDTSKNQFSLKLSSVTAADTAVYYCARSGGWL

APFDYWGRFTLVTVSS 9-2 L11 light chain variable region
(SEQ ID NO: 45)
DIVMTQSPDSLAVSLGERATINCKSSQSLFYHSNQKHSLAWYQQKPGQPPK

LLIYGASTRESGVPDRFSFSGSGTDFTLTISSLQAEDVAVYYCQQYYGYPY

TFGGGTKVEIK

Specific sequences of antibody light chain variable regions and heavy chain variable regions derived from HRP00052 antibody mutation library:

24D5 H12 heavy chain variable region
(SEQ ID NO: 46)
QVQLVQSGAEVKKPGASVKVSCKASGYTFTSYWMHWVRQAPGQGLEWMGRI

TPSSGFAMYNEKFKNRVTMTRDTSTSTVYMELSSLRSEDTAVYYCARGGSS

YDYFDYWGQGTTVTVSS

24D5 H13 heavy chain variable region
(SEQ ID NO: 47)
QVQLVQSGAEVKKPGASVKVSCKASGYTFTSYWMHWVRQAPGQGLEWMGRI

SPSLGLAVYNEKFKNRVTMTRDTSTSTVYMELSSLRSEDTAVYYCARGGSS

YDYFDYWGQGTTVTVSS

-continued

24D5 H14 heavy chain variable region
(SEQ ID NO: 48)
QVQLVQSGAEVKKPGASVKVSCKASGYTFTSYWMHWVRQAPGQGLEWMGRI

HPSLGLPVYNEKFKNRVTMTRDTSTSTVYMELSSLRSEDTAVYYCARGGSS

YDYFDYWGQGTTVTVSS

24D5 H15 heavy chain variable region
(SEQ ID NO: 49)
QVQLVQSGAEVKKPGASVKVSCKANGYTFTDKWMMWVRQAPGQGLEWMGRI

TPSSGFAMYNEKFKNRVTMTRDTSTSTVYMELSSLRSEDTAVYYCARGGSS

YDYFDYWGQGTTVTVSS

24D5 H16 heavy chain variable region
(SEQ ID NO: 50)
QVQLVQSGAEVKKPGASMKVSCKASGYTFTSYWMHWVRQAPGQGLEWMGRI

SPSLGLAVYNEKFKNRVTMTRDTSTSTVYMELSSLRSEDTAVYYCARGGSS

YDYFDYWGQGTTVTVSS

24D5 H17 heavy chain variable region
(SEQ ID NO: 51)
QVQLVQSGAEVKKPGASVKVSCKASGYTFTSYWMHWVRQAPGQGLEWMGRI

GPNLGWAMYNEKYKNRVTMTRDTSTSTVYMELSSLGSEDTAVYYCARGGSS

YDYFDYWGQTTVTVSS

24D5 H18 heavy chain variable region
(SEQ ID NO: 52)
QVQLVQSGAEVKKPGASVKVSCKASGYTFTSYWMHWVRQAPGQGLEWMGRI

SPSSGMAVYNEKFKNRVTMTRDTSTSTVYMELSSLRSEDTAVYYCARGGSS

YDYFDYWGQGTTVTVSS

24D5 H19 heavy chain variable region
(SEQ ID NO: 53)
QVQLVQSGAEVKKPGASVKVSCKASGYTFTSYWMHWVRQAPGQGLEWMGRI

SPGGGFTLYNEKFKNRVTMTRDTSTSTVYMELSSLRSEDTAVYYCARGGSS

YDYFDYWGQGTTVTVSS

24D5 H20 heavy chain variable region
(SEQ ID NO: 54)
QVQLVQSGAEVKKPGASVKVSCKASGYTFTSYWMHWVRQAPGQGLEWMGRI

GPNSGFTSYNEKFKNRVTMTRDTSTSTVYMELSSLRSEDTAVYYCARGGSS

YDYFDYWGQGTTVTVSS

24D5 H21 heavy chain variable region
(SEQ ID NO: 66)
QVQLVQSGAEVKKPGASVKVSCKASGYTFTDKWMMWVRQAPGQGLEWMGRI

TPSSGFAMYNEKFKNRVTMTRDTSTSTVYMELSSLRSEDTAVYYCARGGSS

YDYFDYWGQGTTVTVSS

24D5 L64 light chain variable region
(SEQ ID NO: 55)
DIVLTQSPASLAVSPGQRATITCRASESVSIHGTHLMHWYQQKPGQPPKLL

IYVASYAASGVPARFSGSGSGTDFTLTINPVEAEDTANYYCQQSFEDPLTF

GQGTKLEIK

24D5 L61 light chain variable region
(SEQ ID NO: 56)
DIVLTQSPASLAVSPGQRATITCRASESVSIHGTHLMHWYQQKPGQPPKLL

IYAASNLESGVPARFSGSGSGTDFTLTINPVEAEDTANYYCQQSFEDPLTF

GQGTKLEIK

24D5 L66 light chain variable region
(SEQ ID NO: 57)
DIVLTQSPASLAVSPGQRATITCRASESVSIHGTHLMHWYQQKPGQPPKLL

IYVASNVFSGVPARFSGSGSGTDFTLTINPVEAEDTANYYCQQSFEDPLTF

GQGTKLEIK

24D5 L67 light chain variable region
(SEQ ID NO: 70)
DIVLTQSPASLAVSPGQRATITCRASESVSIHGTHLMHWYQQKPGQPPKLL

IYVASNVESGVPARFSGSGSGTDFTLTINPVEAEDTANYYCQQSFEDPLTF

GQGTKLEIK

24D5 L68 light chain variable region
(SEQ ID NO: 71)
DIVLTQSPASLAVSPGQRATITCRASESVSIHGTHLMHWYQQKPGQPPKLL

IYVASNVWSGVPARFSGSGSGTDFTLTINPVEAEDTANYYCQQSFEDPLTF

GQGTKLEIK

24D5 L69 light chain variable region
(SEQ ID NO: 72)
DIVLTQSPASLAVSPGQRATITCRASESVSIHGTHLMHWYQQKPGQPPKLL

IYVASNVYSGVPARFSGSGSGTDFTLTINPVEAEDTANYYCQQSFEDPLTF

GQGTKLEIK

For the light chain variable regions and heavy chain variable regions of the above antibodies, the constant region of human heavy chain IgG1/light chain kappa is selected and combined with each heavy chain variable region and light chain variable region to form a complete antibody heavy chain and a complete antibody light chain. The sequences of the constant region and the light chain constant region are as follows:

IgG1 heavy chain constant region
(SEQ ID NO: 58)
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKGF

YPSDIAVEWESNGPENNYKTTPPVLDSDGSFFLYSKLTVDKSRWQQGNVFS

CSVMHEALHNHYTQKSLSLSPGK kappa light chain constant region
(SEQ ID NO: 59)
RTVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKSF

NRGEC

TABLE 3

Combinations of light chain variable region and heavy chain variable region of intact antibodies derived from HRP00049 mutation

| Name of antibody | Combination of heavy chain variable region and heavy chain variable region |
|---|---|
| H5L11 | 9-2 H5 and 9-2 L11 |
| H6L11 | 9-2 H6 and 9-2 L11 |
| H7L11 | 9-2 H7 and 9-2 L11 |

TABLE 4-1

Combinations of light chain variable region and heavy chain variable region of complete antibodies derived from HRP00052 mutation

| Name of the combination of the variable regions | Combination of heavy chain variable region and light chain variable region |
|---|---|
| H12L64 | 24D5 H12 and 24D5 L64 |
| H12L61 | 24D5 H12 and 24D5 L61 |
| H13L61 | 24D5 H13 and 24D5 L61 |
| H14L61 | 24D5 H14 and 24D5 L61 |
| H15L61 | 24D5 H15 and 24D5 L61 |
| H16L61 | 24D5 H16 and 24D5 L61 |
| H17L61 | 24D5 H17 and 24D5 L61 |
| H18L61 | 24D5 H18 and 24D5 L61 |
| H19L61 | 24D5 H19 and 24D5 L61 |
| H20L66 | 24D5 H20 and 24D5 L66 |
| H20L64 | 24D5 H20 and 24D5 L64 |

TABLE 4-2

Combinations of light chain variable region and heavy chain variable region of complete antibodies derived from HRP00052 mutation

| Name of variable regions | 24D5 L61 | 24D5 L64 | 24D5 L66 | 24D5 L67 | 24D5 L68 | 24D5 L69 |
|---|---|---|---|---|---|---|
| 24D5 H12 | H12L61 | H12L64 | H12L66 | H12L67 | H12L68 | H12L69 |
| 24D5 H13 | H13L61 | H13L64 | H13L66 | H13L67 | H13L68 | H13L69 |
| 24D5 H14 | H14L61 | H14L64 | H14L66 | H14L67 | H14L68 | H14L69 |
| 24D5 H15 | H15L61 | H15L64 | H15L66 | H15L67 | H15L68 | H15L69 |
| 24D5 H16 | H16L61 | H16L64 | H16L66 | H16L67 | H16L68 | H16L69 |
| 24D5 H17 | H17L61 | H17L64 | H17L66 | H17L67 | H17L68 | H17L69 |
| 24D5 H18 | H18L61 | H18L64 | H18L66 | H18L67 | H18L68 | H18L69 |
| 24D5 H19 | H19L61 | H19L64 | H19L66 | H19L67 | H19L68 | H19L69 |
| 24D5 H20 | H20L61 | H20L64 | H20L66 | H20L67 | H20L68 | H20L69 |
| 24D5 H21 | H21L61 | H21L64 | H21L66 | H21L67 | H21L68 | H21L69 |

In specific embodiments of the present disclosure, all of the heavy variable regions and light chain variable regions derived from the H RP00049 and HRP00052 mutant antibody, libraries as described in Table 5-1 and Table 5-2, when linked to the heavy constant regions and light chain constant regions to form a complete antibody, represent the complete antibody formed by connecting with the human IgG1 heavy chain constant region (SEQ ID NO: 58) and kappa light chain constant region (SEQ ID NO: 59) described above. For example, H15L61 refers to that the heavy chain is formed by connecting H15 with IgG1 heavy chain constant region and the light chain is formed by connecting L61 with kappa light chain constant region, and the light and heavy chains are linked to form a complete antibody, and other antibodies were named by analogy.

HRP00052-IgG1 refers to that the complete antibody is formed by replacing the heavy chain constant region (IgG4 subclass) of HRP00052 with the above IgG1 heavy chain constant region (SEQ ID NO: 58).

In order to compare with complete antibodies connecting with the constant region of the heavy chain of human IgG1, in some specific embodiments, the full-length antibodies in Table 6-1 and Table 6-2 are complete antibodies formed by connecting the heavy chain variable region and light chain variable region screened from the libraries derived from above HRP00049 and HRP00052 with the following human IgG4 heavy chain constant region (of SEQ 11) NO: 60, containing S228P and 234A235A mutations) and kappa light chain constant region (same as SEQ ID NO: 59), respectively. For example, H15L61-IgG4 refers to the complete antibody which is formed by connecting the heavy chain with light chain, wherein the heavy chain is formed by connecting H15 with IgG4 heavy chain constant region, and the light chain is formed by connecting L61 with kappa light chain constant region, and other antibodies were named by analogy.

TABLE 5-1

Full-length antibody names obtained by connecting the heavy chain variable regions with IgG1 heavy chain constant region (SEQ ID NO: 58) and the light chain variable regions with kappa light chain constant region (SEQ ID NO: 59)

| Name of variable region | 24D5 L61 | 24D5 L64 | 24D5 L66 | 24D5 L67 | 24D5 L68 | 24D5 L69 |
|---|---|---|---|---|---|---|
| 24D5 H12 | H12L61 | H12L64 | H12L66 | H12L67 | H12L68 | H12L69 |
| 24D5 H13 | H13L61 | H13L64 | H13L66 | H13L67 | H13L68 | H13L69 |
| 24D5 H14 | H14L61 | H14L64 | H14L66 | H14L67 | H14L68 | H14L69 |
| 24D5 H15 | H15L61 | H15L64 | H15L66 | H15L67 | H15L68 | H15L69 |
| 24D5 H16 | H16L61 | H16L64 | H16L66 | H16L67 | H16L68 | H16L69 |
| 24D5 H17 | H17L61 | H17L64 | H17L66 | H17L67 | H17L68 | H17L69 |
| 24D5 H18 | H18L61 | H18L64 | H18L66 | H18L67 | H18L68 | H18L69 |
| 24D5 H19 | H19L61 | H19L64 | H19L66 | H19L67 | H19L68 | H19L69 |
| 24D5 H20 | H20L61 | H20L64 | H20L66 | H20L67 | H20L68 | H20L69 |
| 24D5 H21 | H21L61 | H21L64 | H21L66 | H21L67 | H21L68 | H21L69 |

TABLE 5-2

Full-length antibody names obtained by connecting the heavy chain variable regions with IgG1 heavy chain constant region (SEQ ID NO: 58) and the light chain variable regions with kappa light chain constant region (SEQ ID NO: 59)

| Name of variable region | 9-2 H5 | 9-2 H6 | 9-2 H7 |
|---|---|---|---|
| 9-2 L11 | H5L11 | H6L11 | H7L11 |

Human IgG4 heavy chain contnt region:
(SEQ ID NO: 60)
ASTKGPSVFPLAPCSRSTSESTAALGCLVKDYFPEPVTVSWNSGALTSGVH

TFPAVLQSSGLYSLSSVVTVPSSSLGTKTYTCNVDHKPSNTKVDKRVESKY

GPPCPPCPAPEAAGGPSVFLFPPKPKDTLMISRTPEVTCVVVDVSQEDPEV

QFNWYVDGVEVHNAKTKPREEQFNSTYRVVSVLTVLHQDWLNGKEYKCKVS

NKGLPSSIEKTISKAKGQPREPQVYTLPPSQEEMTKNQVSLTCLVKGFYPS

-continued

DIAVEWESNGQPENNYKTTPPVLDSDGSFFLYSRLTVDKSRWQEGNVFSCS

VMHEALHNHYTQKSLSLSLGK

TABLE 6-1

Full-length antibody name obtanied by connecting the heavy chain variable region with IgG4 heavy chain constant region (SEQ ID NO: 60) and the light chain variable region with kappa light chain constant region (SEQ ID NO: 59)

| Name of variable region | 24D5 L61 | 24D5 L64 | 24D5 L66 | 24D5 L67 | 24D5 L68 | 24D5 L69 |
|---|---|---|---|---|---|---|
| 24D5 H12 | H12L61-IgG4 | H12L64-IgG4 | H12L66-IgG4 | H12L67-IgG4 | H12L68-IgG4 | H12L69-IgG4 |
| 24D5 H13 | H13L61-IgG4 | H13L64-IgG4 | H13L66-IgG4 | H13L67-IgG4 | H13L68-IgG4 | H13L69-IgG4 |
| 24D5 H14 | H14L61-IgG4 | H14L64-IgG4 | H14L66-IgG4 | H14L67-IgG4 | H14L68-IgG4 | H14L69-IgG4 |
| 24D5 H15 | H15L61-IgG4 | H15L64-IgG4 | H15L66-IgG4 | H15L67-IgG4 | H15L68-IgG4 | H15L69-IgG4 |
| 24D5 H16 | H16L61-IgG4 | H16L64-IgG4 | H16L66-IgG4 | H16L67-IgG4 | H16L68-IgG4 | H16L69-IgG4 |
| 24D5 H17 | H17L61-IgG4 | H17L64-IgG4 | H17L66-IgG4 | H17L67-IgG4 | H17L68-IgG4 | H17L69-IgG4 |
| 24D5 H18 | H18L61-IgG4 | H18L64-IgG4 | H18L66-IgG4 | H18L67-IgG4 | H18L68-IgG4 | H18L69-IgG4 |
| 24D5 H19 | H19L61-IgG4 | H19L64-IgG4 | H19L66-IgG4 | H19L67-IgG4 | H19L68-IgG4 | H19L69-IgG4 |
| 24D5 H20 | H20L61-IgG4 | H20L64-IgG4 | H20L66-IgG4 | H20L67-IgG4 | H20L68-IgG4 | H20L69-IgG4 |
| 24D5 H21 | H21L61-IgG4 | H21L64-IgG4 | H21L66-IgG4 | H21L67-IgG4 | H21L68-IgG4 | H21L69-IgG4 |

TABLE 6-2

Full-length antibody names obtained by connecting the heavy chain variable region with IgG4 heavy chain constant region (SEQ ID NO: 60) and the light chain variable region with kappa light chain constant region (SEQ ID NO: 59)

| Name of variable region | 9-2 H5 | 9-2 H6 | 9-2 H7 |
|---|---|---|---|
| 9-2 L11 | H5L11-IgG4 | H6L11-IgG4 | H7L11-IgG4 |

In some specific embodiments, the full-length antibodies in Table 7-1 and Table 7-2 are complete antibodies formed by connecting the heavy chain variable region and light chain variable region screened from the libraries derived from the above HRP00049 and HRP00052 with the following human IgG4 S228P heavy chain constant region (of SEQ ID NO: 65, containing S228P mutation) and kappa light chain constant region (same as SEQ ID NO: 59), respectively. For example, H15L61-IgG4 refers to the complete antibody which is formed by combining the heavy chain with light chain, wherein the heavy chain is formed by connecting. H15 with IgG4 heavy chair constant region, and the light chain is formed by connecting L61 with kappa light chain constant region, and other antibodies were named by analogy. The sequence of the heavy chain constant region of IgG4 S228P is as follows:

(SEQ ID NO: 65)
ASTKGPSVFPLAPCSRSTSESTAALGCLVKDYFPEPVTVSWNSGALTSGVH

TFPAVLQSSGLYSLSSVVTVPSSSLGTKTYTCNVDHKPSNTKVDKRVESKY

GPPCPPCPAPEFLGGPSVFLFPPKPKDTLMISRTPEVTCVVVDVSQEDPEV

QFNWYVDGVEVHNAKTKPREEQFNSTYRVVSVLTVLHQDWLNGKEYKCKVS

NKGLPSSIEKTISKAKGQPREPQVYTLPSSQEEMTKNQVSLTCLVKGFYPS

DIAVEWESNGQPENNYKTTPPVLDSDGSFFLYSRLTVDKSRWQEGNVFSCS

VMHEALHNHYTQKSLSLSLGK

TABLE 7-1

Full-length antibody names obtained by connecting the heavy chain variable region with IgG4 S228P heavy chain constant region (SEQ ID NO: 65) and the light chain variable region with kappa light chain constant region (SEQ ID NO: 59)

| Name of variable region | 24D5 L61 | 24D5 L64 | 24D5 L66 | 24D5 L67 | 24D5 L68 | 24D5 L69 |
|---|---|---|---|---|---|---|
| 24D5 H12 | H12L61-IgG4 S228P | H12L64-IgG4 S228P | H12L66-IgG4 S228P | H12L67-IgG4 S228P | H12L68-IgG4 S228P | H12L69-IgG4 S228P |
| 24D5 H13 | H13L61-IgG4 S228P | H13L64-IgG4 S228P | H13L66-IgG4 S228P | H13L67-IgG4 S228P | H13L68-IgG4 S228P | H13L69-IgG4 S228P |

TABLE 7-1-continued

Full-length antibody names obtained by connecting the heavy chain variable region with IgG4 S228P heavy chain constant region (SEQ ID NO: 65) and the light chain variable region with kappa light chain constant region (SEQ ID NO: 59)

| Name of variable region | 24D5 L61 | 24D5 L64 | 24D5 L66 | 24D5 L67 | 24D5 L68 | 24D5 L69 |
|---|---|---|---|---|---|---|
| 24D5 H14 | H14L61-IgG4 S228P | H14L64-IgG4 S228P | H14L66-IgG4 S228P | H14L67-IgG4 S228P | H14L68-IgG4 S228P | H14L69-IgG4 S228P |
| 24D5 H15 | H15L61-IgG4 S228P | H15L64-IgG4 S228P | H15L66-IgG4 S228P | H15L67-IgG4 S228P | H15L68-IgG4 S228P | H15L69-IgG4 S228P |
| 24D5 H16 | H16L61-IgG4 S228P | H16L64-IgG4 S228P | H16L66-IgG4 S228P | H16L67-IgG4 S228P | H16L68-IgG4 S228P | H16L69-IgG4 S228P |
| 24D5 H17 | H17L61-IgG4 S228P | H17L64-IgG4 S228P | H17L66-IgG4 S228P | H17L67-IgG4 S228P | H17L68-IgG4 S228P | H17L69-IgG4 S228P |
| 24D5 H18 | H18L61-IgG4 S228P | H18L64-IgG4 S228P | H18L66-IgG4 S228P | H18L67-IgG4 S228P | H18L68-IgG4 S228P | H18L69-IgG4 S228P |
| 24D5 H19 | H19L61-IgG4 S228P | H19L64-IgG4 S228P | H19L66-IgG4 S228P | H19L67-IgG4 S228P | H19L68-IgG4 S228P | H19L69-IgG4 S228P |
| 24D5 H20 | H20L61-IgG4 S228P | H20L64-IgG4 S228P | H20L66-IgG4 S228P | H20L67-IgG4 S228P | H20L68-IgG4 S228P | H20L69-IgG4 S228P |
| 24D5 H21 | H21L61-IgG4 S228P | H21L64-IgG4 S228P | H21L66-IgG4 S228P | H21L67-IgG4 S228P | H21L68-IgG4 S228P | H21L69-IgG4 S228P |

TABLE 7-2

Full-length antibody names obtained by connecting the heavy chain variable region with IgG4 S228P heavy chain constant region (SEQ ID NO: 65) and the light chain variable region with kappa light chain constant region (SEQ ID NO: 59)

| Name of variable region | 9-2 H5 | 9-2 H6 | 9-2 H7 |
|---|---|---|---|
| 9-2 L11 | H5L11-IgG4 S228P | H6L11-IgG4 S228P | H7L11-IgG4 S228P |

The specific light chain constant region and heavy chain constant region are not intended to limit the antibody constant regions of the present disclosure, and other light chain constant regions and heavy chain constant regions and mutants thereof known in the art can also be selected to improve their performance.

Merck's PD-L1 antibody Avelumab (A09) and/or Genetech's 3280A were used as a positive control herein, wherein the amino acid sequences of the light chain amino acid sequence and the heavy chain of A09 (sourced from US20140341917) are as follows:

>A09 heavy chain:
(SEQ ID NO: 61)
EVQLLESGGGLVQPGGSLRLSCAASGFTFSSYIMMWVRQAPGKGLEWVSSI

YPSGGITFYADTVKGRFTISRDNSKNTLYLQMNSLRAEDTAVYYCARIKLG

TVTTVDYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPS

-continued

RDELTKNQVSLTCLVKGFYPSDIAVEWESNGQPENNYKTTPPVLDSDGSFF

LYSKLTVDKSRWQQGNVFSCSVMHEALHNHYTQKSLSLSPGK

>A09 light chain:
(SEQ ID NO: 62)
QSALTQPASVSGSPGQSITISCTGTSSDVGGYNYVSWYQQHPGKAPKLMIY

DVSNRPSGVSNRFSGSKSGNTASLTISGLQAEDEADYYCSSYTSSSTRVFG

TGTKVTVLGQPKANPTVTLFPPSSEELQANKATLVCLISDFYPGAVTVAWK

ADGSPVKAGVETTKPSKQSNNKYAASSYLSLTPEQWKSHRSYSCQVTHEGS

TVEKTVAPTECS

The amino acid sequences of the light chain amino acid sequence and the heavy chain of 3280A (Genetech, Atezolizumab, WHO Drug Information, Vol. 28, No. 4, 2014, P488) are as follows:

>3280A heavy chain:
(SEQ ID NO: 63)
EVQLVESGGGLVQPGGSLRLSCAASGFTFSDSWIHWVRQAPGKGLEWVAWI

SPYGGSTYYADSVKGRFTISADTSKNTAYLQMNSLRAEDTAVYYCARRHWP

GGFDYWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNVN

HKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYASTYRVVSV

LTVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFLY

SKLTVDKSRWQQGNVFSCSVMHEALHNHYGKSLSLSPGK

-continued

>3280A light chain:
(SEQ ID NO: 64)
DIQMTSPSSLSASVGDRVTITCRASQDVSTAVAWYQQKPFKAPKLLIYSAS

FLYSGVPSRFSGSGSGTDFTLTISSLQPEDFATYYCQQYLYHPATFGQGTK

VEIKRTVAAPSVFIFPPSDEQLKSGTASVVCLLNNFYPREAKVQWKVDNAL

QSGNSQESVTEQDSKDSTYSLSSTLTLSKADYEKHYKVYACEVTHQGLSSP

VTKSFNRGEC

PD-L1 antibodies described above were purified by conventional methods.

The antibodies in the following examples are all full-length antibodies

Embodiment 4

Ligand Blocking Test of Antibody

The blocking effect of the product on the binding of PD-L1 and PD1 was further studied, meanwhile the product was compared with similar products in clinical trials. Methods refers to WO201708495A1 Test Examples 2 and 3, and human PD-L1 antibody was used to block the binding of mouse PD-L1/PD-1 in the mouse PD-L1/PD-1 binding blocking test. See Table 8 below for details of the data.

TABLE 8

Test of PD-L1 antibody blocking the binding of PD-L1 to its ligand

| Antibody | Blocking the binding of human PD-L1/PD-1 (10 μg/ml*) IC50 (ng/ml) | Blocking the binding of mouse PD-L1/PD-1 (5 μg/ml*) IC50 (ng/ml) | Blocking the binding of B7-1 to human PD-L1/PD-1 (1 μg/ml*) IC50 (ng/ml) |
|---|---|---|---|
| H5L11 | 0.1679 | 0.9267 | 1.445 |
| H6L11 | 0.2901 | 1.230 | 1.688 |
| HRP00049-IgG1 | 0.2647 | — | 1.882 |
| A09 | 0.3039 | 1.040 | 1.565 |
| HRP00052-IgG1 | 0.3379 | — | 1.651 |
| H18L61 | 0.2275 | — | 1.379 |
| H12L64 | 0.2153 | — | 0.8258 |
| HRP00052 | 0.2418 | — | 1.228 |
| IgG1 control | — | — | — |

*10 μg/ml, 5 μg/ml and 1 μg/ml are the concentrations of PD-L1 in different blocking tests.
Ligand blocking test proves that the PD-L1 antibody of the present disclosure can block the binding of PD-L1 and PD1, as well as the binding of PD-L1 and B7-1, and the H5L11 and H6L11 antibodies mutated from HRP00049 have the cross-binding activity of mouse PD-L1 that can block the binding ability of mouse PD-L1 to PD-1.

Embodiment 5

BIAcore Antibody Affinity Test of Exemplary Antibodies

According to the method in the manual of human anti-capture kit (Cat. A BR-1008-39, GE), the human anti-capture antibody was covalently coupled to biosensor chip CM5 (Cat. #BR-1000-12, GE) so that a certain amount of human PD-L1 (Cat. #10084-H08H, Sino Biological) monkey PD-L1 (Cat. #90251-C08H, Sino Biological), mouse PD-L1 (Cat. #50010-M08H, Sino Biological) were affinity captured. The affinity of PD-L1 antibody reacting with PD-L1 was measured with Biacore X100, GE instrument. In this test, HBS-EP+10× buffer solution (Cat. #BR-1006-69, GE) diluting with D. I. Water to 1×(pH7.4) was used, and BIAevaluation version 4.1, GE software was used to fit the data with (1:1) Langmuir model to obtain the affinity value. The results are shown in Table 9.

TABLE 9-1

Biacore binding affinity of HRP00049, HRP00052 and mutant antibodies thereof to different species of PD-L1 (Batch testing)

| Antibody | Target protein | ka (1/Ms) | kd (1/s) | KD (M) |
|---|---|---|---|---|
| HRP00052 | Human | 1.73E6 | 1.16E−4 | 6.72E−11 |
| 3280A | PD-L1 | 1.52E5 | 2.51E−4 | 1.66E−9 |
| H12L64 | | 2.18E6 | 7.10E−5 | 3.26E−11 |
| H12L61 | | 2.18E6 | 7.10E−5 | 3.26E−11 |
| H13L61 | | 2.55E6 | 6.66E−5 | 2.61E−11 |
| H14L61 | | 2.40E6 | 9.10E−5 | 3.80E−11 |
| H15L61 | | 2.43E6 | 7.88E−5 | 3.25E−11 |
| H16L61 | | 2.53E6 | 6.43E−5 | 2.54E−11 |
| H17L61 | | 2.43E6 | 9.53E−5 | 3.93E−11 |
| H18L61 | | 1.71E6 | 5.63E−5 | 3.30E−11 |
| H19L61 | | 2.34E6 | 7.65E−5 | 3.27E−11 |
| HRP00049 | | 6.38E5 | 1.19E−4 | 1.86E−10 |
| A09 | | 3.46E5 | 1.15E−4 | 3.33E−10 |
| H5L11 | | 6.11E5 | 1.24E−4 | 2.03E−10 |
| H6L11 | | 4.95E5 | 1.13E−4 | 2.27E−10 |
| H7L11 | | 2.81E5 | 3.89E−4 | 1.39E−9 |
| HRP00052 | Monkey | 1.51E6 | 9.38E−5 | 6.20E−11 |
| H12L64 | (cyno) | 1.83E6 | 8.38E−5 | 4.58E−11 |
| H18L61 | PD-L1 | 1.60E6 | 7.68E−5 | 4.80E−11 |
| HRP00049 | | 5.93E5 | 1.11E−4 | 1.87E−10 |
| H6L11 | | 4.74E5 | 1.51E−4 | 3.18E−10 |
| H5L11 | | 5.72E5 | 1.21E−4 | 2.11E−10 |
| HRP00049 | Mouse | | No binding | |
| HRP00052 | PD-L1 | | No binding | |
| A09 | | 1.89E4 | 9.14E−5 | 4.85E−9 |
| 3280A | | 6.33E4 | 3.39E−3 | 5.35E−8 |
| H5L11 | | 8.11E5 | 5.64E−2 | 6.96E−8 |
| H6L11 | | 6.55E5 | 1.19E−2 | 1.81E−8 |
| H7L11 | | 1.35E5 | 1.82E−2 | 1.35E−7 |

TABLE 9-2

Biacore binding affinity of HRP00052 and mutant antibodies thereof to different species of PD-L1 (Batch testing)

| Antibody | Target protein | ka (1/Ms) | kd (1/s) | KD (M) |
|---|---|---|---|---|
| HRP00052 | hPDL1 | 1.26E+06 | 1.39E−04 | 1.10E−10 |
| | Cyno PDL1 | 1.26E+06 | 1.43E−04 | 1.14E−10 |
| H21L66 | hPD-L1 | 1.95E+06 | 1.04E−04 | 5.33E−11 |
| | Cyno PD-L1 | 2.17E+06 | 1.22E−04 | 5.63E−11 |
| H21L67 | hPD-L1 | 2.30E+06 | 1.20E−04 | 5.22E−11 |
| | Cyno PD-L1 | 2.35E+06 | 1.24E−04 | 5.28E−11 |
| H21L68 | hPD-L1 | | No binding | |
| | Cyno PD-L1 | | No binding | |
| H21L69 | hPD-L1 | 2.29E+06 | 1.29E−04 | 5.63E−11 |
| | Cyno PD-L1 | 2.27E+06 | 1.19E−04 | 5.26E−11 |

The results showed that the affinity of the antibodies screened from HRP00052 mutant antibody library (except H21L68) to human PD-L1 was higher than that of HRP00052, and the above two were both higher than that of the positive control antibody, while antibodies H5L11, H6L11 and H7L11 screened from HRP00049 mutant antibody library showed strong cross-affinity activity of mouse PD-L1.

Embodiment 6

Secretion of Cellular IFNγ of PD-L1 Antibody in PBMC-T Lymphocyte Activation Test In order to study the effect of PD-L1 antibody on the function of human primary T lymphocytes, human peripheral blood mononuclear cells (PBMC) were collected and purified. After 5 days of in vitro stimulation with tuberculin (TB), secretion level of cytokine IFNγ was detected. The experimental process is briefly described as follows:

PBMC was obtained from fresh blood by Ficoll-Hypaque density gradient centrifugation (Stem Cell Technologies), and cultured in RPMI 1640 medium, to which 10% (v/v) FBS was added, followed by culturing at 37° C. and 5% $CO_2$.

Freshly isolated and purified PBMC was prepared into a cell suspension with a density of $2\times10^6$/ml using RPMI 1640 medium, and 25 µl of tuberculin was added to every 20 mL of cell suspension, followed by culturing in an incubator at 37° C. and 5% $CO_2$ for 5 days. On the sixth day, the cultured cells were centrifuged, washed once with PBS, resuspended in fresh RPMI 1640 medium, adjusted to a density of $1\times10^6$/ml, and seeded into 96-well cell culture plates at a volume of 90 µl per well. Gradient diluted antibody samples (diluted with PBS) or equal amount of isotype IgG was added simultaneously as blank control at a volume of 10 µl per well. The cell culture plate was placed in an incubator and incubated at 37° C. and 5% $CO_2$ for 3 days, and then taken out and centrifuged (4000 rpm, 10 min) to collect the cell culture supernatant. ELISA (human IFN-γ test kit, Xinbosheng. EHC 102 g.96) was used to detect the level of IFN-γ. Refer to the reagent manual for specific operations.

Results (see FIG. 1) show that H18L61, H12L64, H5L11 and H6L11 can strongly stimulate the intracellular secretion of IFNγ. Among them, H12L64, H5L11 and H6L11 exhibit a dose-dependent trend when promoting intracellular IFNγ secretion. All of the above four antibodies are superior to HRP00052-IgG1 at some doses or all doses.

Embodiment 7

Exemplary Antibody-Mediated ADCC Effect of PD-L1+Cells

Human whole blood diluted with an equal volume of PBS buffer was added to the bottom of a SepMate (STEMCELL, Technologies Inc., 15460) tube with an appropriate amount of Lymphoprep (STEMCELL Technologies Inc., 07851), and centrifuged at 1200 g for 10 minutes at room temperature. Pouring the upper liquid in the tube into a new 50 ml centrifuge tube, the cells were washed with PBS buffer, and centrifuged at 300 g for 8 minutes to obtain PBMC. PBMC was then resuspended in RPMI-1640 medium containing 5% Low IgG FBS (BIOSUN, BS-0007-500), and cell count was performed.

CHO-S/PD-L1 cells were resuspended in RPMI1640 medium containing 5% Low IgG FBS and counted, seeded in 96-well plates at a density of 10,000 cells per well, and incubated with gradient diluted of PD-L1 antibody for 15 minutes, then 300,000 human PBMC cells were added to each well and interacted with the antibody for 4 hours. Medium controls, such as CHO-S/PD-L1 cell spontaneous release control, PBMC cell spontaneous release control and CHO-S/PD-L1 cell maximum lysis control were set. After 4 hours, the 96-well plate was centrifuged, 50 µL of supernatant from each well was transferred to another 96-well plate, 50 µL CytoTox 96 Non-Radioactive Cytotoxicity Assay (Promega, G1780) was added to each well, and incubated for 30 minutes at room temperature in the dark. Stop solution was added and the absorbance at 490 nm was read. The data was analyzed according to the following formula to calculate the lysis rate. The Graphpad Prism software was used to calculate the EC50 value of the ADCC effect of the antibody according to the antibody concentration and the corresponding lysis rate.

Lysis rate %=(sample well$_{490nm}$-PBMC cells spontaneously release$_{490nm}$-CHO-S/PD-L1 cells spontaneously release$_{490nm}$)/(CHO-S/PD-L1 cells maximum lysis$_{490nm}$-CHO-S/PD-L1 cells spontaneously release$_{490nm}$)$\times$100

The results show (as shown FIGS. 2A to 2F) that all IgG1 forms of different PD-L1 antibodies HRP00049-IgG1, H5L11, HRP00052-IgG1, H6L11, H18L61 and H12L64 have strong ADCC effects, and ADCC effects of these molecules are all significantly superior to IgG4 form of various PD-L1 antibodies.

Embodiment 8

Effect of Exemplary Antibodies in Human Melanoma A375 Xenograft Model

The cultured A375 cells and PBMC were mixed and inoculated subcutaneously in NOG mice. The experiments were classified into PBMC+PBS group, PBMC+H12L64 20 mg/kg group, PBMC+H12L64-IgG4-20 mg/kg group and PBMC+HRP00052 20 mg/kg group. Six mice in each group were administrated intraperitoneally once every two days for 11 consecutive times. After the administration was completed, the therapeutic effect was evaluated using tumor growth inhibition rate TGI (%) and relative tumor growth rate T/C. (%).

Figure 3:
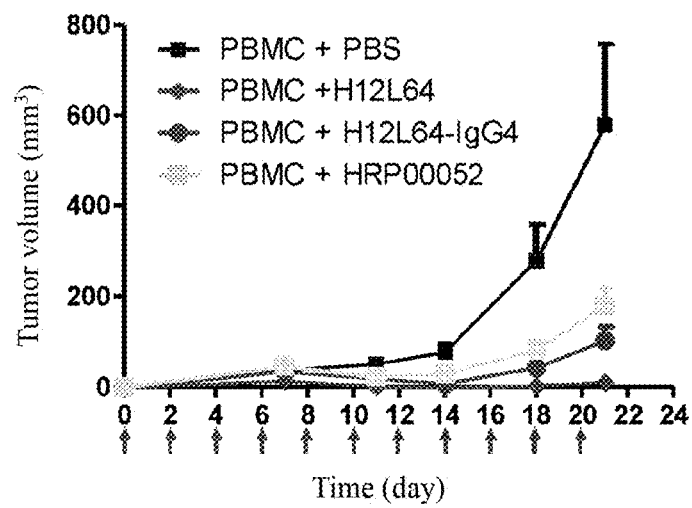
FIG. 3: Effect of PD-L1 antibody on tumor volume of mouse A375 xenograft model.

Results are shown in FIG. 3 and Table 10. The TGI of H12L64 20 mg/kg group was 98.15%, which was significantly different from that of PBMC (PBS group (p=0.0018); the tumor inhibition rate TGI of H12L64-IgG4 20 mg/kg group was 32.15%, which was significantly different from that of PBMC+PBS group (p=0.0064); the tumor inhibition rate TGI of the HRP00052 20 mg/kg group was 68.84%, which was significantly different from that of PBMC+PBS group (p=0.0291). The results show that the H12L64 20 mg/kg group, H12L63-IgG4 20 mg/kg and HRP00052 20 mg/kg can effectively inhibit the growth of A375 (p<0.05). Throughout the whole experiment, H12L64, H12L64-IgG4 and HRP00052 tumor-bearing mice showed no weight loss or animal death, indicating that H12L64, H12L64-IgG4 and HRP00052 at this dose were well tolerated by mice.

TABLE 10

Efficacy of PD-L1 antibodies in humanized A375 subcutaneous xenograft model

| Experiment group | N | Tumor volume (mm³) (Mean ± SEM) Day 21 | TGI % Day 21 | T/C % Day 21 | P Vs PBMC + PBS Day 21 | Remarks |
|---|---|---|---|---|---|---|
| PBMC + PBS | 6 | 581.31 ± 177.69 | — | — | — | — |
| PBMC + H12L64 20 mg/kg | 6 | 10.77 ± 7.38 | 98.15 | 1.85 | 0.0018 | 4/6(CR) |
| PBMC + H12L64-IgG4 20 mg/kg | 6 | 103.74 ± 30.41 | 82..15 | 17.85 | 0.0064 | 0/6(CR) |
| PBMC + HRP00052 20 mg/kg | 5 | 181.14 ± 39.94 | 68.84 | 31.16 | 0.0291 | 0/5(CR) |

TGI %: tumor growth inhibition value; T/C %: tumor growth rate; CR: tumor regression.

Embodiment 9

Effect of PD-L1 Antibody on Mouse Colon Cancer Model MC38-hPD-L1

100 µl of MC38-hPD-L1 cells were inoculated (hPD-L1 can be expressed on the cell surface after transforming hPD-L1 into mouse colon cancer cells MC38, $4 \times 10^5$ cells) to the right rib of 50 C57 mice, and animals with too large or small volume of tumor were removed. According to the average tumor volume of about 52 mm³, mice were randomly divided into three PD-L1 antibody single-use groups and a negative control group, with a total of 4 groups and 10 mice in each group. After grouping, each drug was administrated intraperitoneally (an equal volume of PBS was injected with the mice in the control group) three times a day for a total of 12 times. The administration period was 28 days, and the monitoring of tumor-bearing mice ended two days after drug withdrawal. The tumor volume was measured, weight was weighed and the data was recorded twice a week. See the following table for grouping and administration. Body weight, tumor volume and tumor weight of animals in each group were characterized by mean±standard deviation (Mean+SEM). Graphpad Prism 5 and Excel software was used for plotting, and student t test was used for statistical analysis.

Tumor volume (TV)=½×$L_{long}$=$L_{short}^2$
Tumor proliferation rate T/C %=(T−T0)/(C−C0)×100%
Tumor growth inhibition rate % TGI=1−T/C %

| G | Group | Number of animals | Dose of administration (mg/kg) | Route of administration |
|---|---|---|---|---|
| Group1 | Control (PBS) | 10 | — | ip |
| Group2 | HRP00052-IgG1-10mpk | 10 | 10 | ip |
| Group3 | H6L11-10mpk | 10 | 10 | ip |
| Group4 | A09-10mpk | 10 | 10 | ip |

Figure 4:
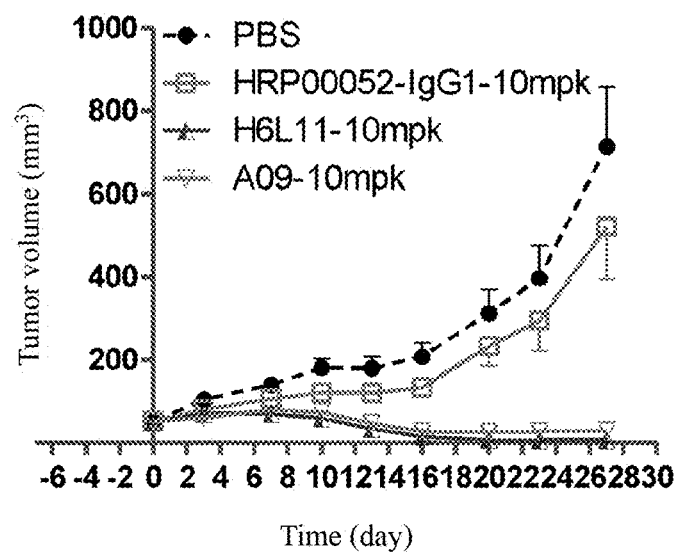
FIG. 4: Effect of PD-L1 antibody on tumor volume of mouse colon cancer model.

Experimental results (see FIG. 4 show that both H6L11 and A09 can significantly inhibit. the growth of MC38-hPI)-L1 subcutaneously implanted tumors. Compared with the negative control group, the tumor volume of the two groups showed statistical differences 3 days after administration (p<0.05). At the end of the experiment (27 days after administration), the tumor growth inhibition values of the two groups were 106.74% and 103.47%, respectively, which was very significantly different from those of the negative control group (p<0.001). About 80%-90% of tumors could completely regress and H6L11 has better tumor suppression effect than A09, but there is no statistical difference between these two (see FIG. 4). At the end of the experiment, the tumor growth inhibition rate of HRP00052-IgG1 was 29.10%.

After the experiment, the tumor-hearing mice were euthanized, and the tumor was peeled and weighed. Tumor weighting results were basically consistent with the size of the tumor volume: in three drug groups, the average tumor weight of the H6L11 group was the smallest, followed by the A09 group, and the average tumor weight of the HRP00052-IgG1 was the largest; there was significant difference between each of the two groups of H6L11 and A09 and the control group (p<0.001). Tumor-bearing mice were well tolerant to various drugs, and had no symptoms such as weight loss caused by drugs.

Embodiment 10

Effect of PD-L1 Antibody on Mouse Colon Cancer Model MC38-hPD-L1

MC38-hPD-L1 cells were inoculated subcutaneously into C57/BL-6 mice at a density of $5.8 \times 10^5$ cells/100 µl/mouse. After the tumor-bearing model was constructed, the tumor volume was measured, and animals with too large or small of body weight and tumor were removed. The tumor-bearing mice were randomly divided into 2 groups (n=7): IgG-PBS (C25-IgG4) control group, H5L11-IgG4 S228P experimental group according to the size of tumor, and the date of grouping and administrating was set as D0. After grouping, each drug was administered intraperitoneally three times a week for a total of 10 times. The administration period was 18 days, and the monitoring of tumor-bearing mice ended two days after drug withdrawal. The tumor volume was measured, weight was weighed and the data was recorded twice a week. See the following table for grouping and administration. Body weight, tumor volume and tumor weight of animals in each group were characterized by mean÷standard deviation (Mean±SEM). Graphpad Prism 5 and Excel software was used for plotting and student t test was used for statistical analysis.

Tumor volume (TV)=½×$L_{long}$×$L_{short}^2$
Tumor proliferation rate T/C %=(T−T0)/(C−C0)×100%
Tumor growth inhibition rate % TGI=1−T/C %

Figure 5:
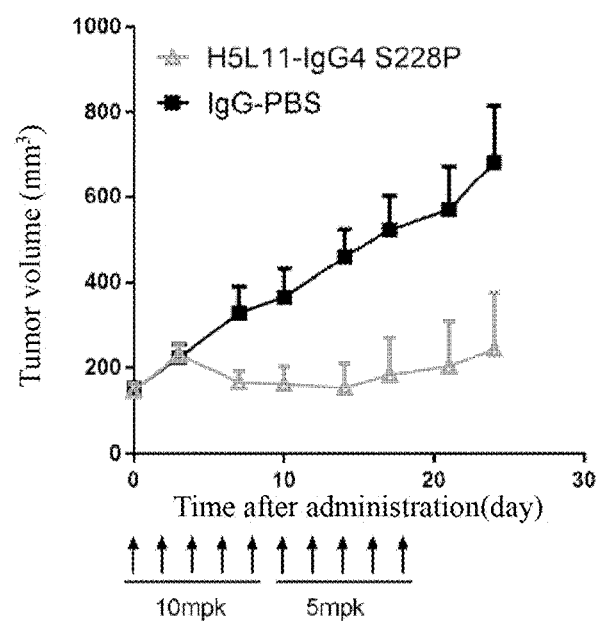
FIG. 5: Effect of PD-L1 antibody on tumor volume of mouse xenograft model.

Result was shown in FIG. 5, the tumor volume of the experimental group of PD-L1 monoclonal antibody (H5L11-IgG4 S228P group) that cross-reacted with mouse PD-L1 was significantly smaller than that of the control group, and there is a statistical difference between the experimental group and the control group from about one week after administration.

After the experiment, the tumor-hearing mice were euthanized, and the tumor was peeled and weighed. The tumor weight results were similar to the tumor volume. During the experiment, there was no significant difference in body weight between the administration group and the control group, and each administrated antibody was well tolerated by the mice.

Although the above invention has been described in detail with the aid of the drawings and embodiments tor a clear understanding, the description and embodiments are not intended to limit the scope of the present disclosure. The disclosures of all patents and scientific literature referred herein are fully and clearly incorporated by reference.

The invention claimed is:

1. A monoclonal antibody or an antigen-binding fragment thereof, wherein the monoclonal antibody or the antigen-binding fragment thereof binds to human PD-L1 and comprises a heavy chain variable region and a light chain variable region, wherein:

(I) the heavy chain variable region comprises HCDR1, HCDR2 and HCDR3 having amino acid sequences of SEQ ID NOs: 10, 12 and 13, respectively; and the light chain variable region comprises LCDR1, LCDR2 and LCDR3 having amino acid sequences of SEQ ID NOs: 14, 15 and 16, respectively; wherein $X_1$ is F or M, $X_2$ is R or V and $X_3$ is N or H in the HCDR2 of SEQ ID NO: 12; or (ii) the heavy chain variable region comprises HCDR1, HCDR2 and HCDR3 having amino acid sequences of SEQ ID NOs: 11, 12 and 13, respectively; and the light chain variable region comprises LCDR1, LCDR2 and LCDR3 having amino acid sequences of SEQ ID NOs: 14, 15 and 16, respectively; wherein $X_1$ is F or M, $X_2$ is R or V and $X_3$ is N or H in the HCDR2 of SEQ ID NO: 12; or (iii) the heavy chain variable region comprises HCDR1, HCDR2 and HCDR3 having amino acid sequences of SEQ ID NOs: 20, 21 and 22, respectively; and the light chain variable region comprises LCDR1, LCDR2 and LCDR3 having amino acid sequences of SEQ ID NOs: 23, 24 and 25, respectively; wherein HCDR1, HCDR2, HCDR3 and LCDR1, LCDR2, LCDR3 are not simultaneously SEQ ID NOs: 30, 38, 22, 23, 40 and 25, respectively, wherein $X_4$ is S or D, $X_5$ is Y or K, $X_6$ is H or M, $X_7$ is T, S, H or G, $X_8$ is S, N or G, $X_9$ is S, L or G, $X_{10}$ is F, L, W or M, $X_{11}$ is A, P or T, $X_{12}$ is M, V, L or S, $X_{13}$ is F or Y in the SEQ ID NOs: 20 and 21, and $X_{14}$ is V or A, $X_{15}$ is Y or N, $X_{16}$ is A, L or V and $X_{17}$ is E, F, Y, or A in the LCDR2 of SEQ ID NO: 24.

2. A monoclonal antibody or an antigen-binding fragment thereof, wherein the monoclonal antibody or the antigen-binding fragment thereof binds to human PD-L1 and comprises a heavy chain variable region and a light chain variable region, wherein:

the heavy chain variable region comprises a HCDR1 having an amino acid sequence of SEQ ID NO: 10, a HCDR2 having an amino acid sequence of SEQ ID NO: 28 or 29 and a HCDR3 having an amino acid sequence of SEQ ID NO: 13, the light chain variable region comprises LCDR1, LCDR2 and LCDR3 having amino acid sequences of SEQ ID NOs: 14, 15 and 16, respectively; or the heavy chain variable region comprises a HCDR1 having an amino acid sequence of SEQ ID NO: 11, a HCDR2 having an amino acid sequence of SEQ ID NO: 28 or 29 and a HCDR3 having an amino acid sequence of SEQ ID NO: 13, the light chain variable region comprises LCDR1, LCDR2 and LCDR3 having amino acid sequences of SEQ ID NOs: 14, 15 and 16 respectively; or the heavy chain variable region comprises a HCDR1 having an amino acid sequence of SEQ ID NO: 30, a HCDR2 having an amino acid sequence of any one of SEQ ID NOs: 32 to 37 and a HCDR3 having an amino acid sequence of SEQ ID NO: 22, the light chain variable region comprises a LCDR1 having an amino acid sequence of SEQ ID NO: 23, a LCDR2 having an amino acid sequence of any one of SEQ ID NOs: 39, 40, 41, 67 and 69 and a LCDR3 having an amino acid sequence of SEQ ID NO: 25; or the heavy chain variable region comprises a HCDR1 having an amino acid sequence of SEQ ID NO: 31, a HCDR2 having an amino acid sequence of any one of SEQ ID NOs: 32 to 37 and a HCDR3 having an amino acid sequence of SEQ ID NO: 22, the light chain variable region comprises a LCDR1 having an amino acid sequence of SEQ ID NO: 23, a LCDR2 having an amino acid sequence of any one of SEQ ID NOs: 39, 40, 41, 67 and 69 and a LCDR3 having an amino acid sequence of SEQ ID NO: 25.

3. The monoclonal antibody or the antigen-binding fragment thereof of claim 2, wherein:

the heavy chain variable region comprises HCDR1, HCDR2 and HCDR3 having amino acid sequences of SEQ ID NO: 10, SEQ ID NO: 28 and SEQ ID NO:13, respectively; the light chain variable region comprises LCDR1, LCDR2 and LCDR3 having amino acid sequences of SEQ ID NOs: 14, 15 and 16, respectively;

the heavy chain variable region comprises HCDR1, HCDR2 and HCDR3 having amino acid sequences of SEQ ID NO: 11, SEQ ID NO: 28 and SEQ ID NO:13, respectively; the light chain variable region comprises LCDR1, LCDR2 and LCDR3 having amino acid sequences of SEQ ID NOs: 14, 15 and 16, respectively;

the heavy chain variable region comprises HCDR1, HCDR2 and HCDR3 having amino acid sequences of SEQ ID NO: 11, SEQ ID NO: 29 and SEQ ID NO:13, respectively; the light chain variable region comprises LCDR1, LCDR2 and LCDR3 having amino acid sequences of SEQ ID NOs: 14, 15 and 16, respectively;

the heavy chain variable region comprises HCDR1, HCDR2 and HCDR3 having amino acid sequences of SEQ ID NO: 30, SEQ ID NO: 32 and SEQ ID NO:22, respectively; the light chain variable region comprises LCDR1, LCDR2 and LCDR3 having amino acid sequences of SEQ ID NO: 23, SEQ ID NO: 39 and SEQ ID NO:25, respectively;

the heavy chain variable region comprises HCDR1, HCDR2 and HCDR3 having amino acid sequences of SEQ ID NO: 30, SEQ ID NO: 32 and SEQ ID NO:22, respectively; the light chain variable region comprises LCDR1, LCDR2 and LCDR3 having amino acid sequences of SEQ ID NO: 23, SEQ ID NO: 40 and SEQ ID NO:25, respectively;

the heavy chain variable region comprises HCDR1, HCDR2 and HCDR3 having amino acid sequences of SEQ ID NO: 30, SEQ ID NO: 33 and SEQ ID NO:22, respectively; the light chain variable region comprises LCDR1, LCDR2 and LCDR3 having amino acid sequences of SEQ ID NO: 23, SEQ ID NO: 40 and SEQ ID NO:25, respectively;

the heavy chain variable region comprises HCDR1, HCDR2 and HCDR3 having amino acid sequences of SEQ ID NO: 30, SEQ ID NO: 34 and SEQ ID NO:22, respectively; the light chain variable region comprises LCDR1, LCDR2 and LCDR3 having amino acid sequences of SEQ ID NO: 23, SEQ ID NO: 40 and SEQ ID NO:25, respectively;

the heavy chain variable region comprises HCDR1, HCDR2 and HCDR3 having amino acid sequences of SEQ ID NO: 31, SEQ ID NO: 32 and SEQ ID NO:22, respectively; the light chain variable region comprises LCDR1, LCDR2 and LCDR3 having amino acid sequences of SEQ ID NO: 23, SEQ ID NO: 40 and SEQ ID NO:25, respectively;

the heavy chain variable region comprises HCDR1, HCDR2 and HCDR3 having amino acid sequences of SEQ ID NO: 31, SEQ ID NO: 32 and SEQ ID NO:22, respectively; the light chain variable region comprises LCDR1, LCDR2 and LCDR3 having amino acid sequences of SEQ ID NO: 23, SEQ ID NO: 67 and SEQ ID NO:25, respectively;

the heavy chain variable region comprises HCDR1, HCDR2 and HCDR3 having amino acid sequences of SEQ ID NO: 31, SEQ ID NO: 32 and SEQ ID NO:22, respectively; the light chain variable region comprises LCDR1, LCDR2 and LCDR3 having amino acid sequences of SEQ ID NO: 23, SEQ ID NO: 69 and SEQ ID NO:25, respectively;

the heavy chain variable region comprises HCDR1, HCDR2 and HCDR3 having amino acid sequences of SEQ ID NO: 31, SEQ ID NO: 32 and SEQ ID NO:22, respectively; the light chain variable region comprises LCDR1, LCDR2 and LCDR3 having amino acid sequences of SEQ ID NO: 23, SEQ ID NO: 41 and SEQ ID NO:25, respectively;

the heavy chain variable region comprises HCDR1, HCDR2 and HCDR3 having amino acid sequences of SEQ ID NO: 30, SEQ ID NO: 35 and SEQ ID NO:22, respectively; the light chain variable region comprises LCDR1, LCDR2 and LCDR3 having amino acid sequences of SEQ ID NO: 23, SEQ ID NO: 40 and SEQ ID NO:25, respectively;

the heavy chain variable region comprises HCDR1, HCDR2 and HCDR3 having amino acid sequences of SEQ ID NO: 30, SEQ ID NO: 36 and SEQ ID NO:22, respectively; the light chain variable region comprises LCDR1, LCDR2 and LCDR3 having amino acid sequences of SEQ ID NO: 23, SEQ ID NO: 40 and SEQ ID NO:25, respectively; or the heavy chain variable region comprises HCDR1, HCDR2 and HCDR3 having amino acid sequences of SEQ ID NO: 30, SEQ ID NO: 37 and SEQ ID NO:22, respectively; the light chain variable region comprises LCDR1, LCDR2 and LCDR3 having amino acid sequences of SEQ ID NO: 23, SEQ ID NO: 40 and SEQ ID NO:25, respectively.

4. The monoclonal antibody or the antigen-binding fragment thereof of claim 1, wherein the monoclonal antibody or antigen-binding fragment comprises:

the heavy chain variable region having an amino acid sequence of SEQ ID NO: 17 and the light chain variable region having an amino acid sequence of SEQ ID NO: 19;

the heavy chain variable region having an amino acid sequence of SEQ ID NO: 18 and the light chain variable region having an amino acid sequence of SEQ ID NO: 19; or the heavy chain variable region having an amino acid sequence of SEQ ID NO: 26 and the light chain variable region having an amino acid sequence of SEQ ID NO: 27.

5. The monoclonal antibody or the antigen-binding fragment thereof of claim 4, wherein the monoclonal antibody or the antigen-binding fragment comprises:

the heavy chain variable region having an amino acid sequence of SEQ ID NO: 42 and the light chain variable region having an amino acid sequence of SEQ ID NO: 45;

the heavy chain variable region having an amino acid sequence of SEQ ID NO: 43 and the light chain variable region having an amino acid sequence of SEQ ID NO: 45;

the heavy chain variable region having an amino acid sequence of SEQ ID NO: 44 and the light chain variable region having an amino acid sequence of SEQ ID NO: 45;

the heavy chain variable region having an amino acid sequence of SEQ ID NO: 46 and the light chain variable region having amino acid sequence of any one of SEQ ID NOs: 55, 56, 57, 70 and 72;

the heavy chain variable region having an amino acid sequence of SEQ ID NO: 47 and the light chain variable region having amino acid sequence of any one of SEQ ID NOs: 55, 56, 57, 70 and 72;

the heavy chain variable region having an amino acid sequence of SEQ ID NO: 48 and the light chain variable region having amino acid sequence of any one of SEQ ID NOs: 55, 56, 57, 70 and 72;

the heavy chain variable region having an amino acid sequence of SEQ ID NO: 49 and the light chain variable region having amino acid sequence of any one of SEQ ID NOs: 55, 56, 57, 70 and 72;

the heavy chain variable region having an amino acid sequence of SEQ ID NO: 50 and the light chain variable region having amino acid sequence of any one of SEQ ID NOs: 55, 56, 57, 70 and 72;

the heavy chain variable region having an amino acid sequence of SEQ ID NO: 51 and the light chain variable region having amino acid sequence of any one of SEQ ID NOs: 55, 56, 57, 70 and 72;

the heavy chain variable region having an amino acid sequence of SEQ ID NO: 52 and the light chain variable region having amino acid sequence of any one of SEQ ID NOs: 55, 56, 57, 70 and 72;

the heavy chain variable region having an amino acid sequence of SEQ ID NO: 53 and the light chain variable region having amino acid sequence of any one of SEQ ID NOs: 55, 56, 57, 70 and 72;

the heavy chain variable region having an amino acid sequence of SEQ ID NO: 66 and the light chain variable region having amino acid sequence of any one of SEQ ID NOs: 55, 56, 57, 70 and 72.

6. The monoclonal antibody or the antigen-binding fragment thereof of claim 4, wherein the monoclonal antibody or the antigen-binding fragment comprises: the heavy chain variable region having an amino acid sequence of SEQ ID NO: 42 and the light chain variable region having an amino acid sequence of SEQ ID NO: 45.

7. The monoclonal antibody or the antigen-binding fragment thereof of claim 1, wherein the antibody is a full-length antibody, further comprising human antibody constant regions.

8. The monoclonal antibody or the antigen-binding fragment thereof of claim 7, wherein the heavy chain constant region of the human antibody constant regions is selected from constant regions of human IgG1, IgG2, IgG3, and IgG4 and conventional variants thereof, and the light chain constant region of the human antibody constant regions is selected from κ and λ chain constant regions of human antibody and conventional variants thereof.

9. The monoclonal antibody or the antigen-binding fragment thereof of claim 7, wherein the full-length antibody comprises a human antibody heavy chain constant region of SEQ ID NO: 58, 60, or 65 and a human light chain constant region of SEQ ID NO: 59.

10. The monoclonal antibody or the antigen-binding fragment thereof of claim 1, wherein the antigen-binding fragment is selected from the group consisting of Fab, Fab', F(ab')$_2$, single chain variable fragment (scFv), dimerized domain V (diabody), disulfide stabilized Fv (dsFv) and CDR-containing peptides.

11. A pharmaceutical composition comprising a therapeutically effective amount of the monoclonal antibody or the antigen-binding fragment thereof of claim 1, and one or more pharmaceutically acceptable carriers, diluents or excipients.

12. A nucleic acid molecule encoding the monoclonal antibody or the antigen-binding fragment thereof of claim 1.

13. A recombinant vector comprising the nucleic acid molecule of claim 12.

14. A host cell transformed with the recombinant vector of claim 13, wherein the host cell is selected from a prokaryotic cell and a eukaryotic cell.

15. A method for producing a monoclonal antibody or an antigen-binding fragment thereof, the method comprising culturing the host cell of claim 14 in a medium to produce and accumulate the monoclonal antibody or the antigen-binding fragment thereof and harvesting the monoclonal antibody or the antigen-binding fragment thereof from the culture.

16. A method for immunodetection or determination of human PD-L1, the method comprising contacting a sample comprising human PD-L1 with using the monoclonal antibody or the antigen-binding fragment thereof of claim 1, and detecting binding between the monoclonal antibody or the antigen-binding fragment thereof and the human PD-L 1.

17. A method for treating diseases associated with human PD-L1, wherein the method comprising administering to a subject in need thereof a pharmaceutically effective amount of the monoclonal antibody or the antigen-binding fragment thereof of claim 1, wherein the disease is:
   a tumor or a cancer; or
   PD-L1 positive squamous cell carcinoma, myeloma, small cell lung cancer, non-small cell lung cancer (NSCLC), head and neck squamous cell carcinoma (HNSCC), glioma, Hodgkin's lymphoma, Non-Hodgkin's lymphoma, diffuse large B-cell lymphoma (DLBCL), follicular lymphoma, acute lymphoblastic leukemia (ALL), acute myeloid leukemia (AML), chronic lymphocytic leukemia (CLL), chronic myeloid leukemia (CML), primary mediastinal large B-cell lymphoma, mantle cell lymphoma (MCL), small lymphocytic lymphoma (SLL), T-cell/histocyte-rich large B-cell lymphoma, multiple myeloma, myeloid cell leukelia -1 protein (Mcl-1), myelodysplastic syndrome (MDS), gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, gastric carcinoma, bone cancer, Ewing's sarcoma, cervical cancer, brain cancer, gastric carcinoma, bladder cancer, hepatocellular carcinoma, breast cancer, colon cancer, hepatocellular carcinoma (HCC), clear cell renal cell carcinoma (RCC), head and neck cancer, throat cancer, hepatobiliary cancer, central nervous system cancer, esophageal cancer, malignant pleural mesothelioma, systemic light chain amyloidosis, lymphoplasmacytic lymphoma, myelodysplastic syndrome, myeloproliferative tumor, neuroendocrine neoplasm, Merkel cell carcinoma, testicular cancer and skin cancer.

18. A method for treating diseases associated with human PD-L1, the method comprising administering to a subject the pharmaceutical composition of claim 11 for treating diseases associated with human PD-L1, wherein the disease is:
   a tumor or a cancer; or
   PD-L1 positive squamous cell carcinoma, myeloma, small cell lung cancer, non-small cell lung cancer (NSCLC), head and neck squamous cell carcinoma (HNSCC), glioma, Hodgkin's lymphoma, Non-Hodgkin's lymphoma, diffuse large B-cell lymphoma (DLBCL), follicular lymphoma, acute lymphoblastic leukemia (ALL), acute myeloid leukemia (AML), chronic lymphocytic leukemia (CLL), chronic myeloid leukemia (CML), primary mediastinal large B-cell lymphoma, mantle cell lymphoma (MCL), small lymphocytic lymphoma (SLL), T-cell/histocyte-rich large B-cell lymphoma, multiple myeloma, myeloid cell leukelia -1 protein (Mcl-1), myelodysplastic syndrome (MDS), gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, gastric carcinoma, bone cancer, Ewing's sarcoma, cervical cancer, brain cancer, gastric carcinoma, bladder cancer, hepatocellular carcinoma, breast cancer, colon cancer, hepatocellular carcinoma (HCC), clear cell renal cell carcinoma (RCC), head and neck cancer, throat cancer, hepatobiliary cancer, central nervous system cancer, esophageal cancer, malignant pleural mesothelioma, systemic light chain amyloidosis, lymphoplasmacytic lymphoma, myelodysplastic syndrome, myeloproliferative tumor, neuroendocrine neoplasm, Merkel cell carcinoma, testicular cancer, and skin cancer.

19. A method for treating diseases associated with human PD-L1, the method comprising administering to a subject the nucleic acid molecule of claim 12 for treating diseases associated with human PD-L1, wherein the disease is:
   a tumor or a cancer; or
   PD-L1 positive squamous cell carcinoma, myeloma, small cell lung cancer, non-small cell lung cancer (NSCLC), head and neck squamous cell carcinoma (HNSCC), glioma, Hodgkin's lymphoma, Non-Hodgkin's lymphoma, diffuse large B-cell lymphoma (DLBCL), follicular lymphoma, acute lymphoblastic leukemia (ALL), acute myeloid leukemia (AML), chronic lymphocytic leukemia (CLL), chronic myeloid leukemia (CML), primary mediastinal large B-cell lymphoma, mantle cell lymphoma (MCL), small lymphocytic lymphoma (SLL), T-cell/histocyte-rich large B-cell lymphoma, multiple myeloma, myeloid cell leukelia -1 protein (Mcl-1), myelodysplastic syndrome (MDS), gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, gastric carcinoma, bone cancer, Ewing's sarcoma, cervical cancer, brain cancer, gastric carcinoma, bladder cancer, hepatocellular carcinoma, breast cancer, colon cancer, hepatocellular carcinoma (HCC), clear cell renal cell carcinoma (RCC), head and neck cancer, throat cancer, hepatobiliary cancer, central nervous system cancer, esophageal cancer, malignant pleural mesothelioma, systemic light chain amyloidosis, lymphoplasmacytic lymphoma, myelodysplastic syndrome, myeloproliferative tumor, neuroendocrine neoplasm, Merkel cell carcinoma, testicular cancer and skin cancer.

20. A method of inhibiting proliferation of PD-L1+cells, comprising: contacting cells expressing human PD-L1 with the monoclonal antibody or the antigen-binding fragment thereof of claim 1, wherein the monoclonal antibody or the antigen-binding fragment thereof mediates an ADCC effect, thereby inhibiting the proliferation of the cells expressing human PD-L1.

* * * * *

SEQUENCE LISTING

```
<160> NUMBER OF SEQ ID NOS: 72

<210> SEQ ID NO 1
<211> LENGTH: 445
<212> TYPE: PRT
<213> ORGANISM: Artificial Sequence
<220> FEATURE:
<223> OTHER INFORMATION: HRP00049 antibody heavy chain sequence

<400> SEQUENCE: 1

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Asp
            20                  25                  30

Tyr Trp Thr Trp Ile Arg Gln His Pro Gly Lys Gly Leu Glu Tyr Ile
        35                  40                  45

Gly Tyr Ile Ser Tyr Thr Gly Ser Thr Tyr Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Gly Gly Trp Leu Ala Pro Phe Asp Tyr Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
```

| | | | | |
|---|---|---|---|---|
| 305 | 310 | | 315 | 320 |

Val Ser Asn Lys Gly Leu Pro Ser Ser Ile Glu Lys Thr Ile Ser Lys
                          325                              330                        335

Ala Lys Gly Gln Pro Arg Glu Pro Gln Val Tyr Thr Leu Pro Pro Ser
                        340                              345                        350

Gln Glu Glu Met Thr Lys Asn Gln Val Ser Leu Thr Cys Leu Val Lys
                355                              360                        365

Gly Phe Tyr Pro Ser Asp Ile Ala Val Glu Trp Glu Ser Asn Gly Gln
  370                              375                              380

Pro Glu Asn Asn Tyr Lys Thr Thr Pro Pro Val Leu Asp Ser Asp Gly
385                            390                              395                        400

Ser Phe Phe Leu Tyr Ser Arg Leu Thr Val Asp Lys Ser Arg Trp Gln
                        405                              410                        415

Glu Gly Asn Val Phe Ser Cys Ser Val Met His Glu Ala Leu His Asn
                    420                              425                        430

His Tyr Thr Gln Lys Ser Leu Ser Leu Ser Leu Gly Lys
                  435                            440                        445

<210> SEQ ID NO 2
<211> LENGTH: 1338
<212> TYPE: DNA
<213> ORGANISM: Artificial Sequence
<220> FEATURE:
<223> OTHER INFORMATION: The gene sequence encoding HRP00049 antibody
     heavy chain

<400> SEQUENCE: 2

| | |
|---|---|
| caggtgcaac tgcaggagag cggccccgga ctcgtgaaac cctcccagac cctgagcctg | 60 |
| acctgtaccg tgagcggcgg cagcatcagc aacgactact ggacttggat caggcagcac | 120 |
| cccggcaaag gcctggagta catcggctac atcagctaca ccggctccac ctactacaac | 180 |
| cccagcctga gtccagggt gaccatcagc cgggacacca gcaagaacca gttcagcctg | 240 |
| aagctgagca gcgtgaccgc tgccgacaca gccgtgtact attgtgccag aagcggcgga | 300 |
| tggctggccc ctttcgacta ctggggcaga ggcaccctgg tgaccgtgag cagcgcttcc | 360 |
| accaagggcc catcggtctt ccccctggcg ccctgctcca ggagcacctc cgagagcaca | 420 |
| gccgccctgg gctgcctggt caaggactac ttccccgaac cggtgacggt gtcgtggaac | 480 |
| tcaggcgccc tgaccagcgg cgtgcacacc ttcccggctg tcctacagtc ctcaggactc | 540 |
| tactccctca gcagcgtggt gaccgtgccc tccagcagct tgggcacgaa gacctacacc | 600 |
| tgcaacgtag atcacaagcc cagcaacacc aaggtggaca gagagttga gtccaaatat | 660 |
| ggtcccccat gcccaccatg cccagcacct gaggctgctg gggaccatc agtcttcctg | 720 |
| ttccccccaa aacccaagga cactctcatg atctcccgga cccctgaggt cacgtgcgtg | 780 |
| gtggtggacg tgagccagga agaccccgag gtccagttca actggtacgt ggatggcgtg | 840 |
| gaggtgcata atgccaagac aaagccgcgg gaggagcagt tcaacagcac gtaccgtgtg | 900 |
| gtcagcgtcc tcaccgtcct gcaccaggac tggctgaacg gcaaggagta caagtgcaag | 960 |
| gtctccaaca aaggcctccc gtcctccatc gagaaaacca tctccaaagc caaagggcag | 1020 |
| ccccgagagc cacaggtgta caccctgccc catcccagg aggagatgac caagaaccag | 1080 |
| gtcagcctga cctgcctggt caaaggcttc taccccagcg acatcgccgt ggagtgggag | 1140 |
| agcaatgggc agccggagaa caactacaag accacgcctc ccgtgctgga ctccgacggc | 1200 |
| tccttcttcc tctacagcag gctcaccgtg gacaagagca ggtggcagga ggggaatgtc | 1260 |

```
ttctcatgct ccgtgatgca tgaggctctg cacaaccact acacacagaa gagcctctcc    1320
ctgtctctgg gtaaatga                                                   1338
```

<210> SEQ ID NO 3
<211> LENGTH: 220
<212> TYPE: PRT
<213> ORGANISM: Artificial Sequence
<220> FEATURE:
<223> OTHER INFORMATION: HRP00049 antibody light chain sequence

<400> SEQUENCE: 3

```
Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Leu Phe Tyr His
            20                  25                  30

Ser Asn Gln Lys His Ser Leu Ala Trp Tyr Gln Lys Pro Gly Gln
        35                  40                  45

Pro Pro Lys Leu Leu Ile Tyr Gly Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Gly Tyr Pro Tyr Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 4
<211> LENGTH: 663
<212> TYPE: DNA
<213> ORGANISM: Artificial Sequence
<220> FEATURE:
<223> OTHER INFORMATION: The gene sequence encoding HRP00049 antibody
      light chain

<400> SEQUENCE: 4

```
gacatcgtga tgacccagag ccctgatagc ctggctgtga gcctgggcga gagagccacc     60
atcaactgca agagcagcca gagcctgttc taccatagca accagaagca cagcctcgcc    120
tggtatcagc agaagcccgg ccaaccccc aagctgctga tctacggcgc cagcacaaga    180
gagagcggag tgcccgatag gttcagcggc agcggatccg gcaccgattt caccctgacc    240
atcagcagcc tgcaggccga ggatgtggcc gtgtactact gccagcagta ctacggctac    300
ccttacacct tcggcggcgg caccaaggtg gagatcaagc gtacggtggc tgcaccatct    360
```

-continued

```
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga aacacaaagt ctacgcctgc      600
gaagtcaccc atcagggcct gagctcgccc gtcacaaaga gcttcaacag gggagagtgt      660
tga                                                                    663
```

<210> SEQ ID NO 5
<211> LENGTH: 446
<212> TYPE: PRT
<213> ORGANISM: Artificial Sequence
<220> FEATURE:
<223> OTHER INFORMATION: HRP00052 antibody heavy chain sequence

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Gly Pro Asn Ser Gly Phe Thr Ser Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ser Tyr Asp Tyr Phe Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

```
Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Gln Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 6
<211> LENGTH: 1341
<212> TYPE: DNA
<213> ORGANISM: Artificial Sequence
<220> FEATURE:
<223> OTHER INFORMATION: The gene sequence encoding HRP00052 antibody
      heavy chain

<400> SEQUENCE: 6
caggtgcaac tggtgcagag cggtgccgag gtgaagaagc ctggcgcaag cgtgaaagtg      60
agctgcaagg ccagcggcta caccttcacc agctactgga tgcactgggt gaggcaggcc     120
cctggacagg gcctggagtg gatgggcagg atcgggccca cagtggtttt cactagctac     180
aatgaaaagt tcaagaacag gtaaccatg accaggaca cctccaccag cacagtgtat      240
atggagctga gcagcctgag gagcgaggac accgccgtgt actactgtgc cagaggcggc     300
agcagctacg actacttcga ctattggggc cagggcacca ccgtgaccgt gagcagtgct     360
tccaccaagg gcccatcggt cttccccctg gcgccctgct ccaggagcac ctccgagagc     420
acagccgccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac gaagacctac     600
acctgcaacg tagatcacaa gcccagcaac accaaggtgg acaagagagt tgagtccaaa     660
tatggtcccc catgcccacc atgcccagca cctgaggctg ctgggggacc atcagtcttc     720
ctgttccccc caaaacccaa ggacactctc atgatctccc ggaccctga ggtcacgtgc      780 gtggtggtgg acgtgagcca ggaagacccc gaggtccagt tcaactggta cgtggatggc     840
gtggaggtgc ataatgccaa gacaaagccg cgggaggagc agttcaacag cacgtaccgt     900
gtggtcagcg tcctcaccgt cctgcaccag gactggctga acggcaagga gtacaagtgc     960
aaggtctcca acaaaggcct cccgtcctcc atcgagaaaa ccatctccaa agccaaaggg    1020
cagccccgag agccacaggt gtacaccctg cccccatccc aggaggagat gaccaagaac    1080
caggtcagcc tgacctgcct ggtcaaaggc ttctacccca gcgacatcgc cgtggagtgg    1140
gagagcaatg ggcagccgga gaacaactac aagaccacgc ctcccgtgct ggactccgac    1200
ggctccttct tcctctacag caggctcacc gtggacaaga gcaggtggca ggaggggaat    1260
```

```
gtcttctcat gctccgtgat gcatgaggct ctgcacaacc actacacaca gaagagcctc    1320
tccctgtctc tgggtaaatg a                                              1341
```

<210> SEQ ID NO 7
<211> LENGTH: 218
<212> TYPE: PRT
<213> ORGANISM: Artificial Sequence
<220> FEATURE:
<223> OTHER INFORMATION: HRP00052 antibody light chain sequence

<400> SEQUENCE: 7

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Glu Asp Thr Ala Asn Tyr Tyr Cys Gln Gln Ser Phe
                85                  90                  95

Glu Asp Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 8
<211> LENGTH: 657
<212> TYPE: DNA
<213> ORGANISM: Artificial Sequence
<220> FEATURE:
<223> OTHER INFORMATION: The gene sequence encoding HRP00052 antibody
      light chain

<400> SEQUENCE: 8

```
gacatcgtgc tgacccagag tcccgcctca cttgccgtga gccccggtca gagggccacc    60
atcacctgta gggccagcga gagcgtgagc atccacggca cccacctgat gcactggtat   120
caacagaaac ccggccagcc ccccaaactg ctgatctacg ccgccagcaa cctggagagc   180
ggcgtgcccg ccaggttcag cggctccggc agcggcaccg acttcaccct cactatcaac   240
cccgtggagg ccgaggacac cgccaactac tactgccagc agagcttcga ggaccccctg   300
accttcggcc agggcaccaa gctggagatc aagcgtacgg tggctgcacc atctgtcttc   360
```

```
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc    600 acccatcagg gcctgagctc gcccgtcaca aagagcttca cagggggaga gtgttga    657
```

<210> SEQ ID NO 9
<211> LENGTH: 401
<212> TYPE: PRT
<213> ORGANISM: Artificial Sequence
<220> FEATURE:
<223> OTHER INFORMATION: Human PD-L1-IgG1Fc

<400> SEQUENCE: 9

```
Met Glu Phe Gly Leu Ser Trp Leu Phe Leu Val Ala Ile Leu Lys Gly
1               5                   10                  15

Val Gln Cys Pro Gly Trp Phe Leu Asp Ser Pro Asp Arg Pro Trp Asn
            20                  25                  30

Pro Pro Thr Phe Ser Pro Ala Leu Leu Val Val Thr Glu Gly Asp Asn
        35                  40                  45

Ala Thr Phe Thr Cys Ser Phe Ser Asn Thr Ser Glu Ser Phe Val Leu
    50                  55                  60

Asn Trp Tyr Arg Met Ser Pro Ser Asn Gln Thr Asp Lys Leu Ala Ala
65                  70                  75                  80

Phe Pro Glu Asp Arg Ser Gln Pro Gly Gln Asp Cys Arg Phe Arg Val
                85                  90                  95

Thr Gln Leu Pro Asn Gly Arg Asp Phe His Met Ser Val Val Arg Ala
            100                 105                 110

Arg Arg Asn Asp Ser Gly Thr Tyr Leu Cys Gly Ala Ile Ser Leu Ala
        115                 120                 125

Pro Lys Ala Gln Ile Lys Glu Ser Leu Arg Ala Glu Leu Arg Val Thr
    130                 135                 140

Glu Arg Arg Ala Glu Val Pro Thr Ala His Pro Ser Pro Ser Pro Arg
145                 150                 155                 160

Pro Ala Gly Gln Phe Gln Thr Leu Val Glu Pro Lys Ser Ser Asp Lys
                165                 170                 175

Thr His Thr Cys Pro Pro Cys Pro Ala Pro Glu Leu Leu Gly Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
    210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Pro Ala Pro Ile Glu Lys
        275                 280                 285

Thr Ile Ser Lys Ala Lys Gly Gln Pro Arg Glu Pro Gln Val Tyr Thr
    290                 295                 300

Leu Pro Pro Ser Arg Asp Glu Leu Thr Lys Asn Gln Val Ser Leu Thr
```

```
                305                 310                 315                 320
Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Lys Leu Thr Val Asp Lys
        355                 360                 365

Ser Arg Trp Gln Gln Gly Asn Val Phe Ser Cys Ser Val Met His Glu
    370                 375                 380

Ala Leu His Asn His Tyr Thr Gln Lys Ser Leu Ser Leu Ser Pro Gly
385                 390                 395                 400

Lys

<210> SEQ ID NO 10
<211> LENGTH: 7
<212> TYPE: PRT
<213> ORGANISM: Artificial Sequence
<220> FEATURE:
<223> OTHER INFORMATION: HCDR1 sequence 1 of HRP00049 antibody

<400> SEQUENCE: 10

Asp Gly Ser Ala Tyr Trp Ser
1               5

<210> SEQ ID NO 11
<211> LENGTH: 5
<212> TYPE: PRT
<213> ORGANISM: Artificial Sequence
<220> FEATURE:
<223> OTHER INFORMATION: HCDR1 sequence 2 of HRP00049 antibody

<400> SEQUENCE: 11

Asn Asp Tyr Trp Thr
1               5

<210> SEQ ID NO 12
<211> LENGTH: 16
<212> TYPE: PRT
<213> ORGANISM: Artificial Sequence
<220> FEATURE:
<223> OTHER INFORMATION: General sequence formula of antibody HCDR2
      derived from HRP00049 antibody yeast display library
<220> FEATURE:
<221> NAME/KEY: UNSURE
<222> LOCATION: (1)..(1)
<223> OTHER INFORMATION: Xaa is selected from Phe or Met
<220> FEATURE:
<221> NAME/KEY: UNSURE
<222> LOCATION: (4)..(4)
<223> OTHER INFORMATION: Xaa is selected from Arg or Val
<220> FEATURE:
<221> NAME/KEY: UNSURE
<222> LOCATION: (10)..(10)
<223> OTHER INFORMATION: Xaa is selected from Asn or His

<400> SEQUENCE: 12

Xaa Ile Ser Xaa Ala Gly Ser Thr Tyr Xaa Thr Pro Ser Leu Lys Gly
1               5                   10                  15

<210> SEQ ID NO 13
<211> LENGTH: 10
<212> TYPE: PRT
<213> ORGANISM: Artificial Sequence
<220> FEATURE:
<223> OTHER INFORMATION: HCDR3 of HRP00049 antibody
```

```
<400> SEQUENCE: 13

Ser Gly Gly Trp Leu Ala Pro Phe Asp Tyr
1               5                   10

<210> SEQ ID NO 14
<211> LENGTH: 17
<212> TYPE: PRT
<213> ORGANISM: Artificial Sequence
<220> FEATURE:
<223> OTHER INFORMATION: LCDR1 of HRP00049 antibody

<400> SEQUENCE: 14

Lys Ser Ser Gln Ser Leu Phe Tyr His Ser Asn Gln Lys His Ser Leu
1               5                   10                  15

Ala

<210> SEQ ID NO 15
<211> LENGTH: 7
<212> TYPE: PRT
<213> ORGANISM: Artificial Sequence
<220> FEATURE:
<223> OTHER INFORMATION: LCDR2 of HRP00049 antibody

<400> SEQUENCE: 15

Gly Ala Ser Thr Arg Glu Ser
1               5

<210> SEQ ID NO 16
<211> LENGTH: 9
<212> TYPE: PRT
<213> ORGANISM: Artificial Sequence
<220> FEATURE:
<223> OTHER INFORMATION: LCDR3 of HRP00049 antibody

<400> SEQUENCE: 16

Gln Gln Tyr Tyr Gly Tyr Pro Tyr Thr
1               5

<210> SEQ ID NO 17
<211> LENGTH: 120
<212> TYPE: PRT
<213> ORGANISM: Artificial Sequence
<220> FEATURE:
<223> OTHER INFORMATION: General sequence formula of antibody heavy
      chain variable region derived from HRP00049 antibody yeast display
      library
<220> FEATURE:
<221> NAME/KEY: UNSURE
<222> LOCATION: (52)..(52)
<223> OTHER INFORMATION: Xaa is selected from Phe or Met
<220> FEATURE:
<221> NAME/KEY: UNSURE
<222> LOCATION: (55)..(55)
<223> OTHER INFORMATION: Xaa is selected from Arg or Val
<220> FEATURE:
<221> NAME/KEY: UNSURE
<222> LOCATION: (61)..(61)
<223> OTHER INFORMATION: Xaa is selected from Asn or His

<400> SEQUENCE: 17

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asp Gly
                20                  25                  30

Ser Ala Tyr Trp Ser Trp Ile Arg Gln His Pro Gly Lys Gly Leu Glu
            35                  40                  45
```

Tyr Ile Gly Xaa Ile Ser Xaa Ala Gly Ser Thr Tyr Xaa Thr Pro Ser
        50                  55                  60

Leu Lys Gly Arg Val Thr Ile Ser Arg Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Gly Gly Trp Leu Ala Pro Phe Asp Tyr Trp Gly Arg
            100                 105                 110

Gly Thr Leu Val Thr Val Ser Ser
            115                 120

<210> SEQ ID NO 18
<211> LENGTH: 118
<212> TYPE: PRT
<213> ORGANISM: Artificial Sequence
<220> FEATURE:
<223> OTHER INFORMATION: General sequence formula of antibody heavy
      chain variable region derived from HRP00049 antibody yeast display
      library
<220> FEATURE:
<221> NAME/KEY: UNSURE
<222> LOCATION: (50)..(50)
<223> OTHER INFORMATION: Xaa is selected from Phe or Met
<220> FEATURE:
<221> NAME/KEY: UNSURE
<222> LOCATION: (53)..(53)
<223> OTHER INFORMATION: Xaa is selected from Arg or Val
<220> FEATURE:
<221> NAME/KEY: UNSURE
<222> LOCATION: (59)..(59)
<223> OTHER INFORMATION: Xaa is selected from Asn or His

<400> SEQUENCE: 18

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Asp
                20                  25                  30

Tyr Trp Thr Trp Ile Arg Gln His Pro Gly Lys Gly Leu Glu Tyr Ile
            35                  40                  45

Gly Xaa Ile Ser Xaa Ala Gly Ser Thr Tyr Xaa Thr Pro Ser Leu Lys
        50                  55                  60

Gly Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Gly Gly Trp Leu Ala Pro Phe Asp Tyr Trp Gly Arg Gly Thr
            100                 105                 110

Leu Val Thr Val Ser Ser
        115

<210> SEQ ID NO 19
<211> LENGTH: 113
<212> TYPE: PRT
<213> ORGANISM: Artificial Sequence
<220> FEATURE:
<223> OTHER INFORMATION: Light chain variable region of HRP00049
      antibody

<400> SEQUENCE: 19

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Tyr His
                20                  25                  30

```
Ser Asn Gln Lys His Ser Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Gly Tyr Pro Tyr Thr Phe Gly Gly Gly Thr Lys Val Glu Ile
               100                 105                 110

Lys

<210> SEQ ID NO 20
<211> LENGTH: 5
<212> TYPE: PRT
<213> ORGANISM: Artificial Sequence
<220> FEATURE:
<223> OTHER INFORMATION: General sequence formula of antibody HCDR1
      derived from HRP00052 antibody yeast display library
<220> FEATURE:
<221> NAME/KEY: UNSURE
<222> LOCATION: (1)..(1)
<223> OTHER INFORMATION: Xaa is selected from Ser and Asp
<220> FEATURE:
<221> NAME/KEY: UNSURE
<222> LOCATION: (2)..(2)
<223> OTHER INFORMATION: Xaa is selected from Tyr and Lys
<220> FEATURE:
<221> NAME/KEY: UNSURE
<222> LOCATION: (5)..(5)
<223> OTHER INFORMATION: Xaa is selected from His and Met

<400> SEQUENCE: 20

Xaa Xaa Trp Met Xaa
 1               5

<210> SEQ ID NO 21
<211> LENGTH: 17
<212> TYPE: PRT
<213> ORGANISM: Artificial Sequence
<220> FEATURE:
<223> OTHER INFORMATION: General sequence formula of antibody HCDR2
      derived from HRP00052 antibody yeast display library
<220> FEATURE:
<221> NAME/KEY: UNSURE
<222> LOCATION: (3)..(3)
<223> OTHER INFORMATION: Xaa is selected from ThrSerHis and Gly
<220> FEATURE:
<221> NAME/KEY: UNSURE
<222> LOCATION: (5)..(5)
<223> OTHER INFORMATION: Xaa is selected from SerAsn and Gly
<220> FEATURE:
<221> NAME/KEY: UNSURE
<222> LOCATION: (6)..(6)
<223> OTHER INFORMATION: Xaa is selected from SerLeu and Gly
<220> FEATURE:
<221> NAME/KEY: UNSURE
<222> LOCATION: (8)..(8)
<223> OTHER INFORMATION: Xaa is selected from PheLeuTrp and Met
<220> FEATURE:
<221> NAME/KEY: UNSURE
<222> LOCATION: (9)..(9)
<223> OTHER INFORMATION: Xaa is selected from AlaPro and Thr
<220> FEATURE:
<221> NAME/KEY: UNSURE
<222> LOCATION: (10)..(10)
<223> OTHER INFORMATION: Xaa is selected from MetValLeu and Ser
<220> FEATURE:
<221> NAME/KEY: UNSURE
<222> LOCATION: (15)..(15)
```

```
<223> OTHER INFORMATION: Xaa is selected from Phe and Tyr

<400> SEQUENCE: 21

Arg Ile Xaa Pro Xaa Xaa Gly Xaa Xaa Xaa Tyr Asn Glu Lys Xaa Lys
1               5                   10                  15

Asn

<210> SEQ ID NO 22
<211> LENGTH: 10
<212> TYPE: PRT
<213> ORGANISM: Artificial Sequence
<220> FEATURE:
<223> OTHER INFORMATION: HCDR3 sequence of HRP00052 antibody

<400> SEQUENCE: 22

Gly Gly Ser Ser Tyr Asp Tyr Phe Asp Tyr
1               5                   10

<210> SEQ ID NO 23
<211> LENGTH: 15
<212> TYPE: PRT
<213> ORGANISM: Artificial Sequence
<220> FEATURE:
<223> OTHER INFORMATION: LCDR1 sequence of HRP00052 antibody

<400> SEQUENCE: 23

Arg Ala Ser Glu Ser Val Ser Ile His Gly Thr His Leu Met His
1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: General sequence formula of antibody LCDR2
      derived from HRP00052 antibody yeast display library
<220> FEATURE:
<221> NAME/KEY: UNSURE
<222> LOCATION: (1)..(1)
<223> OTHER INFORMATION: Xaa is selected from Val and Ala
<220> FEATURE:
<221> NAME/KEY: UNSURE
<222> LOCATION: (4)..(4)
<223> OTHER INFORMATION: Xaa is selected from Tyr and Asn
<220> FEATURE:
<221> NAME/KEY: UNSURE
<222> LOCATION: (5)..(5)
<223> OTHER INFORMATION: Xaa is selected from AlaLeu and Val
<220> FEATURE:
<221> NAME/KEY: UNSURE
<222> LOCATION: (6)..(6)
<223> OTHER INFORMATION: Xaa is selected from GluPheTrp,Tyr and Ala

<400> SEQUENCE: 24

Xaa Ala Ser Xaa Xaa Xaa Ser
1               5

<210> SEQ ID NO 25
<211> LENGTH: 9
<212> TYPE: PRT
<213> ORGANISM: Artificial Sequence
<220> FEATURE:
<223> OTHER INFORMATION: LCDR3 sequence of HRP00052 antibody

<400> SEQUENCE: 25

Gln Gln Ser Phe Glu Asp Pro Leu Thr
1               5
```

-continued

```
<210> SEQ ID NO 26
<211> LENGTH: 119
<212> TYPE: PRT
<213> ORGANISM: Artificial Sequence
<220> FEATURE:
<223> OTHER INFORMATION: General sequence formula of antibody heavy
      chain variable region derived from HRP00052 antibody yeast display
      library
<220> FEATURE:
<221> NAME/KEY: UNSURE
<222> LOCATION: (31)..(31)
<223> OTHER INFORMATION: Xaa is selected from Ser and Asp
<220> FEATURE:
<221> NAME/KEY: UNSURE
<222> LOCATION: (32)..(32)
<223> OTHER INFORMATION: Xaa is selected from Tyr and Lys
<220> FEATURE:
<221> NAME/KEY: UNSURE
<222> LOCATION: (35)..(35)
<223> OTHER INFORMATION: Xaa is selected from His and Met
<220> FEATURE:
<221> NAME/KEY: UNSURE
<222> LOCATION: (52)..(52)
<223> OTHER INFORMATION: Xaa is selected from ThrSerHis and Gly
<220> FEATURE:
<221> NAME/KEY: UNSURE
<222> LOCATION: (54)..(54)
<223> OTHER INFORMATION: Xaa is selected from SerAsn and Gly
<220> FEATURE:
<221> NAME/KEY: UNSURE
<222> LOCATION: (55)..(55)
<223> OTHER INFORMATION: Xaa is selected from SerLeu and Gly
<220> FEATURE:
<221> NAME/KEY: UNSURE
<222> LOCATION: (57)..(57)
<223> OTHER INFORMATION: Xaa is selected from PheLeuTrp and Met
<220> FEATURE:
<221> NAME/KEY: UNSURE
<222> LOCATION: (58)..(58)
<223> OTHER INFORMATION: Xaa is selected from AlaPro and Thr
<220> FEATURE:
<221> NAME/KEY: UNSURE
<222> LOCATION: (59)..(59)
<223> OTHER INFORMATION: Xaa is selected from MetValLeu and Ser
<220> FEATURE:
<221> NAME/KEY: UNSURE
<222> LOCATION: (64)..(64)
<223> OTHER INFORMATION: Xaa is selected from Phe and Tyr

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Xaa Xaa
            20                  25                  30

Trp Met Xaa Trp Val Arg Gln Ala Pro Gly Gln Gly Leu Glu Trp Met
        35                  40                  45

Gly Arg Ile Xaa Pro Xaa Xaa Gly Xaa Xaa Xaa Tyr Asn Glu Lys Xaa
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ser Tyr Asp Tyr Phe Asp Tyr Trp Gly Gln Gly
            100                 105                 110

Thr Thr Val Thr Val Ser Ser
        115

<210> SEQ ID NO 27
<211> LENGTH: 111
<212> TYPE: PRT
```

```
<213> ORGANISM: Artificial Sequence
<220> FEATURE:
<223> OTHER INFORMATION: General sequence formula of antibody light
      chain variable region derived from HRP00052 antibody yeast display
      library
<220> FEATURE:
<221> NAME/KEY: UNSURE
<222> LOCATION: (54)..(54)
<223> OTHER INFORMATION: Xaa is selected from Val and Ala
<220> FEATURE:
<221> NAME/KEY: UNSURE
<222> LOCATION: (57)..(57)
<223> OTHER INFORMATION: Xaa is selected from Tyr and Asn
<220> FEATURE:
<221> NAME/KEY: UNSURE
<222> LOCATION: (58)..(58)
<223> OTHER INFORMATION: Xaa is selected from AlaLeu and Val
<220> FEATURE:
<221> NAME/KEY: UNSURE
<222> LOCATION: (59)..(59)
<223> OTHER INFORMATION: Xaa is selected from GluPheTrpTyr and Ala

<400> SEQUENCE: 27

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Xaa Ala Ser Xaa Xaa Xaa Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Glu Asp Thr Ala Asn Tyr Tyr Cys Gln Gln Ser Phe
                85                  90                  95

Glu Asp Pro Leu Thr Phe Gly Gln Gly Thr Lys Leu Glu Ile Lys
            100                 105                 110

<210> SEQ ID NO 28
<211> LENGTH: 16
<212> TYPE: PRT
<213> ORGANISM: Artificial Sequence
<220> FEATURE:
<223> OTHER INFORMATION: HCDR2 sequence of 9-2 H5

<400> SEQUENCE: 28

Phe Ile Ser Arg Ala Gly Ser Thr Tyr Asn Thr Pro Ser Leu Lys Gly
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: HCDR2 sequence of 9-2 H7

<400> SEQUENCE: 29

Met Ile Ser Val Ala Gly Ser Thr Tyr His Thr Pro Ser Leu Lys Gly
1               5                   10                  15

<210> SEQ ID NO 30
<211> LENGTH: 5
<212> TYPE: PRT
<213> ORGANISM: Artificial Sequence
<220> FEATURE:
<223> OTHER INFORMATION: HCDR1 sequence of 24D5 H12
```

<400> SEQUENCE: 30

Ser Tyr Trp Met His
1               5

<210> SEQ ID NO 31
<211> LENGTH: 5
<212> TYPE: PRT
<213> ORGANISM: Artificial Sequence
<220> FEATURE:
<223> OTHER INFORMATION: HCDR1 sequence of 24D5 H15

<400> SEQUENCE: 31

Asp Lys Trp Met Met
1               5

<210> SEQ ID NO 32
<211> LENGTH: 17
<212> TYPE: PRT
<213> ORGANISM: Artificial Sequence
<220> FEATURE:
<223> OTHER INFORMATION: HCDR2 sequence of 24D5 H12

<400> SEQUENCE: 32

Arg Ile Thr Pro Ser Ser Gly Phe Ala Met Tyr Asn Glu Lys Phe Lys
1               5                   10                  15
Asn

<210> SEQ ID NO 33
<211> LENGTH: 17
<212> TYPE: PRT
<213> ORGANISM: Artificial Sequence
<220> FEATURE:
<223> OTHER INFORMATION: HCDR2 sequence of 24D5 H13

<400> SEQUENCE: 33

Arg Ile Ser Pro Ser Leu Gly Leu Ala Val Tyr Asn Glu Lys Phe Lys
1               5                   10                  15
Asn

<210> SEQ ID NO 34
<211> LENGTH: 17
<212> TYPE: PRT
<213> ORGANISM: Artificial Sequence
<220> FEATURE:
<223> OTHER INFORMATION: HCDR2 sequence of 24D5 H14

<400> SEQUENCE: 34

Arg Ile His Pro Ser Leu Gly Leu Pro Leu Tyr Asn Glu Lys Phe Lys
1               5                   10                  15
Asn

<210> SEQ ID NO 35
<211> LENGTH: 17
<212> TYPE: PRT
<213> ORGANISM: Artificial Sequence
<220> FEATURE:
<223> OTHER INFORMATION: HCDR2 sequence of 24D5 H17

<400> SEQUENCE: 35

Arg Ile Gly Pro Asn Leu Gly Trp Ala Met Tyr Asn Glu Lys Tyr Lys
1               5                   10                  15
Asn

```
<210> SEQ ID NO 36
<211> LENGTH: 17
<212> TYPE: PRT
<213> ORGANISM: Artificial Sequence
<220> FEATURE:
<223> OTHER INFORMATION: HCDR2 sequence of 24D5 H18

<400> SEQUENCE: 36

Arg Ile Ser Pro Ser Ser Gly Met Ala Val Tyr Asn Glu Lys Phe Lys
1               5                   10                  15

Asn

<210> SEQ ID NO 37
<211> LENGTH: 17
<212> TYPE: PRT
<213> ORGANISM: Artificial Sequence
<220> FEATURE:
<223> OTHER INFORMATION: HCDR2 sequence of 24D5 H19

<400> SEQUENCE: 37

Arg Ile Ser Pro Gly Gly Gly Phe Thr Leu Tyr Asn Glu Lys Phe Lys
1               5                   10                  15

Asn

<210> SEQ ID NO 38
<211> LENGTH: 17
<212> TYPE: PRT
<213> ORGANISM: Artificial Sequence
<220> FEATURE:
<223> OTHER INFORMATION: HCDR3 sequence of 24D5 H20

<400> SEQUENCE: 38

Arg Ile Gly Pro Asn Ser Gly Phe Thr Ser Tyr Asn Glu Lys Phe Lys
1               5                   10                  15

Asn

<210> SEQ ID NO 39
<211> LENGTH: 7
<212> TYPE: PRT
<213> ORGANISM: Artificial Sequence
<220> FEATURE:
<223> OTHER INFORMATION: LCDR2 sequence of 24D5 L64

<400> SEQUENCE: 39

Val Ala Ser Tyr Ala Ala Ser
1               5

<210> SEQ ID NO 40
<211> LENGTH: 7
<212> TYPE: PRT
<213> ORGANISM: Artificial Sequence
<220> FEATURE:
<223> OTHER INFORMATION: LCDR2 sequence of 24D5 L61

<400> SEQUENCE: 40

Ala Ala Ser Asn Leu Glu Ser
1               5

<210> SEQ ID NO 41
<211> LENGTH: 7
<212> TYPE: PRT
<213> ORGANISM: Artificial Sequence
<220> FEATURE:
<223> OTHER INFORMATION: LCDR2 sequence of 24D5 L66

<400> SEQUENCE: 41
```

Val Ala Ser Asn Val Phe Ser
1               5

<210> SEQ ID NO 42
<211> LENGTH: 120
<212> TYPE: PRT
<213> ORGANISM: Artificial Sequence
<220> FEATURE:
<223> OTHER INFORMATION: Heavy chain variable region of 9-2 H5

<400> SEQUENCE: 42

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asp Gly
            20                  25                  30

Ser Ala Tyr Trp Ser Trp Ile Arg Gln His Pro Gly Lys Gly Leu Glu
        35                  40                  45

Tyr Ile Gly Phe Ile Ser Arg Ala Gly Ser Thr Tyr Asn Thr Pro Ser
    50                  55                  60

Leu Lys Gly Arg Val Thr Ile Ser Arg Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Gly Gly Trp Leu Ala Pro Phe Asp Tyr Trp Gly Arg
            100                 105                 110

Gly Thr Leu Val Thr Val Ser Ser
        115                 120

<210> SEQ ID NO 43
<211> LENGTH: 118
<212> TYPE: PRT
<213> ORGANISM: Artificial Sequence
<220> FEATURE:
<223> OTHER INFORMATION: Heavy chain variable region of 9-2 H6

<400> SEQUENCE: 43

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Asp
            20                  25                  30

Tyr Trp Thr Trp Ile Arg Gln His Pro Gly Lys Gly Leu Glu Tyr Ile
        35                  40                  45

Gly Phe Ile Ser Arg Ala Gly Ser Thr Tyr Asn Thr Pro Ser Leu Lys
    50                  55                  60

Gly Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Gly Gly Trp Leu Ala Pro Phe Asp Tyr Trp Gly Arg Gly Thr
            100                 105                 110

Leu Val Thr Val Ser Ser
        115

<210> SEQ ID NO 44
<211> LENGTH: 118
<212> TYPE: PRT
<213> ORGANISM: Artificial Sequence
<220> FEATURE:
<223> OTHER INFORMATION: Heavy chain variable region of 9-2 H7

<400> SEQUENCE: 44

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Asp
            20                  25                  30

Tyr Trp Thr Trp Ile Arg Gln His Pro Gly Lys Gly Leu Glu Tyr Ile
        35                  40                  45

Gly Met Ile Ser Val Ala Gly Ser Thr Tyr His Thr Pro Ser Leu Lys
50                  55                  60

Gly Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Gly Gly Trp Leu Ala Pro Phe Asp Tyr Trp Gly Arg Gly Thr
            100                 105                 110

Leu Val Thr Val Ser Ser
        115

<210> SEQ ID NO 45
<211> LENGTH: 113
<212> TYPE: PRT
<213> ORGANISM: Artificial Sequence
<220> FEATURE:
<223> OTHER INFORMATION: Light chain variable region of 9-2 L11

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Tyr His
            20                  25                  30

Ser Asn Gln Lys His Ser Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Gly Tyr Pro Tyr Thr Phe Gly Gly Gly Thr Lys Val Glu Ile
            100                 105                 110

Lys

<210> SEQ ID NO 46
<211> LENGTH: 119
<212> TYPE: PRT
<213> ORGANISM: Artificial Sequence
<220> FEATURE:
<223> OTHER INFORMATION: Heavy chain variable region of 24D5 H12

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

```
Gly Arg Ile Thr Pro Ser Ser Gly Phe Ala Met Tyr Asn Glu Lys Phe
        50                  55                  60

Lys Asn Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Gly Ser Ser Tyr Asp Tyr Phe Asp Tyr Trp Gly Gln Gly
            100                 105                 110

Thr Thr Val Thr Val Ser Ser
        115

<210> SEQ ID NO 47
<211> LENGTH: 119
<212> TYPE: PRT
<213> ORGANISM: Artificial Sequence
<220> FEATURE:
<223> OTHER INFORMATION: Heavy chain variable region of 24D5 H13

<400> SEQUENCE: 47

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Ser Pro Ser Leu Gly Leu Ala Val Tyr Asn Glu Lys Phe
        50                  55                  60

Lys Asn Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Gly Ser Ser Tyr Asp Tyr Phe Asp Tyr Trp Gly Gln Gly
            100                 105                 110

Thr Thr Val Thr Val Ser Ser
        115

<210> SEQ ID NO 48
<211> LENGTH: 119
<212> TYPE: PRT
<213> ORGANISM: Artificial Sequence
<220> FEATURE:
<223> OTHER INFORMATION: Heavy chain variable region of 24D5 H14

<400> SEQUENCE: 48

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile His Pro Ser Leu Gly Leu Pro Leu Tyr Asn Glu Lys Phe
        50                  55                  60

Lys Asn Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Gly Ser Ser Tyr Asp Tyr Phe Asp Tyr Trp Gly Gln Gly
            100                 105                 110
```

Thr Thr Val Thr Val Ser Ser
        115

<210> SEQ ID NO 49
<211> LENGTH: 119
<212> TYPE: PRT
<213> ORGANISM: Artificial Sequence
<220> FEATURE:
<223> OTHER INFORMATION: Heavy chain variable region of 24D5 H15

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Asn Gly Tyr Thr Phe Thr Asp Lys
                20                  25                  30

Trp Met Met Trp Val Arg Gln Ala Pro Gly Gln Gly Leu Glu Trp Met
            35                  40                  45

Gly Arg Ile Thr Pro Ser Ser Gly Phe Ala Met Tyr Asn Glu Lys Phe
        50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ser Tyr Asp Tyr Phe Asp Tyr Trp Gly Gln Gly
            100                 105                 110

Thr Thr Val Thr Val Ser Ser
        115

<210> SEQ ID NO 50
<211> LENGTH: 119
<212> TYPE: PRT
<213> ORGANISM: Artificial Sequence
<220> FEATURE:
<223> OTHER INFORMATION: Heavy chain variable region of 24D5 H16

<400> SEQUENCE: 50

Gln Val Gln Leu Val Gln Ser Gly Ala Glu Val Lys Lys Pro Gly Ala
1               5                   10                  15

Ser Met Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Arg Ile Ser Pro Ser Leu Gly Leu Ala Val Tyr Asn Glu Lys Phe
        50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ser Tyr Asp Tyr Phe Asp Tyr Trp Gly Gln Gly
            100                 105                 110

Thr Thr Val Thr Val Ser Ser
        115

<210> SEQ ID NO 51
<211> LENGTH: 119
<212> TYPE: PRT
<213> ORGANISM: Artificial Sequence
<220> FEATURE:
<223> OTHER INFORMATION: Heavy chain variable region of 24D5 H17

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Gly Pro Asn Leu Gly Trp Ala Met Tyr Asn Glu Lys Tyr
    50                  55                  60

Lys Asn Arg Val Thr Met Thr Arg Asp Thr Ser Thr Ser Thr Val Tyr
65                  70                  75                  80

Met Glu Leu Ser Ser Leu Gly Ser Glu Asp Thr Ala Val Tyr Tyr Cys
                85                  90                  95

Ala Arg Gly Gly Ser Ser Tyr Asp Tyr Phe Asp Tyr Trp Gly Gln Gly
            100                 105                 110

Thr Thr Val Thr Val Ser Ser
            115

<210> SEQ ID NO 52
<211> LENGTH: 119
<212> TYPE: PRT
<213> ORGANISM: Artificial Sequence
<220> FEATURE:
<223> OTHER INFORMATION: Heavy chain variable region of 24D5 H18

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Ser Pro Ser Ser Gly Met Ala Val Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ser Tyr Asp Tyr Phe Asp Tyr Trp Gly Gln Gly
            100                 105                 110

Thr Thr Val Thr Val Ser Ser
            115

<210> SEQ ID NO 53
<211> LENGTH: 119
<212> TYPE: PRT
<213> ORGANISM: Artificial Sequence
<220> FEATURE:
<223> OTHER INFORMATION: Heavy chain variable region of 24D5 H19

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

```
Gly Arg Ile Ser Pro Gly Gly Phe Thr Leu Tyr Asn Glu Lys Phe
        50                  55                  60

Lys Asn Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Gly Ser Ser Tyr Asp Tyr Phe Asp Tyr Trp Gly Gln Gly
                100                 105                 110

Thr Thr Val Thr Val Ser Ser
        115

<210> SEQ ID NO 54
<211> LENGTH: 119
<212> TYPE: PRT
<213> ORGANISM: Artificial Sequence
<220> FEATURE:
<223> OTHER INFORMATION: Heavy chain variable region of 24D5 H20

<400> SEQUENCE: 54

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Arg Ile Gly Pro Asn Ser Gly Phe Thr Ser Tyr Asn Glu Lys Phe
        50                  55                  60

Lys Asn Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Gly Ser Ser Tyr Asp Tyr Phe Asp Tyr Trp Gly Gln Gly
                100                 105                 110

Thr Thr Val Thr Val Ser Ser
        115

<210> SEQ ID NO 55
<211> LENGTH: 111
<212> TYPE: PRT
<213> ORGANISM: Artificial Sequence
<220> FEATURE:
<223> OTHER INFORMATION: Light chain variable region of 24D5 L64

<400> SEQUENCE: 55

Asp Ile Val Leu Thr Gln Ser Pro Ala Ser Leu Ala Val Ser Pro Gly
 1               5                  10                  15

Gln Arg Ala Thr Ile Thr Cys Arg Ala Ser Glu Ser Val Ser Ile His
                20                  25                  30

Gly Thr His Leu Met His Trp Tyr Gln Gln Lys Pro Gly Gln Pro Pro
            35                  40                  45

Lys Leu Leu Ile Tyr Val Ala Ser Tyr Ala Ala Ser Gly Val Pro Ala
        50                  55                  60

Arg Phe Ser Gly Ser Gly Ser Gly Thr Asp Phe Thr Leu Thr Ile Asn
 65                  70                  75                  80

Pro Val Glu Ala Glu Asp Thr Ala Asn Tyr Tyr Cys Gln Gln Ser Phe
                 85                  90                  95

Glu Asp Pro Leu Thr Phe Gly Gln Gly Thr Lys Leu Glu Ile Lys
```

<210> SEQ ID NO 56
<211> LENGTH: 111
<212> TYPE: PRT
<213> ORGANISM: Artificial Sequence
<220> FEATURE:
<223> OTHER INFORMATION: Light chain variable region of 24D5 L61

<400> SEQUENCE: 56

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Glu Asp Thr Ala Asn Tyr Tyr Cys Gln Gln Ser Phe
                85                  90                  95

Glu Asp Pro Leu Thr Phe Gly Gln Gly Thr Lys Leu Glu Ile Lys
            100                 105                 110

<210> SEQ ID NO 57
<211> LENGTH: 111
<212> TYPE: PRT
<213> ORGANISM: Artificial Sequence
<220> FEATURE:
<223> OTHER INFORMATION: Light chain variable region of 24D5 L66

<400> SEQUENCE: 57

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Val Ala Ser Asn Val Phe Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Glu Asp Thr Ala Asn Tyr Tyr Cys Gln Gln Ser Phe
                85                  90                  95

Glu Asp Pro Leu Thr Phe Gly Gln Gly Thr Lys Leu Glu Ile Lys
            100                 105                 110

<210> SEQ ID NO 58
<211> LENGTH: 330
<212> TYPE: PRT
<213> ORGANISM: Artificial Sequence
<220> FEATURE:
<223> OTHER INFORMATION: Heavy chain constant region of IgG1

<400> SEQUENCE: 58

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 59
<211> LENGTH: 107
<212> TYPE: PRT
<213> ORGANISM: Artificial Sequence
<220> FEATURE:
<223> OTHER INFORMATION: Light chain constant region of kappa

<400> SEQUENCE: 59

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60
```

```
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 60
<211> LENGTH: 327
<212> TYPE: PRT
<213> ORGANISM: Artificial Sequence
<220> FEATURE:
<223> OTHER INFORMATION: Heavy chain constant region of human IgG4

<400> SEQUENCE: 60

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320
```

Leu Ser Leu Ser Leu Gly Lys
            325

<210> SEQ ID NO 61
<211> LENGTH: 450
<212> TYPE: PRT
<213> ORGANISM: Artificial Sequence
<220> FEATURE:
<223> OTHER INFORMATION: Sequence of heavy chain of Avelumab(A09)

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

```
Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly Lys
    450

<210> SEQ ID NO 62
<211> LENGTH: 216
<212> TYPE: PRT
<213> ORGANISM: Artificial Sequence
<220> FEATURE:
<223> OTHER INFORMATION: Sequence of light chain of Avelumab(A09)

<400> SEQUENCE: 62

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 63
<211> LENGTH: 448
<212> TYPE: PRT
<213> ORGANISM: Artificial Sequence
```

```
<220> FEATURE:
<223> OTHER INFORMATION: Sequence of heavy chain of 3280A(Genetech)

<400> SEQUENCE: 63
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Asp | Ser |
| | | | 20 | | | | | 25 | | | | | 30 | | |
| Trp | Ile | His | Trp | Val | Arg | Gln | Ala | Pro | Gly | Lys | Gly | Leu | Glu | Trp | Val |
| | | 35 | | | | | 40 | | | | | 45 | | | |
| Ala | Trp | Ile | Ser | Pro | Tyr | Gly | Gly | Ser | Thr | Tyr | Tyr | Ala | Asp | Ser | Val |
| 50 | | | | | 55 | | | | | 60 | | | | | |
| Lys | Gly | Arg | Phe | Thr | Ile | Ser | Ala | Asp | Thr | Ser | Lys | Asn | Thr | Ala | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Arg | His | Trp | Pro | Gly | Gly | Phe | Asp | Tyr | Trp | Gly | Gln | Gly | Thr |
| | | | 100 | | | | | 105 | | | | | 110 | | |
| Leu | Val | Thr | Val | Ser | Ser | Ala | Ser | Thr | Lys | Gly | Pro | Ser | Val | Phe | Pro |
| | | 115 | | | | | 120 | | | | | 125 | | | |
| Leu | Ala | Pro | Ser | Ser | Lys | Ser | Thr | Ser | Gly | Gly | Thr | Ala | Ala | Leu | Gly |
| 130 | | | | | 135 | | | | | 140 | | | | | |
| Cys | Leu | Val | Lys | Asp | Tyr | Phe | Pro | Glu | Pro | Val | Thr | Val | Ser | Trp | Asn |
| 145 | | | | | 150 | | | | | 155 | | | | | 160 |
| Ser | Gly | Ala | Leu | Thr | Ser | Gly | Val | His | Thr | Phe | Pro | Ala | Val | Leu | Gln |
| | | | | 165 | | | | | 170 | | | | | 175 | |
| Ser | Ser | Gly | Leu | Tyr | Ser | Leu | Ser | Ser | Val | Val | Thr | Val | Pro | Ser | Ser |
| | | | 180 | | | | | 185 | | | | | 190 | | |
| Ser | Leu | Gly | Thr | Gln | Thr | Tyr | Ile | Cys | Asn | Val | Asn | His | Lys | Pro | Ser |
| | | 195 | | | | | 200 | | | | | 205 | | | |
| Asn | Thr | Lys | Val | Asp | Lys | Lys | Val | Glu | Pro | Lys | Ser | Cys | Asp | Lys | Thr |
| | 210 | | | | | 215 | | | | | 220 | | | | |
| His | Thr | Cys | Pro | Pro | Cys | Pro | Ala | Pro | Glu | Leu | Leu | Gly | Gly | Pro | Ser |
| 225 | | | | | 230 | | | | | 235 | | | | | 240 |
| Val | Phe | Leu | Phe | Pro | Pro | Lys | Pro | Lys | Asp | Thr | Leu | Met | Ile | Ser | Arg |
| | | | | 245 | | | | | 250 | | | | | 255 | |
| Thr | Pro | Glu | Val | Thr | Cys | Val | Val | Val | Asp | Val | Ser | His | Glu | Asp | Pro |
| | | | 260 | | | | | 265 | | | | | 270 | | |
| Glu | Val | Lys | Phe | Asn | Trp | Tyr | Val | Asp | Gly | Val | Glu | Val | His | Asn | Ala |
| | | 275 | | | | | 280 | | | | | 285 | | | |
| Lys | Thr | Lys | Pro | Arg | Glu | Glu | Gln | Tyr | Ala | Ser | Thr | Tyr | Arg | Val | Val |
| | 290 | | | | | 295 | | | | | 300 | | | | |
| Ser | Val | Leu | Thr | Val | Leu | His | Gln | Asp | Trp | Leu | Asn | Gly | Lys | Glu | Tyr |
| 305 | | | | | 310 | | | | | 315 | | | | | 320 |
| Lys | Cys | Lys | Val | Ser | Asn | Lys | Ala | Leu | Pro | Ala | Pro | Ile | Glu | Lys | Thr |
| | | | | 325 | | | | | 330 | | | | | 335 | |
| Ile | Ser | Lys | Ala | Lys | Gly | Gln | Pro | Arg | Glu | Pro | Gln | Val | Tyr | Thr | Leu |
| | | | 340 | | | | | 345 | | | | | 350 | | |
| Pro | Pro | Ser | Arg | Glu | Glu | Met | Thr | Lys | Asn | Gln | Val | Ser | Leu | Thr | Cys |
| | | 355 | | | | | 360 | | | | | 365 | | | |
| Leu | Val | Lys | Gly | Phe | Tyr | Pro | Ser | Asp | Ile | Ala | Val | Glu | Trp | Glu | Ser |
| | 370 | | | | | 375 | | | | | 380 | | | | |
| Asn | Gly | Gln | Pro | Glu | Asn | Asn | Tyr | Lys | Thr | Thr | Pro | Pro | Val | Leu | Asp |
| 385 | | | | | 390 | | | | | 395 | | | | | 400 |

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 64
<211> LENGTH: 214
<212> TYPE: PRT
<213> ORGANISM: Artificial Sequence
<220> FEATURE:
<223> OTHER INFORMATION: Sequence of light chain of 3280A(Genetech)

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 65
<211> LENGTH: 327
<212> TYPE: PRT
<213> ORGANISM: Artificial Sequence
<220> FEATURE:
<223> OTHER INFORMATION: Heavy chain constant region of human IgG4 S228P

<400> SEQUENCE: 65

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

```
                35                  40                  45
Gly Val His Thr Phe Pro Ala Val Leu Gln Ser Ser Gly Leu Tyr Ser
            50                  55                  60
Leu Ser Ser Val Val Thr Val Pro Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Phe Leu Gly Gly Pro Ser Val Phe Leu Phe Pro Pro Lys Pro Lys
            115                 120                 125
Asp Thr Leu Met Ile Ser Arg Thr Pro Glu Val Thr Cys Val Val Val
        130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 66
<211> LENGTH: 119
<212> TYPE: PRT
<213> ORGANISM: Artificial Sequence
<220> FEATURE:
<223> OTHER INFORMATION: Heavy chain variable region of24D5 H21

<400> SEQUENCE: 66

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Lys
            20                  25                  30
Trp Met Met Trp Val Arg Gln Ala Pro Gly Gln Gly Leu Glu Trp Met
        35                  40                  45
Gly Arg Ile Thr Pro Ser Ser Gly Phe Ala Met Tyr Asn Glu Lys Phe
    50                  55                  60
Lys Asn Arg Val Thr Met Thr Arg Asp Thr Ser Thr Ser Thr Val Tyr
```

```
                65                  70                  75                  80
Met Glu Leu Ser Ser Leu Arg Ser Glu Asp Thr Ala Val Tyr Tyr Cys
                        85                  90                  95

Ala Arg Gly Gly Ser Ser Tyr Asp Tyr Phe Asp Tyr Trp Gly Gln Gly
            100                 105                 110

Thr Thr Val Thr Val Ser Ser
        115

<210> SEQ ID NO 67
<211> LENGTH: 7
<212> TYPE: PRT
<213> ORGANISM: Artificial Sequence
<220> FEATURE:
<223> OTHER INFORMATION: LCDR2 of 24D5 L67

<400> SEQUENCE: 67

Val Ala Ser Asn Val Glu Ser
1               5

<210> SEQ ID NO 68
<211> LENGTH: 7
<212> TYPE: PRT
<213> ORGANISM: Artificial Sequence
<220> FEATURE:
<223> OTHER INFORMATION: LCDR2 of 24D5 L68

<400> SEQUENCE: 68

Val Ala Ser Asn Val Trp Ser
1               5

<210> SEQ ID NO 69
<211> LENGTH: 7
<212> TYPE: PRT
<213> ORGANISM: Artificial Sequence
<220> FEATURE:
<223> OTHER INFORMATION: LCDR2 of 24D5 L69

<400> SEQUENCE: 69

Val Ala Ser Asn Val Tyr Ser
1               5

<210> SEQ ID NO 70
<211> LENGTH: 111
<212> TYPE: PRT
<213> ORGANISM: Artificial Sequence
<220> FEATURE:
<223> OTHER INFORMATION: Light chain variable region of 24D5 L67

<400> SEQUENCE: 70

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Val Ala Ser Asn Val Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Glu Asp Thr Ala Asn Tyr Tyr Cys Gln Gln Ser Phe
                85                  90                  95

Glu Asp Pro Leu Thr Phe Gly Gln Gly Thr Lys Leu Glu Ile Lys
```

<210> SEQ ID NO 71
<211> LENGTH: 111
<212> TYPE: PRT
<213> ORGANISM: Artificial Sequence
<220> FEATURE:
<223> OTHER INFORMATION: Light chain variable region of 24D5 L68

<400> SEQUENCE: 71

```
Asp Ile Val Leu Thr Gln Ser Pro Ala Ser Leu Ala Val Ser Pro Gly
1               5                   10                  15
Gln Arg Ala Thr Ile Thr Cys Arg Ala Ser Glu Ser Val Ser Ile His
            20                  25                  30
Gly Thr His Leu Met His Trp Tyr Gln Gln Lys Pro Gly Gln Pro Pro
        35                  40                  45
Lys Leu Leu Ile Tyr Val Ala Ser Asn Val Trp Ser Gly Val Pro Ala
    50                  55                  60
Arg Phe Ser Gly Ser Gly Ser Gly Thr Asp Phe Thr Leu Thr Ile Asn
65                  70                  75                  80
Pro Val Glu Ala Glu Asp Thr Ala Asn Tyr Tyr Cys Gln Gln Ser Phe
                85                  90                  95
Glu Asp Pro Leu Thr Phe Gly Gln Gly Thr Lys Leu Glu Ile Lys
            100                 105                 110
```

<210> SEQ ID NO 72
<211> LENGTH: 111
<212> TYPE: PRT
<213> ORGANISM: Artificial Sequence
<220> FEATURE:
<223> OTHER INFORMATION: Light chain variable region of 24D5 L69

<400> SEQUENCE: 72

```
Asp Ile Val Leu Thr Gln Ser Pro Ala Ser Leu Ala Val Ser Pro Gly
1               5                   10                  15
Gln Arg Ala Thr Ile Thr Cys Arg Ala Ser Glu Ser Val Ser Ile His
            20                  25                  30
Gly Thr His Leu Met His Trp Tyr Gln Gln Lys Pro Gly Gln Pro Pro
        35                  40                  45
Lys Leu Leu Ile Tyr Val Ala Ser Asn Val Tyr Ser Gly Val Pro Ala
    50                  55                  60
Arg Phe Ser Gly Ser Gly Ser Gly Thr Asp Phe Thr Leu Thr Ile Asn
65                  70                  75                  80
Pro Val Glu Ala Glu Asp Thr Ala Asn Tyr Tyr Cys Gln Gln Ser Phe
                85                  90                  95
Glu Asp Pro Leu Thr Phe Gly Gln Gly Thr Lys Leu Glu Ile Lys
            100                 105                 110
```